(12) United States Patent
Vaughan et al.

(10) Patent No.: US 10,829,540 B2
(45) Date of Patent: Nov. 10, 2020

(54) PHAGE DISPLAY LIBRARY, MEMBERS THEREOF AND USES OF THE SAME

(71) Applicant: MedImmune Limited, Cambridge (GB)

(72) Inventors: Tristan Vaughan, Cambridge (GB); David Lowe, Cambridge (GB); Stacey Chin, Cambridge (GB); Benjamin David Grimshaw, Cambridge (GB); James Button, Cambridge (GB)

(73) Assignee: Medimmune Limited, Cambridge (GB)

( * ) Notice: Subject to any disclaimer, the term of this patent is extended or adjusted under 35 U.S.C. 154(b) by 0 days.

(21) Appl. No.: 15/570,004

(22) PCT Filed: Apr. 29, 2016

(86) PCT No.: PCT/EP2016/059713
§ 371 (c)(1),
(2) Date: Oct. 27, 2017

(87) PCT Pub. No.: WO2016/177651
PCT Pub. Date: Nov. 10, 2016

(65) Prior Publication Data
US 2018/0155409 A1    Jun. 7, 2018

Related U.S. Application Data

(60) Provisional application No. 62/155,646, filed on May 1, 2015.

(51) Int. Cl.
*C40B 40/10* (2006.01)
*C07K 16/00* (2006.01)
(Continued)

(52) U.S. Cl.
CPC ............ *C07K 16/005* (2013.01); *C07K 16/24* (2013.01); *C07K 16/26* (2013.01); *C07K 16/28* (2013.01); *C07K 2317/21* (2013.01); *C07K 2317/33* (2013.01); *C07K 2317/56* (2013.01); *C07K 2317/565* (2013.01); *C07K 2317/567* (2013.01); *C07K 2317/622* (2013.01);
(Continued)

(58) Field of Classification Search
None
See application file for complete search history.

(56) References Cited

U.S. PATENT DOCUMENTS

2014/0243228 A1    8/2014   Benatuil

FOREIGN PATENT DOCUMENTS

WO    WO 2004/065416 A2    5/2004
WO    WO 2011/032181 A2    3/2011

OTHER PUBLICATIONS

Douthwaite, et al., "Affinity maturation of a novel antagonistic human monoclonal antibody with a long V H CDR3 targeting the Class A GPCR formyl-peptide receptor 1", MABS, vol. 7, No. 1, Nov. 19, 2014, pp. 152-166.

(Continued)

*Primary Examiner* — Christian C Boesen

(57) ABSTRACT

The present invention relates to a library (in particular a phage display library) from which an improved human antibody having greater specificity and potency for its target may be generated; and to methods of generating such a human antibody. In particular, the invention relates to a human antibodies against challenging targets obtainable from such a library and which have HCDR3s of at least 18 amino acids in length.

4 Claims, 6 Drawing Sheets

Specification includes a Sequence Listing.

X-ray crystal structure of the anti-FPR Fab FPR0165, which contains a long VH CDR3 loop

VH CDR3

(51) Int. Cl.
*C07K 16/24* (2006.01)
*C07K 16/26* (2006.01)
*C07K 16/28* (2006.01)

(52) U.S. Cl.
CPC ...... *C07K 2317/76* (2013.01); *C07K 2317/90* (2013.01); *C40B 40/10* (2013.01)

(56) References Cited

OTHER PUBLICATIONS

Lowe, et al., "Engineering a high-affinity Anti-IL-15 antibody: Crystal Structure Reveals an -Helix in VH CDR3 as Key Component of Paratope", Journal of Molecular Biology, Academic Press, Uk, vol. 406, No. 1, Dec. 8, 2010, pp. 160-175.

Xu, et al., "Diviserty in the CDR3 region of VH is sufficient for most antibody specifications", Immunity, Cell Press, US., vol. 13, No. 1, Jul. 1, 2000, pp. 37-45.

Zemlin, et al., "Expressed Murine and Human CDR-H3 Intervals of Equal Length Exhibit Distinct Repertoires that Differ in their Amino Acid Composition and Predicted Range of Structures", Journal of Molecular Biology, Academic Press, United Kingdom, vol. 334, No. 4, Dec. 5, 2003, pp. 733-749.

Bonvin, et al., "Purpose-Oriented Antibody Libraries Incorporating Tailored CDR3 Sequences", Antibodies, vol. 4, No. 2, May 20, 2015, pp. 103-122.

Figure 1: X-ray crystal structure of the anti-FPR Fab FPR0165, which contains a long VH CDR3 loop
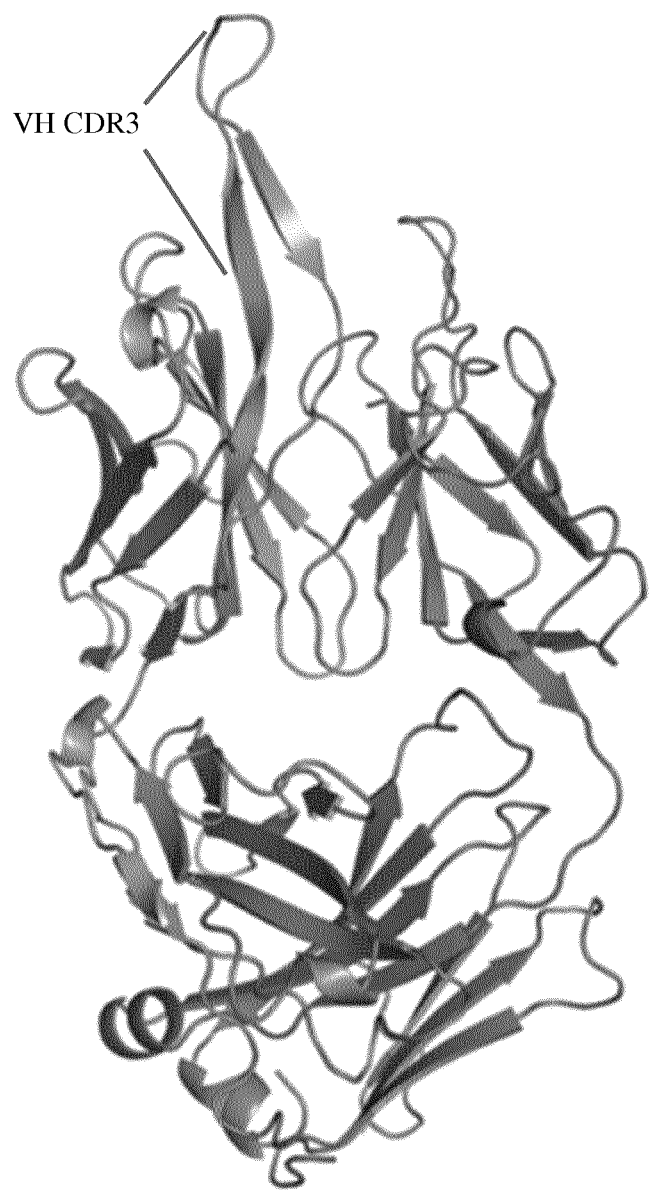

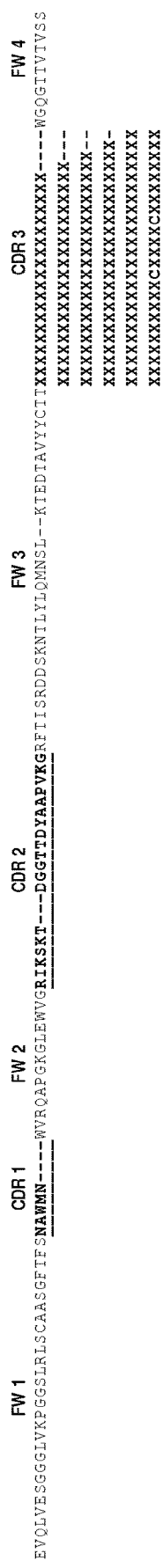
Figure 2 Schematic of VH insert design for long VH CDR3 library
Six constructs representing VH CDR lengths 20-24, plus a 24 amino acid length construct encoding cysteines at loop positions 11 and 16 were synthesised. The six different CDR3 inserts were designed with amino acid compositions as defined in Tables 6-11.

Figure 3: Analysis of cloning efficiency of the 6 VH long CDR3 repertoires
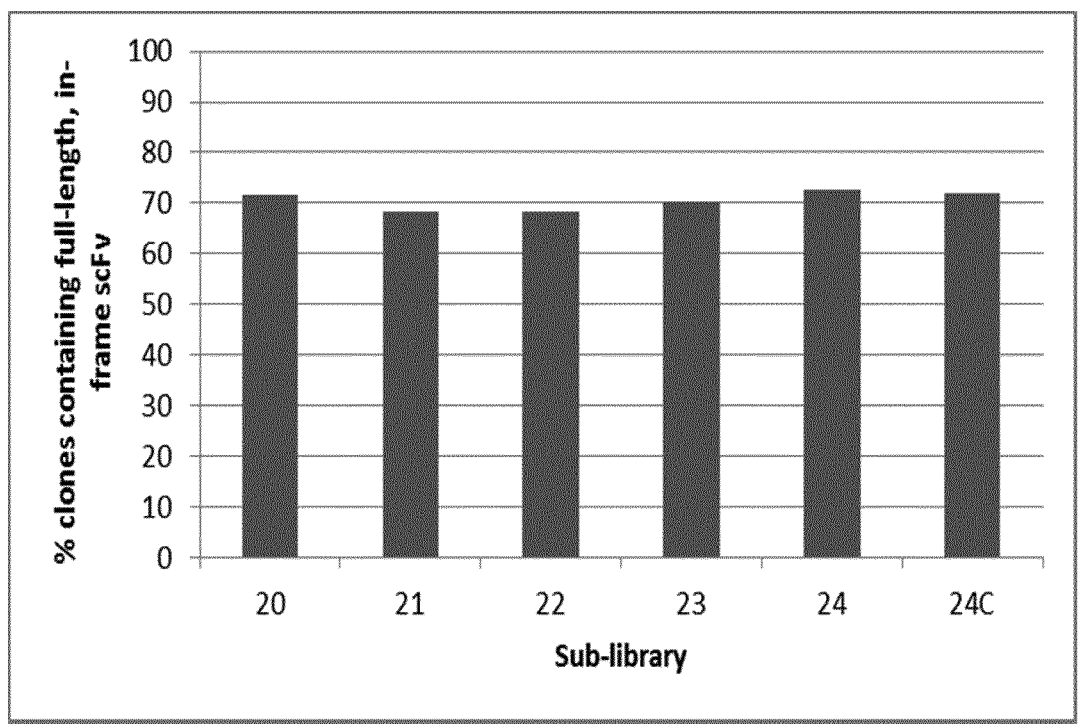

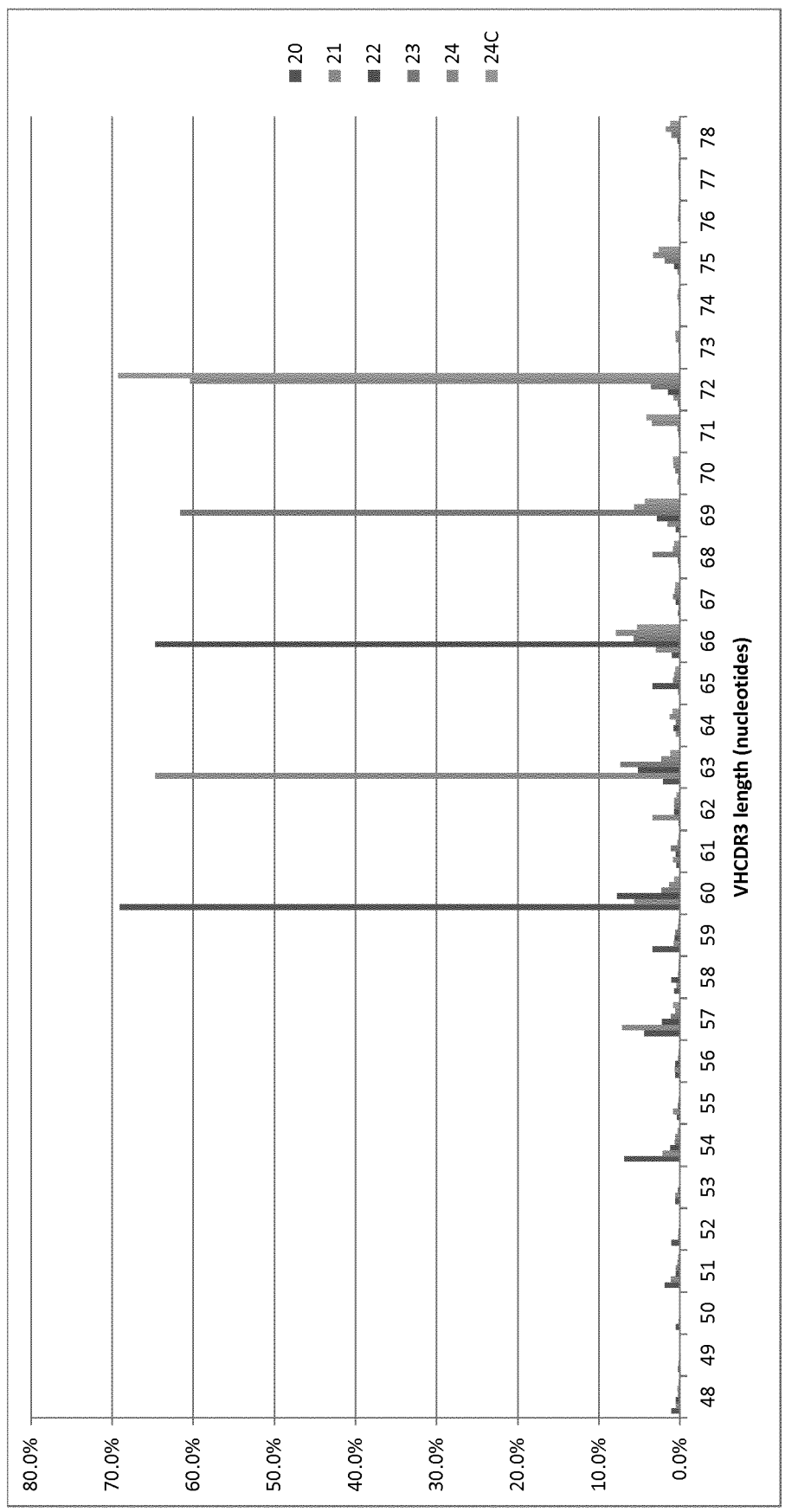
Figure 4: Deep sequencing analysis of the actual VH CDR3 loop lengths following cloning into phagemid vector containing antibody light chain repertoires

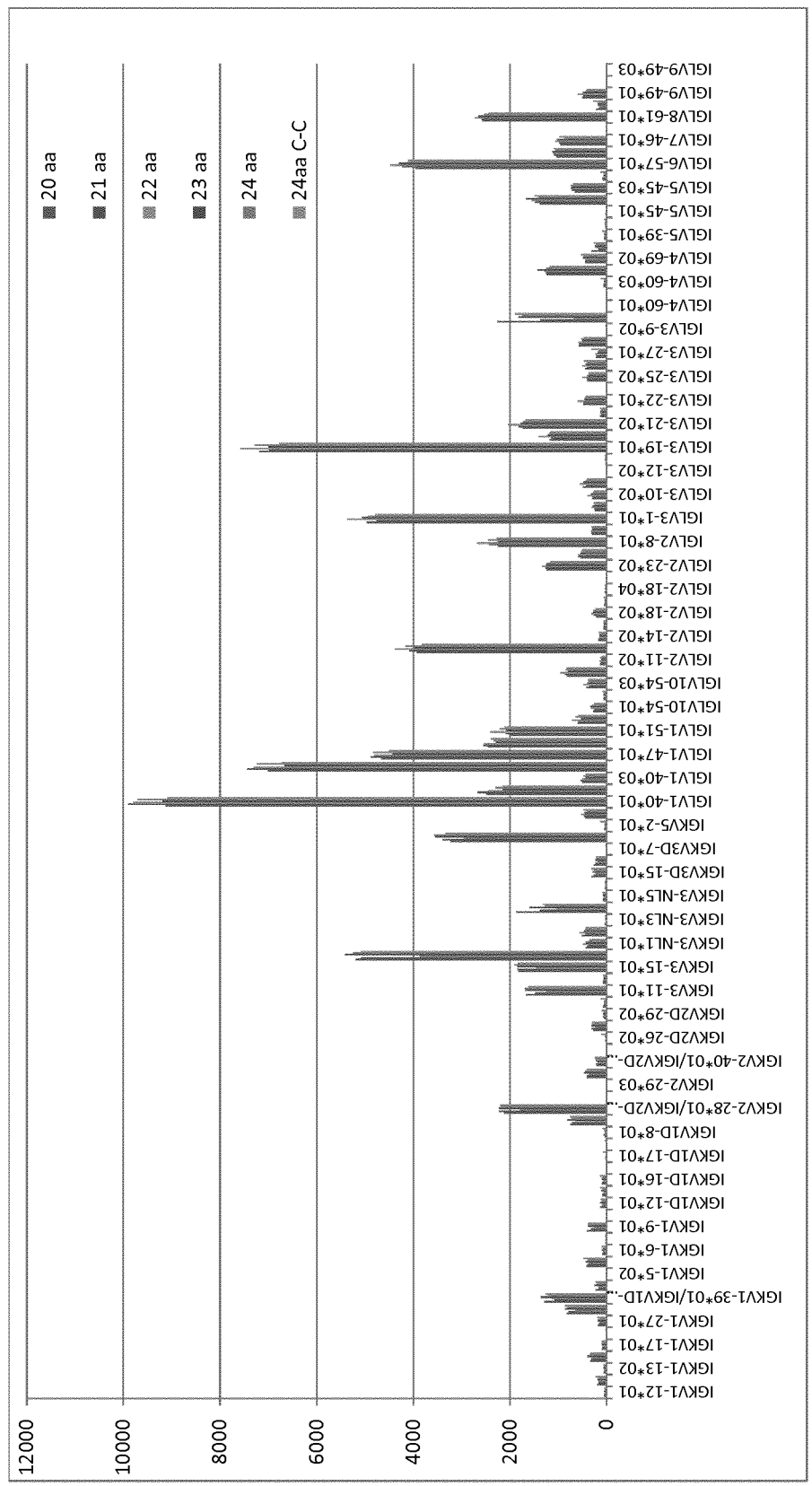
Figure 5: Diversity of light chain germline usage following cloning of the 6 VH repertoire inserts Figure 6: VH (6a, 6b) and VL (6c, 6d) sequence for four anti-P2X4 antibodies (Antibody 1-4)

Antibody Numbering

1  P2X40200
2  P2X40201
3  P2X40203
4  P2X40204

Phage display P2X4 binding – antibodies (Abs) VH sequences

| Antibody number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | a | b | c | d | 36 | 37 | 38 | 39 | 40 | 41 | 42 | 43 | 44 | 45 | 46 | 47 | 48 | 49 | 50 | 51 | 52 | a | b | c | d | e | f | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
|  | | | | | | | | | | | | | | FW1 | | | | | | | | | | | | | | | | | | | | | CDR 1 | | | | | | | | FW 2 | | | | | | | | | | | | | | | | | | | | CDR 2 | | | | | | | | | |
| 1 | E | V | Q | L | V | E | S | G | G | G | L | V | K | P | G | G | S | L | R | L | S | C | A | A | S | G | F | T | F | S | N | A | W | M | N | - | - | - | - | W | V | R | Q | A | P | G | K | G | L | E | W | V | G | R | I | K | S | K | T | - | - | - | D | G | G | T | T | D | Y | A | A | P | V | K | G |
| 2 | E | V | Q | L | V | E | S | G | G | G | L | V | K | P | G | G | S | L | R | L | S | C | A | A | S | G | F | T | F | S | N | A | W | M | N | - | - | - | - | W | V | R | Q | A | P | G | K | G | L | E | W | V | G | R | I | K | S | K | T | - | - | - | D | G | G | T | T | D | Y | A | A | P | V | K | G |
| 3 | E | V | Q | L | V | E | S | G | G | G | L | V | K | P | G | G | S | L | R | L | S | C | A | A | S | G | F | T | F | S | N | A | W | M | N | - | - | - | - | W | V | R | Q | A | P | G | K | G | L | E | W | V | G | R | I | K | S | K | T | - | - | - | D | G | G | T | T | D | Y | A | A | P | V | K | G |
| 4 | E | V | Q | L | V | E | S | G | G | G | L | V | K | P | G | G | S | L | R | L | S | C | A | A | S | G | F | T | F | S | N | A | W | M | N | - | - | - | - | W | V | R | Q | A | P | G | K | G | L | E | W | V | G | R | I | K | S | K | T | - | - | - | D | G | G | T | T | D | Y | A | A | P | V | K | G |

Phage display P2X4 binding – antibodies (Abs) VH sequences

| Antibody | 66 | 67 | 68 | 69 | 70 | 71 | 72 | 73 | 74 | 75 | 76 | 77 | 78 | 79 | 80 | 81 | a | b | c | d | e | 82 | 83 | 84 | 85 | 86 | 87 | 88 | 89 | 90 | 91 | 92 | 93 | a | b | c | d | e | f | g | h | i | j | k | l | m | n | o | p | q | 101 | 102 | 103 | 104 | 105 | a | b | c | d | e | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
|  | | | | | FW 3 | | | | | | | | | | | | | | | | | | | | | | | | | | CDR 3 | | | | | | | | | | | | | | | | | | | | | | FW 4 | | | | | | | | | | | | |
| 1 | R | F | T | I | S | R | D | D | S | K | N | T | L | Y | L | Q | M | N | S | L | - | K | T | E | D | T | A | V | Y | Y | C | T | T | D | Y | G | S | M | Y | F | T | W | G | D | Y | G | K | Y | Y | L | G | F | - | - | - | D | Y | V | G | Q | G | T | T | V | T | V | S | S |
| 2 | R | F | T | I | S | R | D | D | S | K | N | T | L | Y | L | Q | M | N | S | L | - | K | T | E | D | T | A | V | Y | Y | C | T | T | G | G | G | Y | Y | F | Y | G | S | S | G | Y | S | T | Y | Y | Y | G | F | - | - | - | D | P | V | G | Q | G | T | T | V | T | V | S | S |
| 3 | R | F | T | I | S | R | D | D | S | K | N | T | L | Y | L | Q | M | N | S | L | - | K | T | E | D | T | A | V | Y | Y | C | T | T | D | G | G | Y | D | S | S | Y | Y | L | S | T | Y | Y | Y | Y | G | F | - | - | - | D | Y | V | G | Q | G | T | T | V | T | V | S | S |
| 4 | R | F | T | I | S | R | D | D | S | K | N | T | L | Y | L | Q | M | N | S | L | - | K | T | E | D | T | A | V | Y | Y | C | T | V | G | G | H | Y | V | S | T | M | W | G | V | D | F | G | R | Y | L | Y | G | F | - | - | - | D | Y | V | G | Q | G | T | T | V | T | V | S | S |

Phage display P2X4 binding – antibodies (Abs) VL sequences

| Antibody number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | a | b | c | d | e | f | g | h | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | a | b | c | d | e | 52 | 53 | 54 | 55 | 56 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
|  | | | | | | FW 1 | | | | | | | | | | | | | | | | | | | | | CDR 1 | | | | | | | | | | | | | | | | FW 2 | | | | | | | | | | | | | | | CDR 2 | | | | | | | | | | |
| 1 | S | Y | V | L | T | Q | P | P | S | - | V | S | V | S | P | G | Q | T | A | R | I | T | C | S | G | D | F | - | - | - | - | - | - | - | - | L | T | N | Q | Y | A | Y | W | Y | Q | Q | K | P | G | Q | A | P | I | L | L | I | Y | K | D | - | - | - | - | - | S | E | R | P | S |
| 2 | Q | S | V | L | T | Q | P | P | S | - | V | S | V | S | P | G | Q | T | A | R | I | T | C | S | G | D | A | - | - | - | - | - | - | - | - | L | R | S | K | Y | A | S | W | Y | Q | Q | K | P | G | Q | A | P | V | L | V | I | Y | K | D | - | - | - | - | - | T | E | R | P | S |
| 3 | Q | S | V | L | T | Q | P | P | S | - | A | S | V | A | L | G | Q | T | A | R | I | T | C | S | G | D | S | - | - | - | - | - | - | - | - | L | R | S | Y | Y | A | S | W | F | Q | Q | K | P | G | Q | A | P | V | L | V | I | Y | N | D | - | - | - | - | - | N | I | R | P | S |
| 4 | Q | S | V | L | T | Q | P | P | S | - | V | S | L | S | P | G | Q | S | I | T | I | S | C | T | G | T | S | - | - | - | - | - | - | - | - | L | S | K | Q | G | Y | C | Y | W | Y | Q | Q | V | P | G | Q | A | P | V | T | V | I | Y | N | D | - | - | - | - | - | S | R | R | P | S |

Phage display P2X4 binding – antibodies (Abs) VL sequences

| Antibody number | 57 | 58 | 59 | 60 | 61 | 62 | 63 | 64 | 65 | 66 | 67 | 68 | a | b | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | a | b | c | d | e | f | g | h | i | 96 | 97 | 98 | 99 | 100 | 101 | 102 | 103 | 104 | 105 | 106 | a | b | c | 107 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
|  | | | | FW 3 | | | | | | | | | | | | | | | | | | | | | | | | | | | | | | | | | | | | | CDR 3 | | | | | | | | | | | | | FW 4 | | | | | | | | | | |
| 1 | G | I | P | D | R | F | S | G | S | S | S | G | - | - | T | T | V | A | L | T | I | T | S | G | V | Q | A | E | D | E | A | D | Y | Y | C | Q | S | T | D | T | S | G | - | - | - | - | - | - | - | V | V | F | G | G | G | T | K | L | T | V | - | - | - | L |
| 2 | G | I | P | E | R | F | S | G | S | S | S | G | - | - | T | T | V | T | L | T | I | S | G | V | Q | A | E | D | E | A | D | Y | Y | C | Q | S | V | D | T | S | A | S | Y | - | - | - | - | - | - | W | V | F | G | G | G | T | K | V | T | V | - | - | - | L |
| 3 | G | I | P | E | R | F | S | G | S | S | S | G | - | - | T | T | V | T | L | T | I | S | R | A | Q | A | G | D | E | A | D | Y | Y | C | Q | S | R | D | S | S | G | N | - | - | - | - | - | - | - | V | V | F | G | G | G | T | H | L | T | V | - | - | - | L |
| 4 | G | I | P | E | R | F | S | G | S | L | S | G | - | - | T | T | A | S | L | T | I | S | G | A | Q | A | D | D | E | S | D | Y | Y | C | Q | S | S | D | S | S | G | T | - | - | - | - | - | - | - | V | L | F | G | G | G | T | K | V | T | V | - | - | - | L |

SEQUENCE LISTING

```
<160> NUMBER OF SEQ ID NOS: 26

<210> SEQ ID NO 1
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (101)..(101)
<223> OTHER INFORMATION: R, D, G or V
<220> FEATURE:
<221> NAME/KEY: MOD_RES
<222> LOCATION: (102)..(102)
<223> OTHER INFORMATION: R, D, P, Y, S, G or L
<220> FEATURE:
<221> NAME/KEY: MOD_RES
<222> LOCATION: (103)..(103)
<223> OTHER INFORMATION: R, P, Y, T, G, A, F or V
<220> FEATURE:
<221> NAME/KEY: MOD_RES
<222> LOCATION: (104)..(104)
<223> OTHER INFORMATION: R, Y, G or I
<220> FEATURE:
<221> NAME/KEY: MOD_RES
<222> LOCATION: (105)..(105)
<223> OTHER INFORMATION: D, Y, S, G or M
<220> FEATURE:
<221> NAME/KEY: MOD_RES
<222> LOCATION: (106)..(106)
<223> OTHER INFORMATION: D, Y, S, G, V or I
<220> FEATURE:
<221> NAME/KEY: MOD_RES
<222> LOCATION: (107)..(107)
<223> OTHER INFORMATION: R, D, Y, S, G or V
<220> FEATURE:
<221> NAME/KEY: MOD_RES
<222> LOCATION: (108)..(108)
<223> OTHER INFORMATION: D, S, G, M or V
<220> FEATURE:
<221> NAME/KEY: MOD_RES
<222> LOCATION: (109)..(109)
<223> OTHER INFORMATION: Y, S, T, G, L or V
<220> FEATURE:
<221> NAME/KEY: MOD_RES
<222> LOCATION: (110)..(110)
<223> OTHER INFORMATION: Y, S, G, A or V
<220> FEATURE:
<221> NAME/KEY: MOD_RES
```

```
<222> LOCATION: (111)..(111)
<223> OTHER INFORMATION: E, Y, S, G or V
<220> FEATURE:
<221> NAME/KEY: MOD_RES
<222> LOCATION: (112)..(112)
<223> OTHER INFORMATION: Y, G or V
<220> FEATURE:
<221> NAME/KEY: MOD_RES
<222> LOCATION: (113)..(113)
<223> OTHER INFORMATION: R, Y, S or G
<220> FEATURE:
<221> NAME/KEY: MOD_RES
<222> LOCATION: (114)..(114)
<223> OTHER INFORMATION: Y or G
<220> FEATURE:
<221> NAME/KEY: MOD_RES
<222> LOCATION: (116)..(116)
<223> OTHER INFORMATION: D, Y or G
<220> FEATURE:
<221> NAME/KEY: MOD_RES
<222> LOCATION: (117)..(117)
<223> OTHER INFORMATION: Y, W, G or A
<220> FEATURE:
<221> NAME/KEY: MOD_RES
<222> LOCATION: (118)..(118)
<223> OTHER INFORMATION: M or F
<220> FEATURE:
<221> NAME/KEY: MOD_RES
<222> LOCATION: (120)..(120)
<223> OTHER INFORMATION: P, Y or V

<400> SEQUENCE: 1

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Xaa Xaa Xaa Xaa Xaa Xaa Xaa Xaa Xaa Xaa Xaa Xaa
            100                 105                 110

Xaa Xaa Tyr Xaa Xaa Xaa Asp Xaa Trp Gly Gln Gly Thr Thr Val Thr
            115                 120                 125

Val Ser Ser
    130

<210> SEQ ID NO 2
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (101)..(101)
<223> OTHER INFORMATION: R, D, G or V
<220> FEATURE:
<221> NAME/KEY: MOD_RES
<222> LOCATION: (102)..(102)
<223> OTHER INFORMATION: R, D, P, Y, S, G or L
<220> FEATURE:
<221> NAME/KEY: MOD_RES
<222> LOCATION: (103)..(103)
```

```
<223> OTHER INFORMATION: R, P, Y, T, G, A, F or V
<220> FEATURE:
<221> NAME/KEY: MOD_RES
<222> LOCATION: (104)..(104)
<223> OTHER INFORMATION: R, Y, G or I
<220> FEATURE:
<221> NAME/KEY: MOD_RES
<222> LOCATION: (105)..(105)
<223> OTHER INFORMATION: D, Y, S, G or M
<220> FEATURE:
<221> NAME/KEY: MOD_RES
<222> LOCATION: (106)..(106)
<223> OTHER INFORMATION: D, Y, S, G, V or I
<220> FEATURE:
<221> NAME/KEY: MOD_RES
<222> LOCATION: (107)..(107)
<223> OTHER INFORMATION: R, D, Y, S, G or V
<220> FEATURE:
<221> NAME/KEY: MOD_RES
<222> LOCATION: (108)..(108)
<223> OTHER INFORMATION: Y, S, G, L or V
<220> FEATURE:
<221> NAME/KEY: MOD_RES
<222> LOCATION: (109)..(109)
<223> OTHER INFORMATION: Y, S, G or V
<220> FEATURE:
<221> NAME/KEY: MOD_RES
<222> LOCATION: (110)..(110)
<223> OTHER INFORMATION: Y, S, G, L or V
<220> FEATURE:
<221> NAME/KEY: MOD_RES
<222> LOCATION: (111)..(111)
<223> OTHER INFORMATION: Y, S, G, A or V
<220> FEATURE:
<221> NAME/KEY: MOD_RES
<222> LOCATION: (112)..(112)
<223> OTHER INFORMATION: E, Y, S, G or V
<220> FEATURE:
<221> NAME/KEY: MOD_RES
<222> LOCATION: (113)..(113)
<223> OTHER INFORMATION: Y, G or V
<220> FEATURE:
<221> NAME/KEY: MOD_RES
<222> LOCATION: (114)..(114)
<223> OTHER INFORMATION: R, Y, S or G
<220> FEATURE:
<221> NAME/KEY: MOD_RES
<222> LOCATION: (115)..(115)
<223> OTHER INFORMATION: Y or G
<220> FEATURE:
<221> NAME/KEY: MOD_RES
<222> LOCATION: (117)..(117)
<223> OTHER INFORMATION: D, Y or G
<220> FEATURE:
<221> NAME/KEY: MOD_RES
<222> LOCATION: (118)..(118)
<223> OTHER INFORMATION: Y, W, G or A
<220> FEATURE:
<221> NAME/KEY: MOD_RES
<222> LOCATION: (119)..(119)
<223> OTHER INFORMATION: M or F
<220> FEATURE:
<221> NAME/KEY: MOD_RES
<222> LOCATION: (121)..(121)
<223> OTHER INFORMATION: P, Y or V

<400> SEQUENCE: 2

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60
```

```
Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Xaa Xaa Xaa Xaa Xaa Xaa Xaa Xaa Xaa Xaa Xaa Xaa
             100                 105                 110

Xaa Xaa Xaa Tyr Xaa Xaa Xaa Asp Xaa Trp Gly Gln Gly Thr Thr Val
         115                 120                 125

Thr Val Ser Ser
        130

<210> SEQ ID NO 3
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (101)..(101)
<223> OTHER INFORMATION: R, D, G or V
<220> FEATURE:
<221> NAME/KEY: MOD_RES
<222> LOCATION: (102)..(102)
<223> OTHER INFORMATION: R, D, P, Y, S, G or L
<220> FEATURE:
<221> NAME/KEY: MOD_RES
<222> LOCATION: (103)..(103)
<223> OTHER INFORMATION: R, P, Y, T, G, A, F or V
<220> FEATURE:
<221> NAME/KEY: MOD_RES
<222> LOCATION: (104)..(104)
<223> OTHER INFORMATION: R, Y, G or I
<220> FEATURE:
<221> NAME/KEY: MOD_RES
<222> LOCATION: (105)..(105)
<223> OTHER INFORMATION: D, Y, S, G or M
<220> FEATURE:
<221> NAME/KEY: MOD_RES
<222> LOCATION: (106)..(106)
<223> OTHER INFORMATION: D, Y, S, G, V or I
<220> FEATURE:
<221> NAME/KEY: MOD_RES
<222> LOCATION: (107)..(107)
<223> OTHER INFORMATION: R, D, Y, S, G or V
<220> FEATURE:
<221> NAME/KEY: MOD_RES
<222> LOCATION: (108)..(108)
<223> OTHER INFORMATION: D, S, G, M or V
<220> FEATURE:
<221> NAME/KEY: MOD_RES
<222> LOCATION: (109)..(109)
<223> OTHER INFORMATION: Y, S, G, L or V
<220> FEATURE:
<221> NAME/KEY: MOD_RES
<222> LOCATION: (110)..(110)
<223> OTHER INFORMATION: Y, S, G or V
<220> FEATURE:
<221> NAME/KEY: MOD_RES
<222> LOCATION: (111)..(111)
<223> OTHER INFORMATION: Y, S, G, L or V
<220> FEATURE:
<221> NAME/KEY: MOD_RES
<222> LOCATION: (112)..(112)
<223> OTHER INFORMATION: Y, S, G, A or V
<220> FEATURE:
<221> NAME/KEY: MOD_RES
<222> LOCATION: (113)..(113)
<223> OTHER INFORMATION: E, Y, S, G or V
<220> FEATURE:
<221> NAME/KEY: MOD_RES
<222> LOCATION: (114)..(114)
```

```
<223> OTHER INFORMATION: Y, G or V
<220> FEATURE:
<221> NAME/KEY: MOD_RES
<222> LOCATION: (115)..(115)
<223> OTHER INFORMATION: R, Y, S or G
<220> FEATURE:
<221> NAME/KEY: MOD_RES
<222> LOCATION: (116)..(116)
<223> OTHER INFORMATION: Y or G
<220> FEATURE:
<221> NAME/KEY: MOD_RES
<222> LOCATION: (118)..(118)
<223> OTHER INFORMATION: D, Y or G
<220> FEATURE:
<221> NAME/KEY: MOD_RES
<222> LOCATION: (119)..(119)
<223> OTHER INFORMATION: Y, W, G or A
<220> FEATURE:
<221> NAME/KEY: MOD_RES
<222> LOCATION: (120)..(120)
<223> OTHER INFORMATION: M or F
<220> FEATURE:
<221> NAME/KEY: MOD_RES
<222> LOCATION: (122)..(122)
<223> OTHER INFORMATION: P, Y or V

<400> SEQUENCE: 3

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Xaa Xaa Xaa Xaa Xaa Xaa Xaa Xaa Xaa Xaa Xaa Xaa
            100                 105                 110

Xaa Xaa Xaa Xaa Tyr Xaa Xaa Xaa Asp Xaa Trp Gly Gln Gly Thr Thr
        115                 120                 125

Val Thr Val Ser Ser
    130

<210> SEQ ID NO 4
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (101)..(101)
<223> OTHER INFORMATION: R, D, G or V
<220> FEATURE:
<221> NAME/KEY: MOD_RES
<222> LOCATION: (102)..(102)
<223> OTHER INFORMATION: R, D, P, Y, S, G or L
<220> FEATURE:
<221> NAME/KEY: MOD_RES
<222> LOCATION: (103)..(103)
<223> OTHER INFORMATION: R, P, Y, T, G, A, F or V
<220> FEATURE:
<221> NAME/KEY: MOD_RES
<222> LOCATION: (104)..(104)
<223> OTHER INFORMATION: R, Y, G or I
```

```
<220> FEATURE:
<221> NAME/KEY: MOD_RES
<222> LOCATION: (105)..(105)
<223> OTHER INFORMATION: D, Y, S, G or M
<220> FEATURE:
<221> NAME/KEY: MOD_RES
<222> LOCATION: (106)..(106)
<223> OTHER INFORMATION: D, Y, S, G, V or I
<220> FEATURE:
<221> NAME/KEY: MOD_RES
<222> LOCATION: (107)..(107)
<223> OTHER INFORMATION: R, D, Y, S, G or V
<220> FEATURE:
<221> NAME/KEY: MOD_RES
<222> LOCATION: (108)..(108)
<223> OTHER INFORMATION: Y, S, G, L or V
<220> FEATURE:
<221> NAME/KEY: MOD_RES
<222> LOCATION: (109)..(109)
<223> OTHER INFORMATION: Y, S, G or V
<220> FEATURE:
<221> NAME/KEY: MOD_RES
<222> LOCATION: (110)..(110)
<223> OTHER INFORMATION: R, Y, W, S, T, G or A
<220> FEATURE:
<221> NAME/KEY: MOD_RES
<222> LOCATION: (111)..(111)
<223> OTHER INFORMATION: Y, S or G
<220> FEATURE:
<221> NAME/KEY: MOD_RES
<222> LOCATION: (112)..(112)
<223> OTHER INFORMATION: Y, S, G, L or V
<220> FEATURE:
<221> NAME/KEY: MOD_RES
<222> LOCATION: (113)..(113)
<223> OTHER INFORMATION: Y, S, G, A or V
<220> FEATURE:
<221> NAME/KEY: MOD_RES
<222> LOCATION: (114)..(114)
<223> OTHER INFORMATION: E, Y, S, G or V
<220> FEATURE:
<221> NAME/KEY: MOD_RES
<222> LOCATION: (115)..(115)
<223> OTHER INFORMATION: Y, G or V
<220> FEATURE:
<221> NAME/KEY: MOD_RES
<222> LOCATION: (116)..(116)
<223> OTHER INFORMATION: R, Y, S or G
<220> FEATURE:
<221> NAME/KEY: MOD_RES
<222> LOCATION: (117)..(117)
<223> OTHER INFORMATION: Y or G
<220> FEATURE:
<221> NAME/KEY: MOD_RES
<222> LOCATION: (119)..(119)
<223> OTHER INFORMATION: D, Y or G
<220> FEATURE:
<221> NAME/KEY: MOD_RES
<222> LOCATION: (120)..(120)
<223> OTHER INFORMATION: Y, W, G or A
<220> FEATURE:
<221> NAME/KEY: MOD_RES
<222> LOCATION: (121)..(121)
<223> OTHER INFORMATION: M or F
<220> FEATURE:
<221> NAME/KEY: MOD_RES
<222> LOCATION: (123)..(123)
<223> OTHER INFORMATION: P, Y or V

<400> SEQUENCE: 4

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
             20                  25                  30

Trp Met Asn Trp Val Arg Gln Ala Pro Gly Lys Gly Leu Glu Trp Val
         35                  40                  45
```

```
Gly Arg Ile Lys Ser Lys Thr Asp Gly Gly Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Xaa Xaa Xaa Xaa Xaa Xaa Xaa Xaa Xaa Xaa Xaa
            100                 105                 110

Xaa Xaa Xaa Xaa Xaa Tyr Xaa Xaa Xaa Asp Xaa Trp Gly Gln Gly Thr
        115                 120                 125

Thr Val Thr Val Ser Ser
    130

<210> SEQ ID NO 5
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (101)..(101)
<223> OTHER INFORMATION: R, D, G or V
<220> FEATURE:
<221> NAME/KEY: MOD_RES
<222> LOCATION: (102)..(102)
<223> OTHER INFORMATION: R, D, P, Y, S, G or L
<220> FEATURE:
<221> NAME/KEY: MOD_RES
<222> LOCATION: (103)..(103)
<223> OTHER INFORMATION: R, P, Y, T, G, A, F or V
<220> FEATURE:
<221> NAME/KEY: MOD_RES
<222> LOCATION: (104)..(104)
<223> OTHER INFORMATION: R, Y, G or I
<220> FEATURE:
<221> NAME/KEY: MOD_RES
<222> LOCATION: (105)..(105)
<223> OTHER INFORMATION: D, Y, S, G or M
<220> FEATURE:
<221> NAME/KEY: MOD_RES
<222> LOCATION: (106)..(106)
<223> OTHER INFORMATION: D, Y, S, G, V or I
<220> FEATURE:
<221> NAME/KEY: MOD_RES
<222> LOCATION: (107)..(107)
<223> OTHER INFORMATION: R, D, Y, S, G or V
<220> FEATURE:
<221> NAME/KEY: MOD_RES
<222> LOCATION: (108)..(108)
<223> OTHER INFORMATION: D, S, G, M or V
<220> FEATURE:
<221> NAME/KEY: MOD_RES
<222> LOCATION: (109)..(109)
<223> OTHER INFORMATION: Y, S, G, L or V
<220> FEATURE:
<221> NAME/KEY: MOD_RES
<222> LOCATION: (110)..(110)
<223> OTHER INFORMATION: Y, S, G or V
<220> FEATURE:
<221> NAME/KEY: MOD_RES
<222> LOCATION: (111)..(111)
<223> OTHER INFORMATION: R, Y, W, S, T, G or A
<220> FEATURE:
<221> NAME/KEY: MOD_RES
<222> LOCATION: (112)..(112)
<223> OTHER INFORMATION: Y, S or G
<220> FEATURE:
<221> NAME/KEY: MOD_RES
<222> LOCATION: (113)..(113)
<223> OTHER INFORMATION: Y, S, G, L or V
```

```
<220> FEATURE:
<221> NAME/KEY: MOD_RES
<222> LOCATION: (114)..(114)
<223> OTHER INFORMATION: Y, S, G, A or V
<220> FEATURE:
<221> NAME/KEY: MOD_RES
<222> LOCATION: (115)..(115)
<223> OTHER INFORMATION: E, Y, S, G or V
<220> FEATURE:
<221> NAME/KEY: MOD_RES
<222> LOCATION: (116)..(116)
<223> OTHER INFORMATION: Y, G or V
<220> FEATURE:
<221> NAME/KEY: MOD_RES
<222> LOCATION: (117)..(117)
<223> OTHER INFORMATION: R, Y, S or G
<220> FEATURE:
<221> NAME/KEY: MOD_RES
<222> LOCATION: (118)..(118)
<223> OTHER INFORMATION: Y or G
<220> FEATURE:
<221> NAME/KEY: MOD_RES
<222> LOCATION: (120)..(120)
<223> OTHER INFORMATION: D, Y or G
<220> FEATURE:
<221> NAME/KEY: MOD_RES
<222> LOCATION: (121)..(121)
<223> OTHER INFORMATION: Y, W, G or A
<220> FEATURE:
<221> NAME/KEY: MOD_RES
<222> LOCATION: (122)..(122)
<223> OTHER INFORMATION: M or F
<220> FEATURE:
<221> NAME/KEY: MOD_RES
<222> LOCATION: (124)..(124)
<223> OTHER INFORMATION: P, Y or V

<400> SEQUENCE: 5

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Xaa Xaa Xaa Xaa Xaa Xaa Xaa Xaa Xaa Xaa Xaa Xaa
            100                 105                 110

Xaa Xaa Xaa Xaa Xaa Xaa Tyr Xaa Xaa Xaa Asp Xaa Trp Gly Gln Gly
        115                 120                 125

Thr Thr Val Thr Val Ser Ser
    130                 135

<210> SEQ ID NO 6
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (101)..(101)
<223> OTHER INFORMATION: R, D, G or V
<220> FEATURE:
```

-continued

```
<221> NAME/KEY: MOD_RES
<222> LOCATION: (102)..(102)
<223> OTHER INFORMATION: R, D, P, Y, S, G or L
<220> FEATURE:
<221> NAME/KEY: MOD_RES
<222> LOCATION: (103)..(103)
<223> OTHER INFORMATION: R, P, Y, T, G, A, F or V
<220> FEATURE:
<221> NAME/KEY: MOD_RES
<222> LOCATION: (104)..(104)
<223> OTHER INFORMATION: R, Y, G or I
<220> FEATURE:
<221> NAME/KEY: MOD_RES
<222> LOCATION: (105)..(105)
<223> OTHER INFORMATION: D, Y, S, G or M
<220> FEATURE:
<221> NAME/KEY: MOD_RES
<222> LOCATION: (106)..(106)
<223> OTHER INFORMATION: D, Y, S, G, V or I
<220> FEATURE:
<221> NAME/KEY: MOD_RES
<222> LOCATION: (107)..(107)
<223> OTHER INFORMATION: R, D, Y, S, G or V
<220> FEATURE:
<221> NAME/KEY: MOD_RES
<222> LOCATION: (108)..(108)
<223> OTHER INFORMATION: D, S, G, M or V
<220> FEATURE:
<221> NAME/KEY: MOD_RES
<222> LOCATION: (109)..(109)
<223> OTHER INFORMATION: Y, S, G, L or V
<220> FEATURE:
<221> NAME/KEY: MOD_RES
<222> LOCATION: (110)..(110)
<223> OTHER INFORMATION: Y, S, G or V
<220> FEATURE:
<221> NAME/KEY: MOD_RES
<222> LOCATION: (112)..(112)
<223> OTHER INFORMATION: Y, S or G
<220> FEATURE:
<221> NAME/KEY: MOD_RES
<222> LOCATION: (113)..(113)
<223> OTHER INFORMATION: Y, S, G, L or V
<220> FEATURE:
<221> NAME/KEY: MOD_RES
<222> LOCATION: (114)..(114)
<223> OTHER INFORMATION: Y, S, G, A or V
<220> FEATURE:
<221> NAME/KEY: MOD_RES
<222> LOCATION: (115)..(115)
<223> OTHER INFORMATION: E, Y, S, G or V
<220> FEATURE:
<221> NAME/KEY: MOD_RES
<222> LOCATION: (117)..(117)
<223> OTHER INFORMATION: R, Y, S or G
<220> FEATURE:
<221> NAME/KEY: MOD_RES
<222> LOCATION: (118)..(118)
<223> OTHER INFORMATION: Y or G
<220> FEATURE:
<221> NAME/KEY: MOD_RES
<222> LOCATION: (120)..(120)
<223> OTHER INFORMATION: D, Y or G
<220> FEATURE:
<221> NAME/KEY: MOD_RES
<222> LOCATION: (121)..(121)
<223> OTHER INFORMATION: Y, W, G or A
<220> FEATURE:
<221> NAME/KEY: MOD_RES
<222> LOCATION: (122)..(122)
<223> OTHER INFORMATION: M or F
<220> FEATURE:
<221> NAME/KEY: MOD_RES
<222> LOCATION: (124)..(124)
<223> OTHER INFORMATION: P, Y or V

<400> SEQUENCE: 6

Glu Val Gln Leu Val Glu Ser Gly Gly Gly Leu Val Lys Pro Gly Gly
```

```
                1               5                   10                  15
Ser Leu Arg Leu Ser Cys Ala Ala Ser Gly Phe Thr Phe Ser Asn Ala
                20                  25                  30

Trp Met Asn Trp Val Arg Gln Ala Pro Gly Lys Gly Leu Glu Trp Val
                35                  40                  45

Gly Arg Ile Lys Ser Lys Thr Asp Gly Gly Thr Thr Asp Tyr Ala Ala
                50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Xaa Xaa Xaa Xaa Xaa Xaa Xaa Xaa Xaa Cys Xaa
                100                 105                 110

Xaa Xaa Xaa Cys Xaa Xaa Tyr Xaa Xaa Xaa Asp Xaa Trp Gly Gln Gly
                115                 120                 125

Thr Thr Val Thr Val Ser Ser
                130             135
```

<210> SEQ ID NO 7
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
                20                  25                  30

Trp Met Asn Trp Val Arg Gln Ala Pro Gly Lys Gly Leu Glu Trp Val
                35                  40                  45

Gly Arg Ile Lys Ser Lys Thr Asp Gly Gly Thr Thr Asp Tyr Ala Ala
                50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Tyr Gly Ser Met Tyr Phe Thr Trp Gly Asp Tyr
                100                 105                 110

Gly Lys Tyr Tyr Leu Gly Phe Asp Val Trp Gly Gln Gly Thr Thr Val
                115                 120                 125

Thr Val Ser Ser
                130
```

<210> SEQ ID NO 8
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
```

```
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Gly Gly Gly Tyr Tyr Phe Tyr Gly Ser Ser Gly Tyr
            100                 105                 110

Ser Thr Tyr Tyr Trp Met Asp Pro Trp Gly Gln Gly Thr Thr Val Thr
            115                 120                 125

Val Ser Ser
        130

<210> SEQ ID NO 9
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Gly Tyr Asp Ser Ser Tyr Tyr Leu Ser Thr Tyr
            100                 105                 110

Tyr Tyr Tyr Gly Phe Asp Val Trp Gly Gln Gly Thr Thr Val Thr Val
            115                 120                 125

Ser Ser
    130

<210> SEQ ID NO 10
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
```

```
                    35                  40                  45
Gly Arg Ile Lys Ser Lys Thr Asp Gly Gly Thr Thr Asp Tyr Ala Ala
         50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Val Gly Gly His Tyr Val Ser Thr Met Thr Trp Gly
            100                 105                 110

Val Asp Phe Gly Arg Tyr Leu Tyr Gly Phe Asp Val Trp Gly Gln Gly
                115                 120                 125

Thr Thr Val Thr Val Ser Ser
            130                 135
```

```
<210> SEQ ID NO 11
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ser Tyr Val Leu Thr Gln Pro Pro Ser Val Ser Val Ser Pro Gly Gln
 1               5                  10                  15

Thr Ala Thr Ile Thr Cys Ser Gly Asp Thr Leu Pro Gln Arg Tyr Ala
                 20                  25                  30

Tyr Trp Tyr Gln Gln Lys Pro Gly Gln Ala Pro Ile Leu Leu Ile Tyr
             35                  40                  45

Lys Asp Ser Glu Arg Pro Ser Gly Ile Pro Asp Arg Phe Ser Gly Ser
 50                  55                  60

Ser Ser Gly Thr Thr Val Ala Leu Thr Ile Ser Gly Val Gln Ala Glu
 65                  70                  75                  80

Asp Glu Ala Asp Tyr Tyr Cys Gln Ser Thr Asp Thr Ser Gly Val Val
                 85                  90                  95

Phe Gly Gly Gly Thr Lys Val Thr Val Leu
            100                 105
```

```
<210> SEQ ID NO 12
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Ser Val Leu Thr Gln Pro Pro Ser Val Ser Val Ser Pro Gly Gln
 1               5                  10                  15

Thr Ala Arg Ile Ser Cys Ser Gly Glu Ala Leu Thr Asn Gln Tyr Val
                 20                  25                  30

Tyr Trp Tyr Lys Gln Leu Pro Gly Gln Ala Pro Val Leu Leu Ile Tyr
             35                  40                  45

Met Asp Thr Glu Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Val Asp Thr Ser Ala Ser Tyr
```

Trp Val Phe Gly Gly Gly Thr Lys Leu Thr Val Leu
            100                 105

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Ser Glu Leu Thr Gln Asp Pro Ala Ala Ser Val Ala Leu Gly Gln
1               5                   10                  15

Thr Val Thr Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Phe Tyr
        35                  40                  45

Gly Lys Asn Ile Arg Pro Ser Gly Ile Pro Asp Arg Phe Ser Gly Ser
    50                  55                  60

Asp Ser Arg Asp Thr Ala Ser Leu Thr Ile Thr Gly Ala Gln Ala Asp
65                  70                  75                  80

Asp Glu Ala Asp Tyr Tyr Cys Asn Ser Arg Asp Thr Ser Gly Asn Val
                85                  90                  95

Val Phe Gly Gly Gly Thr Lys Val Thr Val Leu
            100                 105

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Ser Val Leu Thr Gln Pro Pro Ser Val Ser Leu Ser Pro Gly Gln
1               5                   10                  15

Thr Ala Arg Ile Thr Cys Ser Gly Asp Val Leu Ser Lys Gln Phe Gly
            20                  25                  30

Tyr Trp Tyr Gln Gln Lys Pro Gly Gln Ala Pro Val Val Ile Tyr
        35                  40                  45

Asn Asp Ser Glu Arg Pro Ser Gly Ile Pro Glu Arg Phe Ser Gly Ser
    50                  55                  60

Ser Ser Gly Thr Thr Val Thr Leu Thr Ile Thr Gly Val Gln Ala Glu
65                  70                  75                  80

Asp Glu Ala Asp Tyr Tyr Cys Gln Ser Ala Asp Ser Ser Gly Thr Val
                85                  90                  95

Leu Phe Gly Gly Gly Thr Lys Leu Thr Val Leu
            100                 105

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (1)..(1)
<223> OTHER INFORMATION: R, K, D, E, P, S, G, A or V
<220> FEATURE:
<221> NAME/KEY: MOD_RES
<222> LOCATION: (2)..(2)
<223> OTHER INFORMATION: R, D, E, H, P, Y, S, G, F, L or V
<220> FEATURE:
<221> NAME/KEY: MOD_RES
<222> LOCATION: (3)..(3)
<223> OTHER INFORMATION: R, D, H, P, Y, S, T, G, A, F or V
<220> FEATURE:
<221> NAME/KEY: MOD_RES
<222> LOCATION: (4)..(4)
<223> OTHER INFORMATION: R, K, D, H, P, Y, W, S, G, A, F, L, V or I
<220> FEATURE:
<221> NAME/KEY: MOD_RES
<222> LOCATION: (5)..(5)
<223> OTHER INFORMATION: K, D, H, P, Y, S, T, G, A, M, L, V or I
<220> FEATURE:
<221> NAME/KEY: MOD_RES
<222> LOCATION: (6)..(6)
<223> OTHER INFORMATION: D, P, Y, S, G, A, M, F, L, V or I
<220> FEATURE:
<221> NAME/KEY: MOD_RES
<222> LOCATION: (7)..(7)
<223> OTHER INFORMATION: R, K, D, E, P, Y, S, T, G, F, V or I
<220> FEATURE:
<221> NAME/KEY: MOD_RES
<222> LOCATION: (8)..(8)
<223> OTHER INFORMATION: R, D, P, Y, S, T, G, A, M, F, L, V or I
<220> FEATURE:
<221> NAME/KEY: MOD_RES
<222> LOCATION: (9)..(9)
<223> OTHER INFORMATION: R, D, P, Y, W, S, T, G, A, M, F, L, V or I
<220> FEATURE:
<221> NAME/KEY: MOD_RES
<222> LOCATION: (10)..(10)
<223> OTHER INFORMATION: R, D, P, Y, S, T, G, A, M, F, L, V or I
<220> FEATURE:
<221> NAME/KEY: MOD_RES
<222> LOCATION: (11)..(11)
<223> OTHER INFORMATION: R, D, E, P, Y, S, T, G, A, F, L, V or I
<220> FEATURE:
<221> NAME/KEY: MOD_RES
<222> LOCATION: (12)..(12)
<223> OTHER INFORMATION: R, K, D, E, P, Y, S, T, G, A, F, L, V or I
<220> FEATURE:
<221> NAME/KEY: MOD_RES
<222> LOCATION: (13)..(13)
<223> OTHER INFORMATION: R, K, D, E, P, Y, S, T or G
<220> FEATURE:
<221> NAME/KEY: MOD_RES
<222> LOCATION: (14)..(14)
<223> OTHER INFORMATION: R, K, E, P, Y, S, T, G or A
<220> FEATURE:
<221> NAME/KEY: MOD_RES
<222> LOCATION: (15)..(15)
<223> OTHER INFORMATION: R, E, P, Y, S, T, G, A, F, L or V
<220> FEATURE:
<221> NAME/KEY: MOD_RES
<222> LOCATION: (16)..(16)
<223> OTHER INFORMATION: D, Y, S, T, G, F or L
<220> FEATURE:
<221> NAME/KEY: MOD_RES
<222> LOCATION: (17)..(17)
<223> OTHER INFORMATION: Y, W, G or A
<220> FEATURE:
<221> NAME/KEY: MOD_RES
<222> LOCATION: (18)..(18)
<223> OTHER INFORMATION: P, M, F or L
<220> FEATURE:
<221> NAME/KEY: MOD_RES
<222> LOCATION: (20)..(20)
<223> OTHER INFORMATION: P, Y, L, V or I

<400> SEQUENCE: 15

Xaa Xaa Xaa Xaa Xaa Xaa Xaa Xaa Xaa Xaa Xaa Xaa Xaa Xaa Xaa
1               5                   10                  15
```

Xaa Xaa Asp Xaa
            20

<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: R, K, D, E, P, S, G, A or V
<220> FEATURE:
<221> NAME/KEY: MOD_RES
<222> LOCATION: (2)..(2)
<223> OTHER INFORMATION: R, D, E, H, P, Y, S, G, F, L or V
<220> FEATURE:
<221> NAME/KEY: MOD_RES
<222> LOCATION: (3)..(3)
<223> OTHER INFORMATION: R, D, H, P, Y, S, T, G, A, F or V
<220> FEATURE:
<221> NAME/KEY: MOD_RES
<222> LOCATION: (4)..(4)
<223> OTHER INFORMATION: R, K, D, H, P, Y, W, S, G, A, F, L, V or I
<220> FEATURE:
<221> NAME/KEY: MOD_RES
<222> LOCATION: (5)..(5)
<223> OTHER INFORMATION: K, D, H, P, Y, S, T, G, A, M, L, V or I
<220> FEATURE:
<221> NAME/KEY: MOD_RES
<222> LOCATION: (6)..(6)
<223> OTHER INFORMATION: D, P, Y, S, G, A, M, F, L, V or I
<220> FEATURE:
<221> NAME/KEY: MOD_RES
<222> LOCATION: (7)..(7)
<223> OTHER INFORMATION: R, K, D, E, P, Y, S, T, G, F, V or I
<220> FEATURE:
<221> NAME/KEY: MOD_RES
<222> LOCATION: (8)..(8)
<223> OTHER INFORMATION: R, D, P, Y, W, S, T, G, A, M, F, L, V or I
<220> FEATURE:
<221> NAME/KEY: MOD_RES
<222> LOCATION: (9)..(9)
<223> OTHER INFORMATION: R, D, P, Y, W, S, T, G, A, F, L, V or I
<220> FEATURE:
<221> NAME/KEY: MOD_RES
<222> LOCATION: (10)..(10)
<223> OTHER INFORMATION: R, D, E, P, Y, W, S, G, A, L, V or I
<220> FEATURE:
<221> NAME/KEY: MOD_RES
<222> LOCATION: (11)..(11)
<223> OTHER INFORMATION: R, D, P, Y, S, T, G, A, M, F, L, V or I
<220> FEATURE:
<221> NAME/KEY: MOD_RES
<222> LOCATION: (12)..(12)
<223> OTHER INFORMATION: R, D, E, P, Y, S, T, G, A, F, L, V or I
<220> FEATURE:
<221> NAME/KEY: MOD_RES
<222> LOCATION: (13)..(13)
<223> OTHER INFORMATION: R, K, D, E, P, Y, S, T, G, A, F, L, V or I
<220> FEATURE:
<221> NAME/KEY: MOD_RES
<222> LOCATION: (14)..(14)
<223> OTHER INFORMATION: R, K, D, E, P, Y, S, T or G
<220> FEATURE:
<221> NAME/KEY: MOD_RES
<222> LOCATION: (15)..(15)
<223> OTHER INFORMATION: R, K, E, P, Y, S, T, G or A
<220> FEATURE:
<221> NAME/KEY: MOD_RES
<222> LOCATION: (16)..(16)
<223> OTHER INFORMATION: R, E, P, Y, S, T, G, A, F, L or V
<220> FEATURE:
<221> NAME/KEY: MOD_RES
<222> LOCATION: (17)..(17)

<223> OTHER INFORMATION: D, Y, S, T, G, F or L
<220> FEATURE:
<221> NAME/KEY: MOD_RES
<222> LOCATION: (18)..(18)
<223> OTHER INFORMATION: Y, W, G or A
<220> FEATURE:
<221> NAME/KEY: MOD_RES
<222> LOCATION: (19)..(19)
<223> OTHER INFORMATION: P, M, F or L
<220> FEATURE:
<221> NAME/KEY: MOD_RES
<222> LOCATION: (21)..(21)
<223> OTHER INFORMATION: P, Y, L, V or I

<400> SEQUENCE: 16

Xaa Xaa Xaa Xaa Xaa Xaa Xaa Xaa Xaa Xaa Xaa Xaa Xaa Xaa Xaa Xaa
1               5                   10                  15

Xaa Xaa Xaa Asp Xaa
            20

<210> SEQ ID NO 17
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: R, K, D, E, P, S, G, A or V
<220> FEATURE:
<221> NAME/KEY: MOD_RES
<222> LOCATION: (2)..(2)
<223> OTHER INFORMATION: R, D, E, H, P, Y, S, G, F, L or V
<220> FEATURE:
<221> NAME/KEY: MOD_RES
<222> LOCATION: (3)..(3)
<223> OTHER INFORMATION: R, D, H, P, Y, S, T, G, A, F or V
<220> FEATURE:
<221> NAME/KEY: MOD_RES
<222> LOCATION: (4)..(4)
<223> OTHER INFORMATION: R, K, D, H, P, Y, W, S, G, A, F, L, V or I
<220> FEATURE:
<221> NAME/KEY: MOD_RES
<222> LOCATION: (5)..(5)
<223> OTHER INFORMATION: K, D, H, P, Y, S, T, G, A, M, L, V or I
<220> FEATURE:
<221> NAME/KEY: MOD_RES
<222> LOCATION: (6)..(6)
<223> OTHER INFORMATION: D, P, Y, S, G, A, M, F, L, V or I
<220> FEATURE:
<221> NAME/KEY: MOD_RES
<222> LOCATION: (7)..(7)
<223> OTHER INFORMATION: R, K, D, E, P, Y, S, T, G, F, V or I
<220> FEATURE:
<221> NAME/KEY: MOD_RES
<222> LOCATION: (8)..(8)
<223> OTHER INFORMATION: R, D, P, Y, S, T, G, A, M, F, L, V or I
<220> FEATURE:
<221> NAME/KEY: MOD_RES
<222> LOCATION: (9)..(9)
<223> OTHER INFORMATION: R, D, P, Y, W, S, T, G, A, M, F, L, V or I
<220> FEATURE:
<221> NAME/KEY: MOD_RES
<222> LOCATION: (10)..(10)
<223> OTHER INFORMATION: R, D, P, Y, W, S, T, G, A, F, L, V or I
<220> FEATURE:
<221> NAME/KEY: MOD_RES
<222> LOCATION: (11)..(11)
<223> OTHER INFORMATION: R, D, E, P, Y, W, S, G, A, L, V or I
<220> FEATURE:
<221> NAME/KEY: MOD_RES
<222> LOCATION: (12)..(12)
<223> OTHER INFORMATION: R, D, P, Y, S, T, G, A, M, F, L, V or I
<220> FEATURE:

```
<221> NAME/KEY: MOD_RES
<222> LOCATION: (13)..(13)
<223> OTHER INFORMATION: R, D, E, P, Y, S, T, G, A, F, L, V or I
<220> FEATURE:
<221> NAME/KEY: MOD_RES
<222> LOCATION: (14)..(14)
<223> OTHER INFORMATION: R, K, D, E, P, Y, S, T, G, A, F, L, V or I
<220> FEATURE:
<221> NAME/KEY: MOD_RES
<222> LOCATION: (15)..(15)
<223> OTHER INFORMATION: R, K, D, E, P, Y, S, T or G
<220> FEATURE:
<221> NAME/KEY: MOD_RES
<222> LOCATION: (16)..(16)
<223> OTHER INFORMATION: R, K, E, P, Y, S, T, G or A
<220> FEATURE:
<221> NAME/KEY: MOD_RES
<222> LOCATION: (17)..(17)
<223> OTHER INFORMATION: R, E, P, Y, S, T, G, A, F, L or V
<220> FEATURE:
<221> NAME/KEY: MOD_RES
<222> LOCATION: (18)..(18)
<223> OTHER INFORMATION: D, Y, S, T, G, F or L
<220> FEATURE:
<221> NAME/KEY: MOD_RES
<222> LOCATION: (19)..(19)
<223> OTHER INFORMATION: Y, W, G or A
<220> FEATURE:
<221> NAME/KEY: MOD_RES
<222> LOCATION: (20)..(20)
<223> OTHER INFORMATION: P, M, F or L
<220> FEATURE:
<221> NAME/KEY: MOD_RES
<222> LOCATION: (22)..(22)
<223> OTHER INFORMATION: P, Y, L, V or I

<400> SEQUENCE: 17

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Asp Xaa
            20

<210> SEQ ID NO 18
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: R, K, D, E, P, S, G, A or V
<220> FEATURE:
<221> NAME/KEY: MOD_RES
<222> LOCATION: (2)..(2)
<223> OTHER INFORMATION: R, D, E, H, P, Y, S, G, F, L or V
<220> FEATURE:
<221> NAME/KEY: MOD_RES
<222> LOCATION: (3)..(3)
<223> OTHER INFORMATION: R, D, H, P, Y, S, T, G, A, F or V
<220> FEATURE:
<221> NAME/KEY: MOD_RES
<222> LOCATION: (4)..(4)
<223> OTHER INFORMATION: R, K, D, H, P, Y, W, S, G, A, F, L, V or I
<220> FEATURE:
<221> NAME/KEY: MOD_RES
<222> LOCATION: (5)..(5)
<223> OTHER INFORMATION: K, D, H, P, Y, S, T, G, A, M, L, V or I
<220> FEATURE:
<221> NAME/KEY: MOD_RES
<222> LOCATION: (6)..(6)
<223> OTHER INFORMATION: D, P, Y, S, G, A, M, F, L, V or I
<220> FEATURE:
<221> NAME/KEY: MOD_RES
<222> LOCATION: (7)..(7)
```

```
<223> OTHER INFORMATION: R, K, D, E, P, Y, S, T, G, F, V or I
<220> FEATURE:
<221> NAME/KEY: MOD_RES
<222> LOCATION: (8)..(8)
<223> OTHER INFORMATION: R, D, P, Y, W, S, T, G, A, M, F, L, V or I
<220> FEATURE:
<221> NAME/KEY: MOD_RES
<222> LOCATION: (9)..(9)
<223> OTHER INFORMATION: R, D, P, Y, W, S, T, G, A, F, L, V or I
<220> FEATURE:
<221> NAME/KEY: MOD_RES
<222> LOCATION: (10)..(10)
<223> OTHER INFORMATION: R, D, Q, P, Y, W, S, T, G or A
<220> FEATURE:
<221> NAME/KEY: MOD_RES
<222> LOCATION: (11)..(11)
<223> OTHER INFORMATION: K, Q, E, H, Y, W, S, T, G, A, F, L or I
<220> FEATURE:
<221> NAME/KEY: MOD_RES
<222> LOCATION: (12)..(12)
<223> OTHER INFORMATION: R, D, E, P, Y, W, S, G, A, L, V or I
<220> FEATURE:
<221> NAME/KEY: MOD_RES
<222> LOCATION: (13)..(13)
<223> OTHER INFORMATION: R, D, P, Y, S, T, G, A, M, F, L, V or I
<220> FEATURE:
<221> NAME/KEY: MOD_RES
<222> LOCATION: (14)..(14)
<223> OTHER INFORMATION: R, D, E, P, Y, S, T, G, A, F, L, V or I
<220> FEATURE:
<221> NAME/KEY: MOD_RES
<222> LOCATION: (15)..(15)
<223> OTHER INFORMATION: R, K, D, E, P, Y, S, T, G, A, F, L, V or I
<220> FEATURE:
<221> NAME/KEY: MOD_RES
<222> LOCATION: (16)..(16)
<223> OTHER INFORMATION: R, K, D, E, P, Y, S, T or G
<220> FEATURE:
<221> NAME/KEY: MOD_RES
<222> LOCATION: (17)..(17)
<223> OTHER INFORMATION: R, K, E, P, Y, S, T, G or A
<220> FEATURE:
<221> NAME/KEY: MOD_RES
<222> LOCATION: (18)..(18)
<223> OTHER INFORMATION: R, E, P, Y, S, T, G, A, F, L or V
<220> FEATURE:
<221> NAME/KEY: MOD_RES
<222> LOCATION: (19)..(19)
<223> OTHER INFORMATION: D, Y, S, T, G, F or L
<220> FEATURE:
<221> NAME/KEY: MOD_RES
<222> LOCATION: (20)..(20)
<223> OTHER INFORMATION: Y, W, G or A
<220> FEATURE:
<221> NAME/KEY: MOD_RES
<222> LOCATION: (21)..(21)
<223> OTHER INFORMATION: P, M, F or L
<220> FEATURE:
<221> NAME/KEY: MOD_RES
<222> LOCATION: (23)..(23)
<223> OTHER INFORMATION: P, Y, L, V or I

<400> SEQUENCE: 18

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Asp Xaa
            20

<210> SEQ ID NO 19
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

```
<221> NAME/KEY: MOD_RES
<222> LOCATION: (1)..(1)
<223> OTHER INFORMATION: R, K, D, E, P, S, G, A or V
<220> FEATURE:
<221> NAME/KEY: MOD_RES
<222> LOCATION: (2)..(2)
<223> OTHER INFORMATION: R, D, E, H, P, Y, S, G, F, L or V
<220> FEATURE:
<221> NAME/KEY: MOD_RES
<222> LOCATION: (3)..(3)
<223> OTHER INFORMATION: R, D, H, P, Y, S, T, G, A, F or V
<220> FEATURE:
<221> NAME/KEY: MOD_RES
<222> LOCATION: (4)..(4)
<223> OTHER INFORMATION: R, K, D, H, P, Y, W, S, G, A, F, L, V or I
<220> FEATURE:
<221> NAME/KEY: MOD_RES
<222> LOCATION: (5)..(5)
<223> OTHER INFORMATION: K, D, H, P, Y, S, T, G, A, M, L, V or I
<220> FEATURE:
<221> NAME/KEY: MOD_RES
<222> LOCATION: (6)..(6)
<223> OTHER INFORMATION: D, P, Y, S, G, A, M, F, L, V or I
<220> FEATURE:
<221> NAME/KEY: MOD_RES
<222> LOCATION: (7)..(7)
<223> OTHER INFORMATION: R, K, D, E, P, Y, S, T, G, F, V or I
<220> FEATURE:
<221> NAME/KEY: MOD_RES
<222> LOCATION: (8)..(8)
<223> OTHER INFORMATION: R, D, P, Y, S, T, G, A, M, F, L, V or I
<220> FEATURE:
<221> NAME/KEY: MOD_RES
<222> LOCATION: (9)..(9)
<223> OTHER INFORMATION: R, D, P, Y, W, S, T, G, A, M, F, L, V or I
<220> FEATURE:
<221> NAME/KEY: MOD_RES
<222> LOCATION: (10)..(10)
<223> OTHER INFORMATION: R, D, P, Y, W, S, T, G, A, F, L, V or I
<220> FEATURE:
<221> NAME/KEY: MOD_RES
<222> LOCATION: (11)..(11)
<223> OTHER INFORMATION: R, D, Q, P, Y, W, S, T, G or A
<220> FEATURE:
<221> NAME/KEY: MOD_RES
<222> LOCATION: (12)..(12)
<223> OTHER INFORMATION: K, Q, E, H, Y, W, S, T, G, A, F, L or I
<220> FEATURE:
<221> NAME/KEY: MOD_RES
<222> LOCATION: (13)..(13)
<223> OTHER INFORMATION: R, D, E, P, Y, W, S, G, A, L, V or I
<220> FEATURE:
<221> NAME/KEY: MOD_RES
<222> LOCATION: (14)..(14)
<223> OTHER INFORMATION: R, D, P, Y, S, T, G, A, M, F, L, V or I
<220> FEATURE:
<221> NAME/KEY: MOD_RES
<222> LOCATION: (15)..(15)
<223> OTHER INFORMATION: R, D, E, P, Y, S, T, G, A, F, L, V or I
<220> FEATURE:
<221> NAME/KEY: MOD_RES
<222> LOCATION: (16)..(16)
<223> OTHER INFORMATION: R, K, D, E, P, Y, S, T, G, A, F, L, V or I
<220> FEATURE:
<221> NAME/KEY: MOD_RES
<222> LOCATION: (17)..(17)
<223> OTHER INFORMATION: R, K, D, E, P, Y, S, T or G
<220> FEATURE:
<221> NAME/KEY: MOD_RES
<222> LOCATION: (18)..(18)
<223> OTHER INFORMATION: R, K, E, P, Y, S, T, G or A
<220> FEATURE:
<221> NAME/KEY: MOD_RES
<222> LOCATION: (19)..(19)
<223> OTHER INFORMATION: R, E, P, Y, S, T, G, A, F, L or V
<220> FEATURE:
<221> NAME/KEY: MOD_RES
<222> LOCATION: (20)..(20)
<223> OTHER INFORMATION: D, Y, S, T, G, F or L
```

```
<220> FEATURE:
<221> NAME/KEY: MOD_RES
<222> LOCATION: (21)..(21)
<223> OTHER INFORMATION: Y, W, G or A
<220> FEATURE:
<221> NAME/KEY: MOD_RES
<222> LOCATION: (22)..(22)
<223> OTHER INFORMATION: P, M, F or L
<220> FEATURE:
<221> NAME/KEY: MOD_RES
<222> LOCATION: (24)..(24)
<223> OTHER INFORMATION: P, Y, L, V or I

<400> SEQUENCE: 19

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Asp Xaa
            20

<210> SEQ ID NO 20
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: R, K, D, E, P, S, G, A or V
<220> FEATURE:
<221> NAME/KEY: MOD_RES
<222> LOCATION: (2)..(2)
<223> OTHER INFORMATION: R, D, E, H, P, Y, S, G, F, L or V
<220> FEATURE:
<221> NAME/KEY: MOD_RES
<222> LOCATION: (3)..(3)
<223> OTHER INFORMATION: R, D, H, P, Y, S, T, G, A, F or V
<220> FEATURE:
<221> NAME/KEY: MOD_RES
<222> LOCATION: (4)..(4)
<223> OTHER INFORMATION: R, K, D, H, P, Y, W, S, G, A, F, L, V or I
<220> FEATURE:
<221> NAME/KEY: MOD_RES
<222> LOCATION: (5)..(5)
<223> OTHER INFORMATION: K, D, H, P, Y, S, T, G, A, M, L, V or I
<220> FEATURE:
<221> NAME/KEY: MOD_RES
<222> LOCATION: (6)..(6)
<223> OTHER INFORMATION: D, P, Y, S, G, A, M, F, L, V or I
<220> FEATURE:
<221> NAME/KEY: MOD_RES
<222> LOCATION: (7)..(7)
<223> OTHER INFORMATION: R, K, D, E, P, Y, S, T, G, F, V or I
<220> FEATURE:
<221> NAME/KEY: MOD_RES
<222> LOCATION: (8)..(8)
<223> OTHER INFORMATION: R, D, P, Y, S, T, G, A, M, F, L, V or I
<220> FEATURE:
<221> NAME/KEY: MOD_RES
<222> LOCATION: (9)..(9)
<223> OTHER INFORMATION: R, D, P, Y, W, S, T, G, A, M, F, L, V or I
<220> FEATURE:
<221> NAME/KEY: MOD_RES
<222> LOCATION: (10)..(10)
<223> OTHER INFORMATION: R, D, P, Y, W, S, T, G, A, F, L, V or I
<220> FEATURE:
<221> NAME/KEY: MOD_RES
<222> LOCATION: (12)..(12)
<223> OTHER INFORMATION: K, Q, E, H, Y, W, S, T, G, A, F, L or I
<220> FEATURE:
<221> NAME/KEY: MOD_RES
<222> LOCATION: (13)..(13)
<223> OTHER INFORMATION: R, D, E, P, Y, W, S, G, A, L, V or I
<220> FEATURE:
<221> NAME/KEY: MOD_RES
```

-continued

```
<222> LOCATION: (14)..(14)
<223> OTHER INFORMATION: R, D, P, Y, S, T, G, A, M, F, L, V or I
<220> FEATURE:
<221> NAME/KEY: MOD_RES
<222> LOCATION: (15)..(15)
<223> OTHER INFORMATION: R, D, E, P, Y, S, T, G, A, F, L, V or I
<220> FEATURE:
<221> NAME/KEY: MOD_RES
<222> LOCATION: (17)..(17)
<223> OTHER INFORMATION: R, K, D, E, P, Y, S, T or G
<220> FEATURE:
<221> NAME/KEY: MOD_RES
<222> LOCATION: (18)..(18)
<223> OTHER INFORMATION: R, K, E, P, Y, S, T, G or A
<220> FEATURE:
<221> NAME/KEY: MOD_RES
<222> LOCATION: (19)..(19)
<223> OTHER INFORMATION: R, E, P, Y, S, T, G, A, F, L or V
<220> FEATURE:
<221> NAME/KEY: MOD_RES
<222> LOCATION: (20)..(20)
<223> OTHER INFORMATION: D, Y, S, T, G, F or L
<220> FEATURE:
<221> NAME/KEY: MOD_RES
<222> LOCATION: (21)..(21)
<223> OTHER INFORMATION: Y, W, G or A
<220> FEATURE:
<221> NAME/KEY: MOD_RES
<222> LOCATION: (22)..(22)
<223> OTHER INFORMATION: P, M, F or L
<220> FEATURE:
<221> NAME/KEY: MOD_RES
<222> LOCATION: (24)..(24)
<223> OTHER INFORMATION: P, Y, L, V or I

<400> SEQUENCE: 20

Xaa Xaa Xaa Xaa Xaa Xaa Xaa Xaa Xaa Xaa Cys Xaa Xaa Xaa Xaa Cys
1               5                   10                  15

Xaa Xaa Xaa Xaa Xaa Xaa Asp Xaa
            20

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: R, D, G or V
<220> FEATURE:
<221> NAME/KEY: MOD_RES
<222> LOCATION: (2)..(2)
<223> OTHER INFORMATION: R, D, P, Y, S, G or L
<220> FEATURE:
<221> NAME/KEY: MOD_RES
<222> LOCATION: (3)..(3)
<223> OTHER INFORMATION: R, P, Y, T, G, A, F or V
<220> FEATURE:
<221> NAME/KEY: MOD_RES
<222> LOCATION: (4)..(4)
<223> OTHER INFORMATION: R, Y, G or I
<220> FEATURE:
<221> NAME/KEY: MOD_RES
<222> LOCATION: (5)..(5)
<223> OTHER INFORMATION: D, Y, S, G or M
<220> FEATURE:
<221> NAME/KEY: MOD_RES
<222> LOCATION: (6)..(6)
<223> OTHER INFORMATION: D, Y, S, G, V or I
<220> FEATURE:
<221> NAME/KEY: MOD_RES
<222> LOCATION: (7)..(7)
<223> OTHER INFORMATION: R, D, Y, S, G or V
```

```
<220> FEATURE:
<221> NAME/KEY: MOD_RES
<222> LOCATION: (8)..(8)
<223> OTHER INFORMATION: D, S, G, M or V
<220> FEATURE:
<221> NAME/KEY: MOD_RES
<222> LOCATION: (9)..(9)
<223> OTHER INFORMATION: Y, S, T, G, L or V
<220> FEATURE:
<221> NAME/KEY: MOD_RES
<222> LOCATION: (10)..(10)
<223> OTHER INFORMATION: Y, S, G, A or V
<220> FEATURE:
<221> NAME/KEY: MOD_RES
<222> LOCATION: (11)..(11)
<223> OTHER INFORMATION: E, Y, S, G or V
<220> FEATURE:
<221> NAME/KEY: MOD_RES
<222> LOCATION: (12)..(12)
<223> OTHER INFORMATION: Y, G or V
<220> FEATURE:
<221> NAME/KEY: MOD_RES
<222> LOCATION: (13)..(13)
<223> OTHER INFORMATION: R, Y, S or G
<220> FEATURE:
<221> NAME/KEY: MOD_RES
<222> LOCATION: (14)..(14)
<223> OTHER INFORMATION: Y or G
<220> FEATURE:
<221> NAME/KEY: MOD_RES
<222> LOCATION: (16)..(16)
<223> OTHER INFORMATION: D, Y or G
<220> FEATURE:
<221> NAME/KEY: MOD_RES
<222> LOCATION: (17)..(17)
<223> OTHER INFORMATION: Y, W, G or A
<220> FEATURE:
<221> NAME/KEY: MOD_RES
<222> LOCATION: (18)..(18)
<223> OTHER INFORMATION: M or F
<220> FEATURE:
<221> NAME/KEY: MOD_RES
<222> LOCATION: (20)..(20)
<223> OTHER INFORMATION: P, Y or V

<400> SEQUENCE: 21

Xaa Xaa Xaa Xaa Xaa Xaa Xaa Xaa Xaa Xaa Xaa Xaa Xaa Xaa Tyr Xaa
1               5                   10                  15

Xaa Xaa Asp Xaa
            20

<210> SEQ ID NO 22
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: R, D, G or V
<220> FEATURE:
<221> NAME/KEY: MOD_RES
<222> LOCATION: (2)..(2)
<223> OTHER INFORMATION: R, D, P, Y, S, G or L
<220> FEATURE:
<221> NAME/KEY: MOD_RES
<222> LOCATION: (3)..(3)
<223> OTHER INFORMATION: R, P, Y, T, G, A, F or V
<220> FEATURE:
<221> NAME/KEY: MOD_RES
<222> LOCATION: (4)..(4)
<223> OTHER INFORMATION: R, Y, G or I
<220> FEATURE:
<221> NAME/KEY: MOD_RES
```

```
<222> LOCATION: (5)..(5)
<223> OTHER INFORMATION: D, Y, S, G or M
<220> FEATURE:
<221> NAME/KEY: MOD_RES
<222> LOCATION: (6)..(6)
<223> OTHER INFORMATION: D, Y, S, G, V or I
<220> FEATURE:
<221> NAME/KEY: MOD_RES
<222> LOCATION: (7)..(7)
<223> OTHER INFORMATION: R, D, Y, S, G or V
<220> FEATURE:
<221> NAME/KEY: MOD_RES
<222> LOCATION: (8)..(8)
<223> OTHER INFORMATION: Y, S, G, L or V
<220> FEATURE:
<221> NAME/KEY: MOD_RES
<222> LOCATION: (9)..(9)
<223> OTHER INFORMATION: Y, S, G or V
<220> FEATURE:
<221> NAME/KEY: MOD_RES
<222> LOCATION: (10)..(10)
<223> OTHER INFORMATION: Y, S, G, L or V
<220> FEATURE:
<221> NAME/KEY: MOD_RES
<222> LOCATION: (11)..(11)
<223> OTHER INFORMATION: Y, S, G, A or V
<220> FEATURE:
<221> NAME/KEY: MOD_RES
<222> LOCATION: (12)..(12)
<223> OTHER INFORMATION: E, Y, S, G or V
<220> FEATURE:
<221> NAME/KEY: MOD_RES
<222> LOCATION: (13)..(13)
<223> OTHER INFORMATION: Y, G or V
<220> FEATURE:
<221> NAME/KEY: MOD_RES
<222> LOCATION: (14)..(14)
<223> OTHER INFORMATION: R, Y, S or G
<220> FEATURE:
<221> NAME/KEY: MOD_RES
<222> LOCATION: (15)..(15)
<223> OTHER INFORMATION: Y or G
<220> FEATURE:
<221> NAME/KEY: MOD_RES
<222> LOCATION: (17)..(17)
<223> OTHER INFORMATION: D, Y or G
<220> FEATURE:
<221> NAME/KEY: MOD_RES
<222> LOCATION: (18)..(18)
<223> OTHER INFORMATION: Y, W, G or A
<220> FEATURE:
<221> NAME/KEY: MOD_RES
<222> LOCATION: (19)..(19)
<223> OTHER INFORMATION: M or F
<220> FEATURE:
<221> NAME/KEY: MOD_RES
<222> LOCATION: (21)..(21)
<223> OTHER INFORMATION: P, Y or V

<400> SEQUENCE: 22

Xaa Xaa Xaa Xaa Xaa Xaa Xaa Xaa Xaa Xaa Xaa Xaa Xaa Xaa Xaa Tyr
1               5                   10                  15

Xaa Xaa Xaa Asp Xaa
            20

<210> SEQ ID NO 23
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: R, D, G or V
```

```
<220> FEATURE:
<221> NAME/KEY: MOD_RES
<222> LOCATION: (2)..(2)
<223> OTHER INFORMATION: R, D, P, Y, S, G or L
<220> FEATURE:
<221> NAME/KEY: MOD_RES
<222> LOCATION: (3)..(3)
<223> OTHER INFORMATION: R, P, Y, T, G, A, F or V
<220> FEATURE:
<221> NAME/KEY: MOD_RES
<222> LOCATION: (4)..(4)
<223> OTHER INFORMATION: R, Y, G or I
<220> FEATURE:
<221> NAME/KEY: MOD_RES
<222> LOCATION: (5)..(5)
<223> OTHER INFORMATION: D, Y, S, G or M
<220> FEATURE:
<221> NAME/KEY: MOD_RES
<222> LOCATION: (6)..(6)
<223> OTHER INFORMATION: D, Y, S, G, V or I
<220> FEATURE:
<221> NAME/KEY: MOD_RES
<222> LOCATION: (7)..(7)
<223> OTHER INFORMATION: R, D, Y, S, G or V
<220> FEATURE:
<221> NAME/KEY: MOD_RES
<222> LOCATION: (8)..(8)
<223> OTHER INFORMATION: D, S, G, M or V
<220> FEATURE:
<221> NAME/KEY: MOD_RES
<222> LOCATION: (9)..(9)
<223> OTHER INFORMATION: Y, S, G, L or V
<220> FEATURE:
<221> NAME/KEY: MOD_RES
<222> LOCATION: (10)..(10)
<223> OTHER INFORMATION: Y, S, G or V
<220> FEATURE:
<221> NAME/KEY: MOD_RES
<222> LOCATION: (11)..(11)
<223> OTHER INFORMATION: Y, S, G, L or V
<220> FEATURE:
<221> NAME/KEY: MOD_RES
<222> LOCATION: (12)..(12)
<223> OTHER INFORMATION: Y, S, G, A or V
<220> FEATURE:
<221> NAME/KEY: MOD_RES
<222> LOCATION: (13)..(13)
<223> OTHER INFORMATION: E, Y, S, G or V
<220> FEATURE:
<221> NAME/KEY: MOD_RES
<222> LOCATION: (14)..(14)
<223> OTHER INFORMATION: Y, G or V
<220> FEATURE:
<221> NAME/KEY: MOD_RES
<222> LOCATION: (15)..(15)
<223> OTHER INFORMATION: R, Y, S or G
<220> FEATURE:
<221> NAME/KEY: MOD_RES
<222> LOCATION: (16)..(16)
<223> OTHER INFORMATION: Y or G
<220> FEATURE:
<221> NAME/KEY: MOD_RES
<222> LOCATION: (18)..(18)
<223> OTHER INFORMATION: D, Y or G
<220> FEATURE:
<221> NAME/KEY: MOD_RES
<222> LOCATION: (19)..(19)
<223> OTHER INFORMATION: Y, W, G or A
<220> FEATURE:
<221> NAME/KEY: MOD_RES
<222> LOCATION: (20)..(20)
<223> OTHER INFORMATION: M or F
<220> FEATURE:
<221> NAME/KEY: MOD_RES
<222> LOCATION: (22)..(22)
<223> OTHER INFORMATION: P, Y or V

<400> SEQUENCE: 23
```

```
Xaa Xaa Xaa Xaa Xaa Xaa Xaa Xaa Xaa Xaa Xaa Xaa Xaa Xaa Xaa
1               5                   10                  15

Tyr Xaa Xaa Xaa Asp Xaa
            20
```

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: R, D, G or V
<220> FEATURE:
<221> NAME/KEY: MOD_RES
<222> LOCATION: (2)..(2)
<223> OTHER INFORMATION: R, D, P, Y, S, G or L
<220> FEATURE:
<221> NAME/KEY: MOD_RES
<222> LOCATION: (3)..(3)
<223> OTHER INFORMATION: R, P, Y, T, G, A, F or V
<220> FEATURE:
<221> NAME/KEY: MOD_RES
<222> LOCATION: (4)..(4)
<223> OTHER INFORMATION: R, Y, G or I
<220> FEATURE:
<221> NAME/KEY: MOD_RES
<222> LOCATION: (5)..(5)
<223> OTHER INFORMATION: D, Y, S, G or M
<220> FEATURE:
<221> NAME/KEY: MOD_RES
<222> LOCATION: (6)..(6)
<223> OTHER INFORMATION: D, Y, S, G, V or I
<220> FEATURE:
<221> NAME/KEY: MOD_RES
<222> LOCATION: (7)..(7)
<223> OTHER INFORMATION: R, D, Y, S, G or V
<220> FEATURE:
<221> NAME/KEY: MOD_RES
<222> LOCATION: (8)..(8)
<223> OTHER INFORMATION: Y, S, G, L or V
<220> FEATURE:
<221> NAME/KEY: MOD_RES
<222> LOCATION: (9)..(9)
<223> OTHER INFORMATION: Y, S, G or V
<220> FEATURE:
<221> NAME/KEY: MOD_RES
<222> LOCATION: (10)..(10)
<223> OTHER INFORMATION: R, Y, W, S, T, G or A
<220> FEATURE:
<221> NAME/KEY: MOD_RES
<222> LOCATION: (11)..(11)
<223> OTHER INFORMATION: Y, S or G
<220> FEATURE:
<221> NAME/KEY: MOD_RES
<222> LOCATION: (12)..(12)
<223> OTHER INFORMATION: Y, S, G, L or V
<220> FEATURE:
<221> NAME/KEY: MOD_RES
<222> LOCATION: (13)..(13)
<223> OTHER INFORMATION: Y, S, G, A or V
<220> FEATURE:
<221> NAME/KEY: MOD_RES
<222> LOCATION: (14)..(14)
<223> OTHER INFORMATION: E, Y, S, G or V
<220> FEATURE:
<221> NAME/KEY: MOD_RES
<222> LOCATION: (15)..(15)
<223> OTHER INFORMATION: Y, G or V
<220> FEATURE:
<221> NAME/KEY: MOD_RES
<222> LOCATION: (16)..(16)
<223> OTHER INFORMATION: R, Y, S or G
<220> FEATURE:

```
<221> NAME/KEY: MOD_RES
<222> LOCATION: (17)..(17)
<223> OTHER INFORMATION: Y or G
<220> FEATURE:
<221> NAME/KEY: MOD_RES
<222> LOCATION: (19)..(19)
<223> OTHER INFORMATION: D, Y or G
<220> FEATURE:
<221> NAME/KEY: MOD_RES
<222> LOCATION: (20)..(20)
<223> OTHER INFORMATION: Y, W, G or A
<220> FEATURE:
<221> NAME/KEY: MOD_RES
<222> LOCATION: (21)..(21)
<223> OTHER INFORMATION: M or F
<220> FEATURE:
<221> NAME/KEY: MOD_RES
<222> LOCATION: (23)..(23)
<223> OTHER INFORMATION: P, Y or V

<400> SEQUENCE: 24

Xaa Xaa Xaa Xaa Xaa Xaa Xaa Xaa Xaa Xaa Xaa Xaa Xaa Xaa Xaa Xaa
1               5                   10                  15

Xaa Tyr Xaa Xaa Xaa Asp Xaa
            20

<210> SEQ ID NO 25
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: R, D, G or V
<220> FEATURE:
<221> NAME/KEY: MOD_RES
<222> LOCATION: (2)..(2)
<223> OTHER INFORMATION: R, D, P, Y, S, G or L
<220> FEATURE:
<221> NAME/KEY: MOD_RES
<222> LOCATION: (3)..(3)
<223> OTHER INFORMATION: R, P, Y, T, G, A, F or V
<220> FEATURE:
<221> NAME/KEY: MOD_RES
<222> LOCATION: (4)..(4)
<223> OTHER INFORMATION: R, Y, G or I
<220> FEATURE:
<221> NAME/KEY: MOD_RES
<222> LOCATION: (5)..(5)
<223> OTHER INFORMATION: D, Y, S, G or M
<220> FEATURE:
<221> NAME/KEY: MOD_RES
<222> LOCATION: (6)..(6)
<223> OTHER INFORMATION: D, Y, S, G, V or I
<220> FEATURE:
<221> NAME/KEY: MOD_RES
<222> LOCATION: (7)..(7)
<223> OTHER INFORMATION: R, D, Y, S, G or V
<220> FEATURE:
<221> NAME/KEY: MOD_RES
<222> LOCATION: (8)..(8)
<223> OTHER INFORMATION: D, S, G, M or V
<220> FEATURE:
<221> NAME/KEY: MOD_RES
<222> LOCATION: (9)..(9)
<223> OTHER INFORMATION: Y, S, G, L or V
<220> FEATURE:
<221> NAME/KEY: MOD_RES
<222> LOCATION: (10)..(10)
<223> OTHER INFORMATION: Y, S, G or V
<220> FEATURE:
<221> NAME/KEY: MOD_RES
<222> LOCATION: (11)..(11)
```

```
<223> OTHER INFORMATION: R, Y, W, S, T, G or A
<220> FEATURE:
<221> NAME/KEY: MOD_RES
<222> LOCATION: (12)..(12)
<223> OTHER INFORMATION: Y, S or G
<220> FEATURE:
<221> NAME/KEY: MOD_RES
<222> LOCATION: (13)..(13)
<223> OTHER INFORMATION: Y, S, G, L or V
<220> FEATURE:
<221> NAME/KEY: MOD_RES
<222> LOCATION: (14)..(14)
<223> OTHER INFORMATION: Y, S, G, A or V
<220> FEATURE:
<221> NAME/KEY: MOD_RES
<222> LOCATION: (15)..(15)
<223> OTHER INFORMATION: E, Y, S, G or V
<220> FEATURE:
<221> NAME/KEY: MOD_RES
<222> LOCATION: (16)..(16)
<223> OTHER INFORMATION: Y, G or V
<220> FEATURE:
<221> NAME/KEY: MOD_RES
<222> LOCATION: (17)..(17)
<223> OTHER INFORMATION: R, Y, S or G
<220> FEATURE:
<221> NAME/KEY: MOD_RES
<222> LOCATION: (18)..(18)
<223> OTHER INFORMATION: Y or G
<220> FEATURE:
<221> NAME/KEY: MOD_RES
<222> LOCATION: (20)..(20)
<223> OTHER INFORMATION: D, Y or G
<220> FEATURE:
<221> NAME/KEY: MOD_RES
<222> LOCATION: (21)..(21)
<223> OTHER INFORMATION: Y, W, G or A
<220> FEATURE:
<221> NAME/KEY: MOD_RES
<222> LOCATION: (22)..(22)
<223> OTHER INFORMATION: M or F
<220> FEATURE:
<221> NAME/KEY: MOD_RES
<222> LOCATION: (24)..(24)
<223> OTHER INFORMATION: P, Y or V

<400> SEQUENCE: 25

Xaa Xaa Xaa Xaa Xaa Xaa Xaa Xaa Xaa Xaa Xaa Xaa Xaa Xaa Xaa Xaa
1               5                   10                  15

Xaa Xaa Tyr Xaa Xaa Xaa Asp Xaa
            20

<210> SEQ ID NO 26
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: R, D, G or V
<220> FEATURE:
<221> NAME/KEY: MOD_RES
<222> LOCATION: (2)..(2)
<223> OTHER INFORMATION: R, D, P, Y, S, G or L
<220> FEATURE:
<221> NAME/KEY: MOD_RES
<222> LOCATION: (3)..(3)
<223> OTHER INFORMATION: R, P, Y, T, G, A, F or V
<220> FEATURE:
<221> NAME/KEY: MOD_RES
<222> LOCATION: (4)..(4)
<223> OTHER INFORMATION: R, Y, G or I
<220> FEATURE:
```

```
<221> NAME/KEY: MOD_RES
<222> LOCATION: (5)..(5)
<223> OTHER INFORMATION: D, Y, S, G or M
<220> FEATURE:
<221> NAME/KEY: MOD_RES
<222> LOCATION: (6)..(6)
<223> OTHER INFORMATION: D, Y, S, G, V or I
<220> FEATURE:
<221> NAME/KEY: MOD_RES
<222> LOCATION: (7)..(7)
<223> OTHER INFORMATION: R, D, Y, S, G or V
<220> FEATURE:
<221> NAME/KEY: MOD_RES
<222> LOCATION: (8)..(8)
<223> OTHER INFORMATION: D, S, G, M or V
<220> FEATURE:
<221> NAME/KEY: MOD_RES
<222> LOCATION: (9)..(9)
<223> OTHER INFORMATION: Y, S, G, L or V
<220> FEATURE:
<221> NAME/KEY: MOD_RES
<222> LOCATION: (10)..(10)
<223> OTHER INFORMATION: Y, S, G or V
<220> FEATURE:
<221> NAME/KEY: MOD_RES
<222> LOCATION: (12)..(12)
<223> OTHER INFORMATION: Y, S or G
<220> FEATURE:
<221> NAME/KEY: MOD_RES
<222> LOCATION: (13)..(13)
<223> OTHER INFORMATION: Y, S, G, L or V
<220> FEATURE:
<221> NAME/KEY: MOD_RES
<222> LOCATION: (14)..(14)
<223> OTHER INFORMATION: Y, S, G, A or V
<220> FEATURE:
<221> NAME/KEY: MOD_RES
<222> LOCATION: (15)..(15)
<223> OTHER INFORMATION: E, Y, S, G or V
<220> FEATURE:
<221> NAME/KEY: MOD_RES
<222> LOCATION: (17)..(17)
<223> OTHER INFORMATION: R, Y, S or G
<220> FEATURE:
<221> NAME/KEY: MOD_RES
<222> LOCATION: (18)..(18)
<223> OTHER INFORMATION: Y or G
<220> FEATURE:
<221> NAME/KEY: MOD_RES
<222> LOCATION: (20)..(20)
<223> OTHER INFORMATION: D, Y or G
<220> FEATURE:
<221> NAME/KEY: MOD_RES
<222> LOCATION: (21)..(21)
<223> OTHER INFORMATION: Y, W, G or A
<220> FEATURE:
<221> NAME/KEY: MOD_RES
<222> LOCATION: (22)..(22)
<223> OTHER INFORMATION: M or F
<220> FEATURE:
<221> NAME/KEY: MOD_RES
<222> LOCATION: (24)..(24)
<223> OTHER INFORMATION: P, Y or V

<400> SEQUENCE: 26

Xaa Xaa Xaa Xaa Xaa Xaa Xaa Xaa Xaa Xaa Cys Xaa Xaa Xaa Xaa Cys
1               5                   10                  15

Xaa Xaa Tyr Xaa Xaa Xaa Asp Xaa
            20
```

PHAGE DISPLAY LIBRARY, MEMBERS THEREOF AND USES OF THE SAME

CROSS-REFERENCE TO RELATED APPLICATIONS

This application is a U.S. National Stage application of International Application No. PCT/EP2016/059713, filed on Apr. 29, 2016, said International Application No. PCT/EP2016/059713 claims benefit under 35 U.S.C. § 119(e) of the U.S. Provisional Application No. 62/155,646, filed May 1, 2015. Each of the above listed applications is incorporated by reference herein in its entirety for all purposes.

The instant application contains a Sequence Listing which has been filed electronically in ASCII format and is hereby incorporated by reference in its entirety. Said ASCII copy, created on Oct. 17, 2019, is named EG3-100-US-PCT_SL.txt and is 47,502 bytes in size.

The present invention relates to a library (in particular a phage display library) from which an improved human antibody having greater specificity and potency for its target may be generated; and to methods of generating such a human antibody. In particular, the invention relates to a human antibody to a challenging target.

Phage display technology is well known in the art, and is disclosed e.g. in McCafferty et al. Nature 348 (1990): 552-554 (incorporated herein by reference) and in WO 1993/11236 (incorporated herein by reference). However, it is also known within the art that generating functional human antibodies (i.e. antibodies which bind with a high specificity and/or potency) to particular targets represents something of a challenge (see Hutchings et al. (2010) MAbs 2(6): 594-606; Wilkinson et al. (2015) J Biomol Screen 20(4):454-467; and Smith (2015) J Biomol Screen 20(4): 437-453; each of which is incorporated herein by reference). Such challenging targets are considered to be more difficult to generate functional antibodies against than conventional soluble targets and simple receptors. Challenging targets include e.g. integral membrane proteins (such as ion channels, transporter proteins, G-protein coupled receptors or GPCRs) and viral proteins (such as viral capsid proteins).

Generating a functional human antibody to such a target from a conventional library such as a phage display library can involve the screening of tens of thousands of possible antibodies in order to find two or three possible antibodies with the appropriate functionality. This obviously represents a significant investment of time and other resources. At present, of the antibodies currently approved for human use worldwide (more than 30), only one is to a GPCR (mogamulizumab, an anti-CCR4 mAb approved in Japan), only one (palivizumab) is to a viral target and there are none to ion channels or transporters.

There is a need for functional antibodies which bind to such challenging targets. There is a need for improved libraries which require less screening in order to obtain such antibodies. There is a need for improved methods of generating such antibodies which can be carried out in a less resource-intensive manner.

The present invention meets one or more of the above needs by providing a phage library displaying human scFv, wherein at least 50% of the human scFv variable heavy chain CDR3 (CDR H3) displayed by the library is at least 18 amino acids in length.

The proportion of the human scFv variable heavy chain CDR H3 displayed by the library that is at least 18 amino acids in length may be at least 60%. The proportion of the human scFv variable heavy chain CDR H3 displayed by the library that is at least 18 amino acids in length may be at least 70%. The proportion of the human scFv variable heavy chain CDR H3 displayed by the library that is at least 18 amino acids in length may be at least 80%. The proportion of the human scFv variable heavy chain CDR H3 displayed by the library that is at least 18 amino acids in length may be at least 90%.

The preferred CDR H3 variable heavy chain displayed by the library of the invention is at least 18 amino acids in length. The CDR H3 variable heavy chain may be between 18 to 30 amino acids in length. The CDR H3 variable heavy chain may be between 20 to 30 amino acids in length. The CDR H3 variable heavy chain may be between 20 to 24 amino acids in length. As set out below, the CDR H3 variable heavy chain of the invention that is exemplified by this disclosure is between 20 to 24 amino acids in length.

It is known that definition of the amino acids which make up a particular CDR may vary depending on the method used; e.g. a CDR defined according to Kabat may comprise a different number of amino acids than if it were defined according to IMGT. Unless otherwise specifically indicated, the amino acid lengths set out herein are as defined by Kabat numbering.

Conventional human antibodies have a heavy chain CDR H3 that is on average around 12 to 13 amino acids in length, with a normal distribution around this mean. Human antibodies having a longer loop heavy chain CDR H3 are however known in the art and are disclosed inter alia in Spindler et al. (PLOS Pathogens (2014) Vol 10 Issue 10 e1004377), Burton et al. (PNAS (2005) Vol 102 No. 42 14943-14948), Corti & Lanzavecchia (Annu. Rev. Immunol (2013) 31: 705-742), Whittle et al. (PNAS (2011) Vol 108 No. 34 14216-14221) and Collis et al. (J. Mol. Biol. (2003) 325, 337-354), each of which is incorporated herein by reference. Collis et al. determined that the (normally distributed) mean length of a human CDR H3 is between 10 and 12 amino acids, except when the target is a virus, when the mean human CDR H3 length is around 16 amino acids.

Without being bound by any theory, the present inventors propose that a human antibody having a longer CDR H3 than is conventional will be more likely to have high specificity and/or potency for particular targets that contain, for instance, a pore, hydrophobic pocket or canyon structure. Thus, the present inventors have attempted to obtain such antibodies from existing phage display libraries such as those described in Vaughan et al., (1996) and Lloyd et al., (2009) but have found that this is hampered by the fact that such libraries display no more than 5% of the human CDR H3 having a length of 20 amino acids or more. The present inventors accordingly have generated a novel library in which the majority of human CDR H3 displayed by the library is at least 18 amino acids in length.

The library is initially generated from a human germline sequence of an antibody having a CDR H3 that is at least 18 amino acids in length. The library may be generated from the human germline sequence of any known such antibody, including the long CDR H3 antibodies disclosed in the cited references above. The library may be generated from a human germline sequence of an anti-FPR1 antibody that contains a CDR H3 that is at least 18 amino acids in length. The human anti-FPR1 antibody may contain a CDR H3 that is 24 amino acids in length. The human anti-FPR1 antibody may be FPRO165, as described in Douthwaite et al. (MAbs (2015) 7(1):152-166; incorporated herein by reference).

The present inventors propose that a human antibody generated from the library of the invention will be more likely to bind to, and functionally affect, difficult or challenging target antigens (e.g. antagonise or agonise them). Accordingly the invention provides the use of the library of the invention to generate a functional human antibody (i.e. a human antibody having high specificity and/or potency) to a challenging target. The invention further provides a method of generating a human antibody that will bind to a challenging target, the method comprising the steps of isolating a human antibody specific for the target from the library of the invention. The use of a phage display library to obtain an antibody is a matter of routine for a person of ordinary skill in the art. A sample protocol is exemplified below.

Challenging targets for antibodies are known within the art and include integral membrane proteins (such as ion channels, transporter proteins, GPCR) and viral capsid proteins (which often have hydrophobic canyons in their structure). Thus the human antibody generated from the library of the invention may be specific for a membrane protein. The human antibody generated from the library of the invention may be specific for an ion channel. The human antibody generated from the library of the invention may be specific for a transporter protein. The human antibody generated from the library of the invention may be specific for a GPCR. The human antibody generated from the library of the invention may be specific for a viral capsid protein.

The invention further provides a human antibody having a CDR H3 that is at least 18 amino acids in length. The human antibody of the invention may be obtainable from the library of the invention. Thus the human antibody may be obtained by the use or the method of the invention as defined above. The CDR3 H3 may be between 18 to 30 amino acids in length. The CDR3 H3 may be between 20 to 30 amino acids in length. The CDR3 H3 may be between 20 to 24 amino acids in length. The human antibody of the invention may bind to a challenging target, as defined above. The human antibody of the invention does not have a CDR H3 sequence as disclosed in any of Spindler et al. (PLOS Pathogens (2014) Vol 10 Issue 10 e1004377), Burton et al. (PNAS (2005) Vol 102 No. 42 14943-14948), Corti & Lanzavecchia (Annu. Rev. Immunol (2013) 31: 705-742), Whittle et al. (PNAS (2011) Vol 108 No. 34 14216-14221) and Collis et al. (J. Mol. Biol. (2003) 325, 337-354).

The human antibody of the invention may be an agonist or an antagonist. The human antibody of the invention may have a potency (IC50) of less than 50 nanoMolar for its target. The human antibody of the invention may have a potency (IC50) of less than 20 nanoMolar for its target. The human antibody of the invention may have a potency (IC50) of less than 10 nanoMolar for its target.

The human antibody of the invention may be a monoclonal antibody. For the avoidance of doubt, the term "antibody" explicitly includes such antigen-binding fragments. Thus, the human antibody of the invention may be an antigen-binding fragment thereof, such as a Fab, Fab', F(ab)2, Fv, or scFv.

The present inventors have analysed the amino acid composition of a human antibody of the invention having a CDR H3 of between 20 and 24 amino acids in length. The results are as set out in the Tables below.

Thus, based on the information provided within the Tables, it is evident that a CDR H3 of the library or the human antibody of the invention may be 20 amino acids in length and comprise the following amino acid sequences (SEQ ID NO: 15):
position 1: selected from the list consisting of: R, K, D, E, P, S, G, A, V
position 2: selected from the list consisting of: R, D, E, H, P, Y, S, G, F, L, V
position 3: selected from the list consisting of: R, D, H, P, Y, S, T, G, A, F, V
position 4: selected from the list consisting of: R, K, D, H, P, Y, W, S, G, A, F, L, V, I
position 5: selected from the list consisting of: K, D, H, P, Y, S, T, G, A, M, L, V, I
position 6: selected from the list consisting of: D, P, Y, S, G, A, M, F, L, V, I
position 7: selected from the list consisting of: R, K, D, E, P, Y, S, T, G, F, V, I
position 8: selected from the list consisting of: R, D, P, Y, S, T, G, A, M, F, L, V, I
position 9: selected from the list consisting of: R, D, P, Y, W, S, T, G, A, M, F, L, V, I
position 10: selected from the list consisting of: R, D, P, Y, S, T, G, A, M, F, L, V, I
position 11: selected from the list consisting of: R, D, E, P, Y, S, T, G, A, F, L, V, I
position 12: selected from the list consisting of: R, K, D, E, P, Y, S, T, G, A, F, L, V, I
position 13: selected from the list consisting of: R, K, D, E, P, Y, S, T, G
position 14: selected from the list consisting of: R, K, E, P, Y, S, T, G, A
position 15: selected from the list consisting of: R, E, P, Y, S, T, G, A, F, L, V
position 16: selected from the list consisting of: D, Y, S, T, G, F, L
position 17: selected from the list consisting of: Y, W, G, A
position 18: selected from the list consisting of: P, M, F, L
position 19: D
position 20: selected from the list consisting of: P, Y, L, V, I Alternatively, based on the information provided within the Tables, it is evident that a CDR H3 of the library or the human antibody of the invention may be 21 amino acids in length and comprise the following amino acid sequences (SEQ ID NO: 16):
position 1: selected from the list consisting of: R, K, D, E, P, S, G, A, V
position 2: selected from the list consisting of: R, D, E, H, P, Y, S, G, F, L, V
position 3: selected from the list consisting of: R, D, H, P, Y, S, T, G, A, F, V
position 4: selected from the list consisting of: R, K, D, H, P, Y, W, S, G, A, F, L, V, I
position 5: selected from the list consisting of: K, D, H, P, Y, S, T, G, A, M, L, V, I
position 6: selected from the list consisting of: D, P, Y, S, G, A, M, F, L, V, I
position 7: selected from the list consisting of: R, K, D, E, P, Y, S, T, G, F, V, I
position 8: selected from the list consisting of: R, D, P, Y, W, S, T, G, A, M, F, L, V, I
position 9: selected from the list consisting of: R, D, P, Y, W, S, T, G, A, F, L, V, I
position 10: selected from the list consisting of: R, D, E, P, Y, W, S, G, A, L, V, I
position 11: selected from the list consisting of: R, D, P, Y, S, T, G, A, M, F, L, V, I
position 12: selected from the list consisting of: R, D, E, P, Y, S, T, G, A, F, L, V, I position 13: selected from the list consisting of: R, K, D, E, P, Y, S, T, G, A, F, L, V, I
position 14: selected from the list consisting of: R, K, D, E, P, Y, S, T, G
position 15: selected from the list consisting of: R, K, E, P, Y, S, T, G, A
position 16: selected from the list consisting of: R, E, P, Y, S, T, G, A, F, L, V
position 17: selected from the list consisting of: D, Y, S, T, G, F, L
position 18: selected from the list consisting of: Y, W, G, A
position 19: selected from the list consisting of: P, M, F, L
position 20: D
position 21: selected from the list consisting of: P, Y, L, V, I Alternatively, based on the information provided within the Tables, it is evident that a CDR H3 of the library or the human antibody of the invention may be 22 amino acids in length and comprise the following amino acid sequences (SEQ ID NO: 17):
position 1: selected from the list consisting of: R, K, D, E, P, S, G, A, V
position 2: selected from the list consisting of: R, D, E, H, P, Y, S, G, F, L, V
position 3: selected from the list consisting of: R, D, H, P, Y, S, T, G, A, F, V
position 4: selected from the list consisting of: R, K, D, H, P, Y, W, S, G, A, F, L, V, I
position 5: selected from the list consisting of: K, D, H, P, Y, S, T, G, A, M, L, V, I
position 6: selected from the list consisting of: D, P, Y, S, G, A, M, F, L, V, I
position 7: selected from the list consisting of: R, K, D, E, P, Y, S, T, G, F, V, I
position 8: selected from the list consisting of: R, D, P, Y, S, T, G, A, M, F, L, V, I
position 9: selected from the list consisting of: R, D, P, Y, W, S, T, G, A, M, F, L, V, I
position 10: selected from the list consisting of: R, D, P, Y, W, S, T, G, A, F, L, V, I
position 11: selected from the list consisting of: R, D, E, P, Y, W, S, G, A, L, V, I
position 12: selected from the list consisting of: R, D, P, Y, S, T, G, A, M, F, L, V, I
position 13: selected from the list consisting of: R, D, E, P, Y, S, T, G, A, F, L, V, I
position 14: selected from the list consisting of: R, K, D, E, P, Y, S, T, G, A, F, L, V, I
position 15: selected from the list consisting of: R, K, D, E, P, Y, S, T, G
position 16: selected from the list consisting of: R, K, E, P, Y, S, T, G, A
position 17: selected from the list consisting of: R, E, P, Y, S, T, G, A, F, L, V
position 18: selected from the list consisting of: D, Y, S, T, G, F, L
position 19: selected from the list consisting of: Y, W, G, A
position 20: selected from the list consisting of: P, M, F, L
position 21: D
position 22: selected from the list consisting of: P, Y, L, V, I Alternatively, based on the information provided within the Tables, it is evident that a CDR H3 of the library or the human antibody of the invention may be 23 amino acids in length and comprise the following amino acid sequences (SEQ ID NO: 18):
position 1: selected from the list consisting of: R, K, D, E, P, S, G, A, V
position 2: selected from the list consisting of: R, D, E, H, P, Y, S, G, F, L, V
position 3: selected from the list consisting of: R, D, H, P, Y, S, T, G, A, F, V
position 4: selected from the list consisting of: R, K, D, H, P, Y, W, S, G, A, F, L, V, I
position 5: selected from the list consisting of: K, D, H, P, Y, S, T, G, A, M, L, V, I
position 6: selected from the list consisting of: D, P, Y, S, G, A, M, F, L, V, I
position 7: selected from the list consisting of: R, K, D, E, P, Y, S, T, G, F, V, I
position 8: selected from the list consisting of: R, D, P, Y, W, S, T, G, A, M, F, L, V, I
position 9: selected from the list consisting of: R, D, P, Y, W, S, T, G, A, F, L, V, I
position 10: selected from the list consisting of: R, D, Q, P, Y, W, S, T, G, A
position 11: selected from the list consisting of: K, Q, E, H, Y, W, S, T, G, A, F, L, I
position 12: selected from the list consisting of: R, D, E, P, Y, W, S, G, A, L, V, I
position 13: selected from the list consisting of: R, D, P, Y, S, T, G, A, M, F, L, V, I
position 14: selected from the list consisting of: R, D, E, P, Y, S, T, G, A, F, L, V, I
position 15: selected from the list consisting of: R, K, D, E, P, Y, S, T, G, A, F, L, V, I
position 16: selected from the list consisting of: R, K, D, E, P, Y, S, T, G
position 17: selected from the list consisting of: R, K, E, P, Y, S, T, G, A
position 18: selected from the list consisting of: R, E, P, Y, S, T, G, A, F, L, V
position 19: selected from the list consisting of: D, Y, S, T, G, F, L
position 20: selected from the list consisting of: Y, W, G, A
position 21: selected from the list consisting of: P, M, F, L
position 22: D
position 23: selected from the list consisting of: P, Y, L, V, I Alternatively, based on the information provided within the Tables, it is evident that a CDR H3 of the library or the human antibody of the invention may be 24 amino acids in length and comprise the following amino acid sequences (SEQ ID NO: 19):
position 1: selected from the list consisting of: R, K, D, E, P, S, G, A, V
position 2: selected from the list consisting of: R, D, E, H, P, Y, S, G, F, L, V
position 3: selected from the list consisting of: R, D, H, P, Y, S, T, G, A, F, V
position 4: selected from the list consisting of: R, K, D, H, P, Y, W, S, G, A, F, L, V, I
position 5: selected from the list consisting of: K, D, H, P, Y, S, T, G, A, M, L, V, I
position 6: selected from the list consisting of: D, P, Y, S, G, A, M, F, L, V, I
position 7: selected from the list consisting of: R, K, D, E, P, Y, S, T, G, F, V, I position 8: selected from the list consisting of: R, D, P, Y, S, T, G, A, M F, L, V, I
position 9: selected from the list consisting of: R, D, P, Y, W, S, T, G, A, M, F, L, V, I
position 10: selected from the list consisting of: R, D, P, Y, W, S, T, G, A, F, L, V, I
position 11: selected from the list consisting of: R, D, Q, P, Y, W, S, T, G, A
position 12: selected from the list consisting of: K, Q, E, H, Y, W, S, T, G, A, F, L, I
position 13: selected from the list consisting of: R, D, E, P, Y, W, S, G, A, L, V, I
position 14: selected from the list consisting of: R, D, P, Y, S, T, G, A, M, F, L, V, I
position 15: selected from the list consisting of: R, D, E, P, Y, S, T, G, A, F, L, V, I
position 16: selected from the list consisting of: R, K, D, E, P, Y, S, T, G, A, F, L, V, I
position 17: selected from the list consisting of: R, K, D, E, P, Y, S, T, G
position 18: selected from the list consisting of: R, K, E, P, Y, S, T, G, A
position 19: selected from the list consisting of: R, E, P, Y, S, T, G, A, F, L, V
position 20: selected from the list consisting of: D, Y, S, T, G, F, L
position 21: selected from the list consisting of: Y, W, G, A
position 22: selected from the list consisting of: P, M, F, L
position 23: D
position 24: selected from the list consisting of: P, Y, L, V, I Alternatively, based on the information provided within the Tables, it is evident that a CDR H3 of the library or the human antibody of the invention may be 24 amino acids in length and comprise the following amino acid sequences (SEQ ID NO: 20):
position 1: selected from the list consisting of: R, K, D, E, P, S, G, A, V
position 2: selected from the list consisting of: R, D, E, H, P, Y, S, G, F, L, V
position 3: selected from the list consisting of: R, D, H, P, Y, S, T, G, A, F, V
position 4: selected from the list consisting of: R, K, D, H, P, Y, W, S, G, A, F, L, V, I
position 5: selected from the list consisting of: K, D, H, P, Y, S, T, G, A, M, L, V, I
position 6: selected from the list consisting of: D, P, Y, S, G, A, M, F, L, V, I
position 7: selected from the list consisting of: R, K, D, E, P, Y, S, T, G, F, V, I
position 8: selected from the list consisting of: R, D, P, Y, S, T, G, A, M F, L, V, I
position 9: selected from the list consisting of: R, D, P, Y, W, S, T, G, A, M, F, L, V, I
position 10: selected from the list consisting of: R, D, P, Y, W, S, T, G, A, F, L, V, I
position 11: C
position 12: selected from the list consisting of: K, Q, E, H, Y, W, S, T, G, A, F, L, I
position 13: selected from the list consisting of: R, D, E, P, Y, W, S, G, A, L, V, I
position 14: selected from the list consisting of: R, D, P, Y, S, T, G, A, M, F, L, V, I
position 15: selected from the list consisting of: R, D, E, P, Y, S, T, G, A, F, L, V, I
position 16: C
position 17: selected from the list consisting of: R, K, D, E, P, Y, S, T, G
position 18: selected from the list consisting of: R, K, E, P, Y, S, T, G, A
position 19: selected from the list consisting of: R, E, P, Y, S, T, G, A, F, L, V
position 20: selected from the list consisting of: D, Y, S, T, G, F, L
position 21: selected from the list consisting of: Y, W, G, A
position 22: selected from the list consisting of: P, M, F, L
position 23: D
position 24: selected from the list consisting of: P, Y, L, V, I The information from the Tables below may reasonably be generalised: thus, for example the amino acids at position 1 are selected from R, K, D, E, P, S, G, A and V irrespective of whether the CDR H3 is 20, 21, 22, 23 or 24 amino acids in length. It is therefore reasonable to infer that the human antibody of the invention will have an amino acid at position 1 that is selected from R, K, D, E, P, S, G, A and V. The same may be inferred for position 2 (i.e. the amino acids will be selected from the list consisting of: R, D, E, H, P, Y, S, G, F, L, V); position 3 (i.e. the amino acids will be selected from the list consisting of: R, D, H, P, Y, S, T, G, A, F, V); position 4 (i.e. the amino acids will be selected from the list consisting of: R, K, D, H, P, Y, W, S, G, A, F, L, V, I); position 5 (i.e. the amino acids will be selected from the list consisting of: K, D, H, P, Y, S, T, G, A, M, L, V, I); position 6 (i.e. the amino acids will be selected from the list consisting of: D, P, Y, S, G, A, M, F, L, V, I); and position 7 (i.e. the amino acids will be selected from the list consisting of: R, K, D, E, P, Y, S, T, G, F, V, I).

As set out in Tables 6 to 11 below, the present inventors have assigned percentage numbers (accurate to within ±1.5%) for the presence of each amino acid at a particular position of the human antibody of the invention. Assigning a cut-off point of 10% or more, a particular human antibody of the invention having a CDR H3 of 20 amino acids in length may comprise the following amino acid sequences (SEQ ID NO: 21):
position 1: selected from the list consisting of R, D, G, V
position 2: selected from the list consisting of R, D, P, Y, S, G, L
position 3: selected from the list consisting of: R, P, Y, T, G, A, F, V
position 4: selected from the list consisting of: R, Y, G, I
position 5: selected from the list consisting of: D, Y, S, G, M
position 6: selected from the list consisting of: D, Y, S, G, V, I
position 7: selected from the list consisting of: R, D, Y, S, G, V
position 8: selected from the list consisting of: D, S, G, M, V
position 9: selected from the list consisting of: Y, S, T, G, L, V
position 10: selected from the list consisting of: Y, S, G, A, V
position 11: selected from the list consisting of: E, Y, S, G, V
position 12: selected from the list consisting of: Y, G, V
position 13: selected from the list consisting of: R, Y, S, G
position 14: selected from the list consisting of: Y, G position 15: selected from the list consisting of: Y
position 16: selected from the list consisting of: D, Y, G
position 17: selected from the list consisting of: Y, W, G, A
position 18: selected from the list consisting of: M, F
position 19: D
position 20: selected from the list consisting of: P, Y, V Alternatively, assigning a cut-off point of 10% or more, a CDR H3 of the library or the human antibody of the invention may be 21 amino acids in length and comprise the following amino acid sequences (SEQ ID NO: 22):
position 1: selected from the list consisting of: R, D, G, V
position 2: selected from the list consisting of: R, D, P, Y, S, G, L
position 3: selected from the list consisting of: R, P, Y, T, G, A, F, V
position 4: selected from the list consisting of: R, Y, G, I
position 5: selected from the list consisting of: D, Y, S, G, M
position 6: selected from the list consisting of: D, Y, S, G, V, I
position 7: selected from the list consisting of: R, D, Y, S, G, V
position 8: selected from the list consisting of: Y, S, G, L, V
position 9: selected from the list consisting of: Y, S, G, V
position 10: selected from the list consisting of: Y, S, G, L, V
position 11: selected from the list consisting of: Y, S, G, A, V
position 12: selected from the list consisting of: E, Y, S, G, V
position 13: selected from the list consisting of: Y, G, V
position 14: selected from the list consisting of: R, Y, S, G
position 15: selected from the list consisting of: Y, G
position 16: Y
position 17: selected from the list consisting of: D, Y, G
position 18: selected from the list consisting of: Y, W, G, A
position 19: selected from the list consisting of: M, F
position 20: D
position 21: selected from the list consisting of: P, Y, V Alternatively, assigning a cut-off point of 10% or more, a CDR H3 of the library or the human antibody of the invention may be 22 amino acids in length and comprise the following amino acid sequences (SEQ ID NO: 23):
position 1: selected from the list consisting of: R, D, G, V
position 2: selected from the list consisting of: R, D, P, Y, S, G, L
position 3: selected from the list consisting of: R, P, Y, T, G, A, F, V
position 4: selected from the list consisting of: R, Y, G, I
position 5: selected from the list consisting of: D, Y, S, G, M
position 6: selected from the list consisting of: D, Y, S, G, V, I
position 7: selected from the list consisting of: R, D, Y, S, G, V
position 8: selected from the list consisting of: D, S, G, M, V
position 9: selected from the list consisting of: Y, S, G, L, V
position 10: selected from the list consisting of: Y, S, G, V
position 11: selected from the list consisting of: Y, S, G, L, V
position 12: selected from the list consisting of: Y, S, G, A, V
position 13: selected from the list consisting of: E, Y, S, G, V
position 14: selected from the list consisting of: Y, G, V
position 15: selected from the list consisting of: R, Y, S, G
position 16: selected from the list consisting of: Y, G
position 17: Y
position 18: selected from the list consisting of: D, Y, G
position 19: selected from the list consisting of: Y, W, G, A
position 20: selected from the list consisting of: M, F
position 21: D
position 22: selected from the list consisting of: P, Y, V Alternatively, assigning a cut-off point of 10% or more, a CDR H3 of the library or the human antibody of the invention may be 23 amino acids in length and comprise the following amino acid sequences (SEQ ID NO: 24):
position 1: selected from the list consisting of: R, D, G, V
position 2: selected from the list consisting of: R, D, P, Y, S, G, L
position 3: selected from the list consisting of: R, P, Y, T, G, A, F, V
position 4: selected from the list consisting of: R, Y, G, I
position 5: selected from the list consisting of: D, Y, S, G, M
position 6: selected from the list consisting of: D, Y, S, G, V, I
position 7: selected from the list consisting of: R, D, Y, S, G, V
position 8: selected from the list consisting of: Y, S, G, L, V
position 9: selected from the list consisting of: Y, S, G, V
position 10: selected from the list consisting of: R, Y, W, S, T, G, A
position 11: selected from the list consisting of: Y, S, G
position 12: selected from the list consisting of: Y, S, G, L, V
position 13: selected from the list consisting of: Y, S, G, A, V
position 14: selected from the list consisting of: E, Y, S, G, V
position 15: selected from the list consisting of: Y, G, V
position 16: selected from the list consisting of: R, Y, S, G
position 17: selected from the list consisting of: Y, G
position 18: Y
position 19: selected from the list consisting of: D, Y, G
position 20: selected from the list consisting of: Y, W, G, A
position 21: selected from the list consisting of: M, F
position 22: D
position 23: selected from the list consisting of: P, Y, V Alternatively, assigning a cut-off point of 10% or more, a CDR H3 of the library or the human antibody of the invention may be 24 amino acids in length and comprise the following amino acid sequences (SEQ ID NO: 25):
position 1: selected from the list consisting of: R, D, G, V
position 2: selected from the list consisting of: R, D, P, Y, S, G, L
position 3: selected from the list consisting of: R, P, Y, T, G, A, F, V
position 4: selected from the list consisting of: R, Y, G, I
position 5: selected from the list consisting of: D, Y, S, G, M position 6: selected from the list consisting of: D, Y, S, G, V, I
position 7: selected from the list consisting of: R, D, Y, S, G, V
position 8: selected from the list consisting of: D, S, G, M V
position 9: selected from the list consisting of: Y, S, G, L, V
position 10: selected from the list consisting of: Y, S, G, V
position 11: selected from the list consisting of: R, Y, W, S, T, G, A
position 12: selected from the list consisting of: Y, S, G
position 13: selected from the list consisting of: Y, S, G, L, V
position 14: selected from the list consisting of: Y, S, G, A, V
position 15: selected from the list consisting of: E, Y, S, G, V
position 16: selected from the list consisting of: Y, G, V
position 17: selected from the list consisting of: R, Y, S, G
position 18: selected from the list consisting of: Y, G
position 19: Y
position 20: selected from the list consisting of: D, Y, G
position 21: selected from the list consisting of: Y, W, G, A
position 22: selected from the list consisting of: M, F
position 23: D
position 24: selected from the list consisting of: P, Y, V Alternatively, assigning a cut-off point of 10% or more, a CDR H3 of the library or the human antibody of the invention may be 24 amino acids in length and comprise the following amino acid sequences (SEQ ID NO: 26):
position 1: selected from the list consisting of: R, D, G, V
position 2: selected from the list consisting of: R, D, P, Y, S, G, L
position 3: selected from the list consisting of: R, P, Y, T, G, A, F, V
position 4: selected from the list consisting of: R, Y, G, I
position 5: selected from the list consisting of: D, Y, S, G, M
position 6: selected from the list consisting of: D, Y, S, G, V, I
position 7: selected from the list consisting of: R, D, Y, S, G, V
position 8: selected from the list consisting of: D, S, G, M V
position 9: selected from the list consisting of: Y, S, G, L, V
position 10: selected from the list consisting of: Y, S, G, V
position 11: C
position 12: selected from the list consisting of: Y, S, G
position 13: selected from the list consisting of: Y, S, G, L, V
position 14: selected from the list consisting of: Y, S, G, A, V
position 15: selected from the list consisting of: E, Y, S, G, V
position 16: C
position 17: selected from the list consisting of: R, Y, S, G
position 18: selected from the list consisting of: Y, G
position 19: Y
position 20: selected from the list consisting of: D, Y, G
position 21: selected from the list consisting of: Y, W, G, A
position 22: selected from the list consisting of: M, F
position 23: D
position 24: selected from the list consisting of: P, Y, V

DESCRIPTION OF THE FIGURES

The present invention will now be described by way of example with reference to the following Figures, in which are shown:

FIG. 1: An X-ray crystal structure of a Fab fragment of the anti-FPR antibody (FPRO165) on which the phage display library is based, indicating that the long VH CDR loop is sufficiently stable for structural elucidation FIG. 2: Schematic of VH insert design for long VH CDR3 library. Six constructs representing VH CDR lengths 20-24, plus a 24 amino acid length construct encoding cysteines at loop positions 11 and 16 were synthesised. The six different CDR3 inserts were designed with amino acid compositions as defined in Tables 6-11 (FIG. 2 discloses SEQ ID NOS: 1-6, respectively, in order of appearance)

FIG. 3: Analysis of cloning efficiency of the 6 VH long CDR3 repertoires. ScFv genes for 264-528 individual clones from each sub-library were sequenced to determine estimates of HCDR3 diversity and library quality. This analysis indicated that the library was highly diverse (100% diversity in HCDR3 sequence among sequenced clones) and that ~70% of the clones in each sub-library encode full-length, in-frame scFv.

FIG. 4: Deep sequencing analysis of the actual VH CDR3 loop lengths following cloning into phagemid vector containing antibody light chain repertoires. From 1.2-1.6 million individual reads per sub-library, the NGS (Next Generation Sequencing) indicates that 60-70% clones in each sub-library contain a VHCDR3 of the expected length. This analysis also confirmed that for the vast majority of the positions in each sub-library, amino acid usage in the final library was consistent (frequency of amino acid observed/designed=0.1-2) with the library design.

FIG. 5: Diversity of light chain germline usage following cloning of the 6 VH repertoire inserts. 100000 randomly chosen individual reads per sub-library were used to generate information about VL germline diversity. The three most frequently used VL germlines are IGLV1-44*01, IGV3-19*01 and IGLV1-40*01, each representing 7-10% of each sub-library. The most common kappa germline is IGKV3-20*01, representing 4-5% of each sub-library.

FIG. 6: VH (6a, 6b) and VL (6c, 6d) sequence for four anti-P2X4 antibodies (Antibody 1-4) obtained from the phage display library of the invention. FIG. 6 discloses SEQ ID NOS: 7-14, respectively, in order of appearance.

EXAMPLE 1

Design of a Long VH CDR 3 (CDR H3) Library

An anti-FPR1 antibody was described, that contains an unusually long VH CDR3 (24 amino acids by Kabat definition; 26 by IMGT definition; Douthwaite, JA et al., 2015; MAbs: 7(1): 152-166; incorporated herein by reference). An X-ray crystal structure of a Fab fragment of this antibody (FPRO165) indicated that the long VH CDR loop was sufficiently stable for structural elucidation (FIG. 1). FPRO165's heavy chain sequence most closely matches the VH3-15*07 gene, which is unusual in that instead of the common sequence of cysteine followed by alanine and then either arginine or lysine (CAR/K) at the beginning of VH CDR3, the gene encodes cysteine, followed by two threonines (CTT). Without being bound by any theory, the present inventors propose that this unusual structural feature at the base of this long VH CDR3 loop may provide some structural stability. It was therefore decided to use the germline gene VH3-15*07 as the basis of the heavy chain repertoire for an antibody library with long VH CDR3 loops.

Five VH CDR3 loop lengths were initially designed, of 20, 21, 22, 23 and 24 amino acids in length (as defined by Kabat numbering, i.e. the CDR3 loop is defined as starting at the amino acid immediately preceding the CTT motif in the VH germline sequence (Kabat numbering 92-94, with VH CDR3 beginning at Kabat position 95). In order to design diversity into the loops, an analysis of known human antibody sequences at given loop lengths was used (Zemlin M et al., 2003; J. Mol. Biol. 334(4): 733-749). The average percentage usage (in humans) for each amino acid was determined for each position along a VH CDR3 of a given loop length (Table 1-5).

The VH library repertoire was synthesised using cyclical enzymatic single codon synthesis (Colibra™, Isogenica Ltd, Little Chesterford, UK; EP 1907548, EP 2236612 and U.S. Pat. No. 8,357,638 B2 and Ashraf MA et al., 2013; Biochem. Soc. Trans. 41: 1189-1194). Technical limitations of this methodology entailed that the minimum % usage for each amino acid at a particular position that could be successfully synthesised was 5%. The VH repertoires for the library were therefore designed based upon a modified version of the amino acid compositions described in Zemlin et al. for loop lengths of 20-24 amino acids in length (Tables 6-10). An additional VH repertoire of 24 amino acids, containing a fixed pair of cysteines at positions 11 and 16 was also designed. Several human antibody D genes contain pairs of cysteine amino acids encoded in them. Without being bound by any theory, the present inventors propose that a disulphide pairing of the two cysteines in these positions might lead to increased structural stability of the VH CDR3 loop and so it was included in the design of this repertoire (Table 11). The C-terminal framework 4 region, directly downstream of the VH CDR3 is typically encoded by a human VHJ segment. In the case of the library design, this was restricted to a single sequence derived from VHJ segment IGHJ6*01, as this was used in the FPRO165 antibody used as a basis of the design of the library. The entire VH construct that was synthesised for each of the different loop lengths therefore consisted of VH framework 1 (FW1)-CDR1-FW2-CDR2-FW3-derived from the germline VH3-15*07, followed by the designed CDR3 sequence (Tables 6-11), followed by a single FW4 region (starting at tryptophan at Kabat defined position 103) derived from the IGHJ6*01 gene. In order to facilitate cloning of the insert into a phagemid vector, restriction sites for the restriction endonucleases NcoI and XhoI were designed into the construct upstream and downstream respectively. The overall design of the library is summarised in FIG. 2.

TABLE 1

Percentage usage of each amino acid at each position of VH CDR3 loops for known human antibodies of 20 amino acids in length as analysed in Zemlin et al., (2003)

| | Position on VH CDR3 length | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| R | 8 | 14 | 10 | 15 | 2 | 0 | 14 | 2 | 4 | 6 | 6 | 5 | 12 | 3 | 3 | 2 | 0 | 0 | 0 | 0 |
| K | 5 | 0 | 0 | 3 | 2 | 0 | 3 | 0 | 0 | 0 | 3 | 0 | 2 | 3 | 0 | 0 | 0 | 0 | 0 | 0 |
| N | 0 | 3 | 0 | 3 | 3 | 2 | 3 | 0 | 0 | 0 | 3 | 5 | 5 | 5 | 0 | 7 | 0 | 2 | 0 | 0 |
| D | 35 | 3 | 4 | 3 | 8 | 8 | 10 | 9 | 4 | 3 | 2 | 13 | 3 | 0 | 2 | 8 | 0 | 0 | 100 | 0 |
| Q | 0 | 3 | 2 | 0 | 0 | 0 | 2 | 0 | 2 | 2 | 0 | 0 | 0 | 3 | 0 | 0 | 0 | 0 | 0 | 0 |
| E | 5 | 3 | 3 | 3 | 0 | 0 | 3 | 0 | 0 | 10 | 4 | 2 | 3 | 3 | 2 | 0 | 0 | 0 | 0 | 0 |
| H | 2 | 3 | 5 | 3 | 4 | 2 | 0 | 2 | 0 | 2 | 3 | 2 | 0 | 2 | 6 | 0 | 3 | 0 | 0 | 4 |
| P | 2 | 12 | 13 | 3 | 5 | 4 | 2 | 5 | 4 | 0 | 4 | 3 | 5 | 6 | 6 | 0 | 0 | 5 | 0 | 8 |
| Y | 0 | 8 | 8 | 10 | 18 | 12 | 12 | 4 | 8 | 12 | 14 | 21 | 42 | 48 | 48 | 60 | 36 | 0 | 0 | 12 |
| W | 0 | 3 | 0 | 2 | 2 | 2 | 0 | 4 | 6 | 2 | 3 | 2 | 0 | 2 | 2 | 3 | 10 | 0 | 0 | 0 |
| S | 4 | 8 | 5 | 5 | 8 | 18 | 12 | 13 | 16 | 18 | 9 | 6 | 6 | 3 | 5 | 5 | 3 | 0 | 0 | 2 |
| T | 2 | 2 | 7 | 3 | 5 | 2 | 4 | 5 | 5 | 5 | 3 | 8 | 3 | 3 | 2 | 0 | 2 | 0 | 0 | 2 |
| G | 20 | 16 | 10 | 12 | 12 | 12 | 10 | 24 | 12 | 12 | 15 | 6 | 8 | 12 | 5 | 8 | 36 | 0 | 0 | 0 |
| A | 5 | 0 | 8 | 3 | 4 | 5 | 2 | 5 | 5 | 10 | 6 | 5 | 0 | 3 | 4 | 0 | 10 | 0 | 0 | 0 |
| M | 2 | 2 | 3 | 2 | 11 | 3 | 0 | 6 | 4 | 4 | 2 | 0 | 0 | 0 | 2 | 0 | 0 | 50 | 0 | 0 |
| C | 0 | 0 | 0 | 0 | 0 | 0 | 0 | 0 | 0 | 0 | 0 | 0 | 0 | 0 | 0 | 0 | 0 | 0 | 0 | 0 |
| F | 0 | 3 | 10 | 5 | 2 | 3 | 5 | 5 | 4 | 0 | 0 | 5 | 3 | 2 | 4 | 3 | 0 | 36 | 0 | 0 |
| L | 2 | 10 | 2 | 5 | 4 | 5 | 3 | 5 | 8 | 8 | 5 | 4 | 3 | 0 | 3 | 2 | 0 | 5 | 0 | 7 |
| V | 8 | 5 | 7 | 5 | 5 | 10 | 10 | 7 | 16 | 10 | 6 | 6 | 2 | 0 | 3 | 0 | 0 | 2 | 0 | 60 |
| I | 0 | 2 | 3 | 15 | 5 | 12 | 5 | 4 | 2 | 6 | 6 | 5 | 4 | 2 | 2 | 0 | 0 | 0 | 0 | 5 |
| n= | 100 | 100 | 100 | 100 | 100 | 100 | 100 | 100 | 100 | 100 | 100 | 100 | 100 | 100 | 100 | 100 | 100 | 100 | 100 | 100 |

TABLE 2

Percentage usage of each amino acid at each position of VH CDR3 loops for known human antibodies of 21 amino acids in length as analysed in Zemlin et al., (2003)

| | Position on VH CDR3 Length | | | | | | | | | | | | | | | | | | | | |
|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 |
| R | 0 | 12 | 8 | 2 | 4 | 8 | 2 | 6 | 4 | 0 | 12 | 6 | 6 | 12 | 8 | 4 | 2 | 4 | 0 | 0 | 0 |
| K | 0 | 4 | 2 | 2 | 0 | 0 | 0 | 0 | 0 | 0 | 0 | 0 | 2 | 4 | 0 | 0 | 0 | 0 | 0 | 0 | 0 |
| N | 2 | 2 | 4 | 2 | 4 | 2 | 0 | 4 | 0 | 0 | 2 | 5 | 6 | 4 | 2 | 0 | 4 | 0 | 0 | 0 | 2 |

TABLE 2-continued

Percentage usage of each amino acid at each position of VH CDR3 loops for known human antibodies of 21 amino acids in length as analysed in Zemlin et al., (2003)

Position on VH CDR3 Length

| | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| D | 38 | 6 | 4 | 10 | 10 | 10 | 6 | 4 | 8 | 0 | 2 | 8 | 14 | 3 | 6 | 2 | 8 | 0 | 0 | 100 | 0 |
| Q | 4 | 4 | 0 | 4 | 4 | 2 | 0 | 2 | 0 | 4 | 2 | 0 | 2 | 3 | 0 | 2 | 0 | 0 | 0 | 0 | 0 |
| E | 2 | 2 | 12 | 6 | 0 | 2 | 6 | 4 | 6 | 0 | 2 | 0 | 8 | 2 | 3 | 0 | 0 | 0 | 0 | 0 | 0 |
| H | 2 | 2 | 2 | 0 | 4 | 2 | 2 | 2 | 4 | 2 | 3 | 6 | 0 | 4 | 2 | 4 | 4 | 0 | 0 | 0 | 2 |
| P | 0 | 10 | 6 | 4 | 0 | 2 | 2 | 6 | 3 | 8 | 6 | 12 | 8 | 6 | 6 | 4 | 0 | 0 | 0 | 0 | 4 |
| Y | 2 | 4 | 5 | 20 | 30 | 14 | 14 | 5 | 10 | 14 | 20 | 6 | 18 | 34 | 55 | 60 | 66 | 22 | 0 | 0 | 12 |
| W | 0 | 0 | 5 | 0 | 2 | 4 | 6 | 10 | 3 | 12 | 4 | 0 | 2 | 2 | 0 | 0 | 2 | 6 | 0 | 0 | 0 |
| S | 2 | 10 | 8 | 12 | 10 | 15 | 20 | 16 | 16 | 20 | 10 | 8 | 10 | 8 | 2 | 6 | 2 | 0 | 2 | 0 | 0 |
| T | 2 | 6 | 2 | 8 | 2 | 0 | 4 | 3 | 6 | 4 | 2 | 8 | 6 | 4 | 2 | 2 | 2 | 0 | 0 | 0 | 2 |
| G | 18 | 18 | 10 | 10 | 10 | 15 | 10 | 12 | 18 | 20 | 12 | 16 | 8 | 4 | 6 | 4 | 5 | 48 | 0 | 0 | 0 |
| A | 2 | 2 | 10 | 2 | 4 | 4 | 2 | 6 | 3 | 2 | 6 | 6 | 2 | 0 | 2 | 0 | 0 | 8 | 0 | 0 | 0 |
| M | 2 | 0 | 4 | 0 | 0 | 0 | 2 | 0 | 0 | 0 | 0 | 0 | 4 | 0 | 0 | 0 | 0 | 0 | 58 | 0 | 0 |
| C | 0 | 0 | 0 | 0 | 0 | 0 | 0 | 0 | 0 | 0 | 0 | 0 | 0 | 0 | 0 | 0 | 0 | 0 | 0 | 0 | 0 |
| F | 0 | 4 | 0 | 0 | 2 | 8 | 10 | 5 | 6 | 2 | 0 | 5 | 2 | 2 | 2 | 6 | 0 | 2 | 30 | 0 | 4 |
| L | 6 | 6 | 10 | 12 | 4 | 2 | 0 | 5 | 6 | 6 | 6 | 4 | 0 | 6 | 4 | 6 | 5 | 6 | 8 | 0 | 4 |
| V | 16 | 4 | 6 | 4 | 6 | 6 | 10 | 8 | 4 | 4 | 8 | 8 | 2 | 0 | 0 | 0 | 0 | 4 | 0 | 0 | 64 |
| I | 2 | 4 | 2 | 2 | 4 | 4 | 4 | 2 | 3 | 2 | 3 | 2 | 0 | 2 | 0 | 0 | 0 | 0 | 2 | 0 | 6 |
| n= | 100 | 100 | 100 | 100 | 100 | 100 | 100 | 100 | 100 | 100 | 100 | 100 | 100 | 100 | 100 | 100 | 100 | 100 | 100 | 100 | 100 |

TABLE 3

Percentage usage of each amino acid at each position of VH CDR3 loops for known human antibodies of 22 amino acids in length as analysed in Zemlin et al., (2003)

Position on VH CDR3 Length

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| R | 3 | 12 | 17 | 12 | 4 | 6 | 0 | 5 | 5 | 5 | 2 | 2 | 10 | 8 | 8 | 8 | 3 | 0 | 3 | 0 | 0 | 0 |
| K | 2 | 7 | 7 | 2 | 4 | 0 | 0 | 0 | 4 | 0 | 0 | 2 | 2 | 2 | 0 | 0 | 2 | 0 | 0 | 0 | 0 | 0 |
| N | 3 | 0 | 2 | 3 | 5 | 5 | 5 | 5 | 3 | 2 | 3 | 5 | 7 | 5 | 3 | 5 | 3 | 8 | 0 | 0 | 0 | 0 |
| D | 23 | 2 | 5 | 5 | 5 | 12 | 8 | 8 | 7 | 7 | 3 | 2 | 3 | 8 | 5 | 0 | 3 | 3 | 2 | 0 | 100 | 0 |
| Q | 3 | 2 | 0 | 0 | 4 | 0 | 2 | 2 | 3 | 0 | 2 | 3 | 8 | 2 | 5 | 0 | 0 | 0 | 0 | 0 | 0 | 0 |
| E | 15 | 2 | 7 | 12 | 0 | 0 | 5 | 3 | 3 | 0 | 5 | 3 | 0 | 2 | 5 | 5 | 2 | 2 | 0 | 0 | 0 | 0 |
| H | 2 | 2 | 2 | 2 | 2 | 2 | 4 | 0 | 0 | 2 | 4 | 4 | 3 | 0 | 4 | 2 | 2 | 3 | 2 | 0 | 0 | 3 |
| P | 2 | 10 | 7 | 7 | 12 | 10 | 5 | 5 | 0 | 2 | 3 | 5 | 8 | 10 | 7 | 0 | 3 | 3 | 3 | 0 | 0 | 8 |
| Y | 0 | 3 | 7 | 14 | 14 | 10 | 15 | 5 | 8 | 18 | 14 | 10 | 13 | 20 | 35 | 50 | 52 | 58 | 20 | 0 | 0 | 10 |
| W | 0 | 3 | 0 | 0 | 3 | 3 | 0 | 8 | 3 | 5 | 3 | 2 | 5 | 0 | 3 | 2 | 2 | 2 | 6 | 0 | 0 | 0 |
| S | 2 | 8 | 5 | 12 | 10 | 15 | 13 | 8 | 22 | 12 | 18 | 13 | 7 | 10 | 0 | 5 | 3 | 2 | 2 | 0 | 0 | 0 |
| T | 2 | 7 | 3 | 7 | 6 | 7 | 5 | 7 | 3 | 3 | 2 | 3 | 3 | 2 | 8 | 3 | 2 | 3 | 0 | 0 | 0 | 0 |
| G | 18 | 10 | 12 | 8 | 10 | 10 | 10 | 13 | 13 | 13 | 16 | 10 | 10 | 12 | 5 | 3 | 3 | 10 | 52 | 0 | 0 | 0 |
| A | 8 | 5 | 5 | 2 | 4 | 3 | 7 | 2 | 2 | 3 | 4 | 5 | 4 | 6 | 2 | 2 | 7 | 2 | 10 | 0 | 0 | 2 |
| M | 2 | 5 | 2 | 0 | 2 | 3 | 0 | 2 | 2 | 0 | 3 | 0 | 2 | 0 | 0 | 0 | 0 | 0 | 57 | 0 | 0 | 0 |
| C | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| F | 0 | 7 | 3 | 2 | 4 | 7 | 7 | 7 | 10 | 7 | 0 | 9 | 2 | 2 | 2 | 0 | 2 | 0 | 0 | 33 | 0 | 3 |
| L | 5 | 12 | 3 | 3 | 4 | 0 | 4 | 7 | 5 | 5 | 8 | 12 | 7 | 2 | 4 | 5 | 2 | 2 | 0 | 5 | 0 | 2 |
| V | 10 | 0 | 3 | 7 | 2 | 7 | 5 | 3 | 5 | 12 | 8 | 5 | 3 | 2 | 4 | 8 | 5 | 0 | 0 | 0 | 0 | 65 |
| I | 0 | 3 | 10 | 2 | 5 | 0 | 5 | 10 | 2 | 4 | 2 | 5 | 5 | 5 | 0 | 2 | 4 | 2 | 0 | 3 | 0 | 7 |
| n= | 100 | 100 | 100 | 100 | 100 | 100 | 100 | 100 | 100 | 100 | 100 | 100 | 100 | 100 | 100 | 100 | 100 | 100 | 100 | 100 | 100 | 100 |

TABLE 4

Percentage usage of each amino acid at each position of VH CDR3 loops for known human antibodies of 23 amino acids in length as analysed in Zemlin et al., (2003)

Position on VH CDR3 Length

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| R | 3 | 14 | 8 | 8 | 3 | 3 | 5 | 0 | 0 | 5 | 8 | 3 | 5 | 0 | 8 | 8 | 8 | 0 | 0 | 0 | 0 | 0 | 0 |
| K | 0 | 5 | 5 | 3 | 3 | 3 | 0 | 3 | 0 | 3 | 3 | 0 | 0 | 0 | 3 | 0 | 0 | 3 | 0 | 0 | 0 | 0 | 0 |
| N | 0 | 3 | 0 | 3 | 0 | 3 | 0 | 0 | 3 | 0 | 0 | 3 | 0 | 3 | 5 | 0 | 0 | 2 | 3 | 3 | 0 | 0 | 0 |
| D | 35 | 11 | 3 | 8 | 5 | 5 | 5 | 5 | 5 | 0 | 5 | 3 | 3 | 5 | 3 | 0 | 5 | 5 | 12 | 3 | 0 | 100 | 0 |
| Q | 3 | 8 | 0 | 3 | 0 | 0 | 0 | 3 | 0 | 0 | 0 | 3 | 0 | 0 | 0 | 3 | 3 | 0 | 0 | 0 | 0 | 0 | 0 |
| E | 10 | 3 | 3 | 0 | 5 | 5 | 5 | 8 | 0 | 5 | 0 | 3 | 3 | 5 | 3 | 10 | 3 | 0 | 3 | 0 | 0 | 0 | 0 |
| H | 5 | 8 | 0 | 0 | 3 | 5 | 2 | 0 | 0 | 3 | 11 | 3 | 0 | 0 | 3 | 0 | 5 | 0 | 3 | 0 | 0 | 0 | 0 |

TABLE 4-continued

Percentage usage of each amino acid at each position of VH CDR3 loops for known human antibodies of 23 amino acids in length as analysed in Zemlin et al., (2003)

Position on VH CDR3 Length

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| P | 3 | 10 | 5 | 3 | 3 | 3 | 8 | 5 | 8 | 11 | 3 | 3 | 11 | 14 | 3 | 14 | 3 | 0 | 0 | 0 | 0 | 0 | 14 |
| Y | 3 | 5 | 3 | 8 | 13 | 8 | 20 | 8 | 5 | 5 | 5 | 8 | 11 | 16 | 24 | 46 | 40 | 40 | 60 | 16 | 3 | 0 | 10 |
| W | 0 | 0 | 11 | 5 | 0 | 3 | 0 | 3 | 5 | 3 | 5 | 0 | 5 | 3 | 5 | 0 | 0 | 0 | 3 | 16 | 0 | 0 | 0 |
| S | 0 | 0 | 8 | 8 | 8 | 8 | 9 | 8 | 14 | 13 | 8 | 16 | 8 | 11 | 3 | 3 | 3 | 14 | 0 | 0 | 0 | 0 | 0 |
| T | 3 | 3 | 3 | 14 | 0 | 8 | 5 | 4 | 8 | 5 | 13 | 5 | 5 | 16 | 3 | 0 | 3 | 3 | 3 | 3 | 0 | 0 | 0 |
| G | 25 | 14 | 11 | 14 | 14 | 8 | 8 | 11 | 3 | 16 | 11 | 11 | 16 | 8 | 8 | 3 | 8 | 11 | 5 | 42 | 0 | 0 | 0 |
| A | 4 | 5 | 8 | 0 | 5 | 5 | 5 | 11 | 14 | 8 | 11 | 8 | 4 | 5 | 5 | 5 | 5 | 3 | 0 | 14 | 0 | 0 | 0 |
| M | 0 | 0 | 0 | 5 | 3 | 3 | 3 | 0 | 0 | 5 | 0 | 0 | 4 | 0 | 0 | 3 | 0 | 0 | 0 | 0 | 62 | 0 | 0 |
| C | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| F | 0 | 0 | 11 | 3 | 6 | 3 | 3 | 6 | 8 | 5 | 0 | 5 | 0 | 0 | 8 | 8 | 0 | 5 | 0 | 0 | 30 | 0 | 3 |
| L | 3 | 8 | 3 | 5 | 6 | 3 | 3 | 6 | 5 | 0 | 3 | 3 | 8 | 11 | 3 | 0 | 12 | 8 | 3 | 3 | 0 | 0 | 0 |
| V | 3 | 3 | 11 | 5 | 16 | 16 | 16 | 20 | 14 | 8 | 14 | 12 | 6 | 3 | 5 | 0 | 2 | 3 | 5 | 0 | 0 | 0 | 65 |
| I | 0 | 0 | 8 | 5 | 6 | 11 | 0 | 5 | 5 | 5 | 0 | 14 | 8 | 0 | 8 | 0 | 0 | 0 | 0 | 0 | 5 | 0 | 8 |
| n= | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 |

TABLE 5

Percentage usage of each amino acid at each position of VH CDR3 loops for known human antibodies of 24 amino acids in length as analysed in Zemlin et al., (2003)

Position on VH CDR3 Length

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| R | 4 | 4 | 17 | 9 | 0 | 4 | 0 | 9 | 4 | 4 | 13 | 0 | 0 | 0 | 9 | 4 | 4 | 0 | 0 | 0 | 0 | 0 | 0 | 0 |
| K | 0 | 4 | 9 | 0 | 4 | 4 | 0 | 0 | 0 | 0 | 0 | 4 | 0 | 0 | 0 | 0 | 0 | 0 | 0 | 0 | 0 | 0 | 0 | 0 |
| N | 4 | 0 | 0 | 0 | 9 | 0 | 0 | 0 | 5 | 0 | 0 | 0 | 0 | 9 | 0 | 17 | 0 | 0 | 4 | 4 | 0 | 0 | 0 | 0 |
| D | 30 | 4 | 4 | 13 | 17 | 0 | 9 | 4 | 4 | 9 | 4 | 0 | 0 | 13 | 0 | 17 | 4 | 0 | 0 | 4 | 0 | 0 | 100 | 0 |
| Q | 0 | 4 | 0 | 0 | 0 | 0 | 0 | 0 | 0 | 0 | 4 | 4 | 0 | 0 | 4 | 0 | 0 | 0 | 0 | 0 | 0 | 0 | 0 | 0 |
| E | 4 | 17 | 0 | 0 | 2 | 12 | 0 | 0 | 5 | 0 | 0 | 4 | 0 | 9 | 4 | 0 | 0 | 0 | 0 | 0 | 0 | 0 | 0 | 0 |
| H | 0 | 2 | 0 | 9 | 4 | 0 | 0 | 4 | 4 | 0 | 2 | 5 | 0 | 0 | 5 | 5 | 4 | 0 | 4 | 0 | 0 | 0 | 0 | 0 |
| P | 0 | 9 | 13 | 4 | 13 | 10 | 13 | 0 | 0 | 4 | 4 | 0 | 12 | 12 | 0 | 9 | 0 | 4 | 0 | 0 | 12 | 0 | 0 | 4 |
| Y | 0 | 0 | 4 | 9 | 4 | 15 | 26 | 30 | 30 | 18 | 15 | 22 | 10 | 9 | 22 | 9 | 65 | 74 | 70 | 65 | 20 | 0 | 0 | 8 |
| W | 0 | 0 | 0 | 0 | 2 | 0 | 0 | 4 | 4 | 4 | 10 | 4 | 10 | 0 | 0 | 4 | 0 | 0 | 0 | 4 | 5 | 0 | 0 | 0 |
| S | 0 | 9 | 4 | 0 | 4 | 20 | 13 | 17 | 26 | 22 | 13 | 22 | 10 | 13 | 12 | 0 | 0 | 14 | 22 | 0 | 0 | 0 | 0 | 0 |
| T | 9 | 9 | 0 | 0 | 4 | 10 | 9 | 4 | 4 | 9 | 9 | 4 | 0 | 0 | 0 | 26 | 4 | 4 | 0 | 0 | 0 | 0 | 0 | 0 |
| G | 14 | 30 | 9 | 26 | 20 | 0 | 9 | 4 | 0 | 17 | 9 | 13 | 35 | 30 | 13 | 9 | 15 | 9 | 0 | 0 | 60 | 0 | 0 | 4 |
| A | 14 | 4 | 9 | 17 | 4 | 0 | 13 | 0 | 5 | 4 | 8 | 4 | 0 | 5 | 4 | 0 | 0 | 0 | 0 | 0 | 4 | 0 | 0 | 0 |
| M | 0 | 0 | 0 | 0 | 0 | 0 | 0 | 0 | 0 | 0 | 0 | 0 | 0 | 4 | 0 | 0 | 0 | 0 | 0 | 0 | 0 | 75 | 0 | 0 |
| C | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| F | 0 | 0 | 0 | 0 | 0 | 0 | 0 | 5 | 0 | 5 | 4 | 4 | 0 | 4 | 0 | 0 | 0 | 4 | 5 | 0 | 15 | 0 | 0 | 0 |
| L | 0 | 0 | 9 | 13 | 5 | 5 | 4 | 5 | 0 | 0 | 5 | 5 | 15 | 0 | 5 | 4 | 0 | 9 | 4 | 0 | 0 | 0 | 0 | 0 |
| V | 17 | 0 | 9 | 0 | 4 | 10 | 4 | 9 | 9 | 2 | 0 | 0 | 0 | 0 | 9 | 0 | 0 | 0 | 0 | 0 | 0 | 0 | 0 | 80 |
| I | 4 | 4 | 13 | 0 | 4 | 10 | 0 | 5 | 0 | 2 | 0 | 5 | 0 | 0 | 9 | 0 | 0 | 0 | 0 | 0 | 0 | 5 | 0 | 4 |
| n= | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 |

TABLE 6

Percentage distribution of amino acid usage along each position of the designed library repertoire of antibodies with VH CDR3 loops of 20 amino acids in length Position on the VH CDR3 Length

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| R | 10 | 10 | 10 | 15 | 0 | 0 | 15 | 5 | 5 | 5 | 5 | 5 | 15 | 5 | 5 | 0 | 0 | 0 | 0 | 0 |
| K | 5 | 0 | 0 | 5 | 5 | 0 | 5 | 0 | 0 | 0 | 0 | 5 | 5 | 5 | 0 | 0 | 0 | 0 | 0 | 0 |
| N | 0 | 0 | 0 | 0 | 0 | 0 | 0 | 0 | 0 | 0 | 0 | 0 | 0 | 0 | 0 | 0 | 0 | 0 | 0 | 0 |
| D | 35 | 10 | 5 | 5 | 10 | 10 | 10 | 10 | 5 | 5 | 5 | 5 | 5 | 0 | 10 | 0 | 0 | 100 | 0 | 0 |
| Q | 0 | 0 | 0 | 0 | 0 | 0 | 0 | 0 | 0 | 0 | 0 | 0 | 0 | 0 | 0 | 0 | 0 | 0 | 0 | 0 |
| E | 5 | 5 | 0 | 0 | 0 | 0 | 5 | 0 | 0 | 0 | 10 | 5 | 5 | 5 | 0 | 0 | 0 | 0 | 0 | 0 |
| H | 0 | 5 | 5 | 5 | 0 | 0 | 0 | 0 | 0 | 0 | 0 | 0 | 0 | 0 | 0 | 0 | 0 | 0 | 0 | 0 |
| P | 5 | 10 | 15 | 5 | 5 | 5 | 5 | 5 | 5 | 5 | 5 | 5 | 5 | 0 | 0 | 5 | 0 | 0 | 0 | 10 |
| Y | 0 | 10 | 10 | 10 | 20 | 10 | 10 | 5 | 10 | 10 | 15 | 20 | 40 | 50 | 50 | 60 | 40 | 0 | 0 | 20 |
| W | 0 | 0 | 0 | 5 | 0 | 0 | 0 | 0 | 5 | 0 | 0 | 0 | 0 | 0 | 0 | 0 | 10 | 0 | 0 | 0 |
| S | 5 | 10 | 5 | 5 | 10 | 20 | 10 | 15 | 15 | 20 | 10 | 5 | 10 | 5 | 5 | 5 | 0 | 0 | 0 | 0 |

TABLE 6-continued

Percentage distribution of amino acid usage along each position of the designed library repertoire of antibodies with VH CDR3 loops of 20 amino acids in length Position on the VH CDR3 Length

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| T | 0 | 0 | 10 | 0 | 5 | 0 | 5 | 5 | 5 | 5 | 5 | 5 | 5 | 5 | 5 | 5 | 0 | 0 | 0 | 0 |
| G | 20 | 20 | 10 | 10 | 10 | 15 | 15 | 15 | 10 | 10 | 15 | 15 | 10 | 15 | 5 | 10 | 40 | 0 | 0 | 0 |
| A | 5 | 0 | 10 | 5 | 5 | 5 | 0 | 5 | 5 | 10 | 5 | 5 | 0 | 5 | 5 | 0 | 10 | 0 | 0 | 0 |
| M | 0 | 0 | 0 | 0 | 10 | 5 | 0 | 10 | 5 | 5 | 0 | 0 | 0 | 0 | 0 | 0 | 0 | 50 | 0 | 0 |
| C | 0 | 0 | 0 | 0 | 0 | 0 | 0 | 0 | 0 | 0 | 0 | 0 | 0 | 0 | 0 | 0 | 0 | 0 | 0 | 0 |
| F | 0 | 5 | 10 | 5 | 0 | 5 | 5 | 5 | 5 | 5 | 5 | 5 | 0 | 0 | 5 | 5 | 0 | 40 | 0 | 0 |
| L | 0 | 10 | 0 | 5 | 5 | 5 | 0 | 5 | 10 | 5 | 5 | 5 | 0 | 0 | 5 | 5 | 0 | 5 | 0 | 5 |
| V | 10 | 5 | 10 | 5 | 5 | 10 | 10 | 10 | 10 | 10 | 10 | 10 | 0 | 0 | 5 | 0 | 0 | 0 | 0 | 60 |
| I | 0 | 0 | 0 | 15 | 5 | 10 | 5 | 5 | 5 | 5 | 5 | 5 | 0 | 0 | 0 | 0 | 0 | 0 | 0 | 5 |
| n= | 100 | 100 | 100 | 100 | 100 | 100 | 100 | 100 | 100 | 100 | 100 | 100 | 100 | 100 | 100 | 100 | 100 | 100 | 100 | 100 |

TABLE 7

Percentage distribution of amino acid usage along each position of the designed library repertoire of antibodies with VH CDR3 loops of 21 amino acids in length Position on the VH CDR3

| | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| R | 10 | 10 | 10 | 15 | 0 | 0 | 15 | 5 | 5 | 5 | 5 | 5 | 5 | 15 | 5 | 5 | 0 | 0 | 0 | 0 | 0 |
| K | 5 | 0 | 0 | 5 | 5 | 0 | 5 | 0 | 0 | 0 | 0 | 0 | 5 | 5 | 5 | 0 | 0 | 0 | 0 | 0 | 0 |
| N | 0 | 0 | 0 | 0 | 0 | 0 | 0 | 0 | 0 | 0 | 0 | 0 | 0 | 0 | 0 | 0 | 0 | 0 | 0 | 0 | 0 |
| D | 35 | 10 | 5 | 5 | 10 | 10 | 10 | 5 | 5 | 5 | 5 | 5 | 5 | 5 | 0 | 0 | 10 | 0 | 0 | 100 | 0 |
| Q | 0 | 0 | 0 | 0 | 0 | 0 | 0 | 0 | 0 | 0 | 0 | 0 | 0 | 0 | 0 | 0 | 0 | 0 | 0 | 0 | 0 |
| E | 5 | 5 | 0 | 0 | 0 | 0 | 5 | 0 | 0 | 5 | 0 | 10 | 5 | 5 | 5 | 5 | 0 | 0 | 0 | 0 | 0 |
| H | 0 | 5 | 5 | 5 | 5 | 0 | 0 | 0 | 0 | 0 | 0 | 0 | 0 | 0 | 0 | 0 | 0 | 0 | 0 | 0 | 0 |
| P | 5 | 10 | 15 | 5 | 5 | 5 | 5 | 5 | 5 | 5 | 5 | 5 | 5 | 5 | 5 | 5 | 0 | 0 | 5 | 0 | 10 |
| Y | 0 | 10 | 10 | 10 | 20 | 10 | 10 | 10 | 20 | 10 | 10 | 15 | 20 | 40 | 50 | 50 | 60 | 40 | 0 | 0 | 20 |
| W | 0 | 0 | 0 | 5 | 0 | 0 | 0 | 5 | 5 | 5 | 0 | 0 | 0 | 0 | 0 | 0 | 0 | 10 | 0 | 0 | 0 |
| S | 5 | 10 | 5 | 5 | 10 | 20 | 10 | 15 | 15 | 20 | 20 | 10 | 5 | 10 | 5 | 5 | 5 | 0 | 0 | 0 | 0 |
| T | 0 | 0 | 10 | 0 | 5 | 0 | 5 | 5 | 5 | 0 | 5 | 5 | 5 | 5 | 5 | 5 | 5 | 0 | 0 | 0 | 0 |
| G | 20 | 20 | 10 | 10 | 10 | 15 | 15 | 10 | 10 | 15 | 10 | 15 | 15 | 10 | 15 | 5 | 10 | 40 | 0 | 0 | 0 |
| A | 5 | 0 | 10 | 5 | 5 | 5 | 0 | 5 | 5 | 5 | 10 | 5 | 5 | 0 | 5 | 5 | 0 | 10 | 0 | 0 | 0 |
| M | 0 | 0 | 0 | 0 | 10 | 5 | 0 | 5 | 0 | 0 | 0 | 5 | 0 | 0 | 0 | 0 | 0 | 0 | 50 | 0 | 0 |
| C | 0 | 0 | 0 | 0 | 0 | 0 | 0 | 0 | 0 | 0 | 0 | 0 | 0 | 0 | 0 | 0 | 0 | 0 | 0 | 0 | 0 |
| F | 0 | 5 | 10 | 5 | 0 | 5 | 5 | 5 | 5 | 0 | 5 | 5 | 5 | 0 | 0 | 5 | 5 | 0 | 40 | 0 | 0 |
| L | 0 | 10 | 0 | 5 | 5 | 5 | 0 | 10 | 5 | 10 | 5 | 5 | 5 | 0 | 0 | 5 | 5 | 0 | 5 | 0 | 5 |
| V | 10 | 5 | 10 | 5 | 5 | 10 | 10 | 10 | 10 | 10 | 10 | 10 | 10 | 0 | 0 | 5 | 0 | 0 | 0 | 0 | 60 |
| I | 0 | 0 | 0 | 15 | 5 | 10 | 5 | 5 | 5 | 5 | 5 | 5 | 5 | 0 | 0 | 0 | 0 | 0 | 0 | 0 | 5 |
| n= | 100 | 100 | 100 | 100 | 100 | 100 | 100 | 100 | 100 | 100 | 100 | 100 | 100 | 100 | 100 | 100 | 100 | 100 | 100 | 100 | 100 |

TABLE 8

Percentage distribution of amino acid usage along each position of the designed library repertoire of antibodies with VH CDR3 loops of 22 amino acids in length Position on the VH CDR3

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| R | 10 | 10 | 10 | 15 | 0 | 0 | 15 | 5 | 5 | 5 | 5 | 5 | 5 | 5 | 15 | 5 | 5 | 0 | 0 | 0 | 0 | 0 |
| K | 5 | 0 | 0 | 5 | 5 | 0 | 5 | 0 | 0 | 0 | 0 | 0 | 0 | 5 | 5 | 5 | 0 | 0 | 0 | 0 | 0 | 0 |
| N | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| D | 35 | 10 | 5 | 5 | 10 | 10 | 10 | 10 | 5 | 5 | 5 | 5 | 5 | 5 | 5 | 0 | 0 | 10 | 0 | 0 | 100 | 0 |
| Q | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| E | 5 | 5 | 0 | 0 | 0 | 0 | 5 | 0 | 0 | 0 | 5 | 0 | 10 | 5 | 5 | 5 | 5 | 0 | 0 | 0 | 0 | 0 |
| H | 0 | 5 | 5 | 5 | 5 | 0 | 0 | 0 | 0 | 0 | 0 | 0 | 0 | 0 | 0 | 0 | 0 | 0 | 0 | 0 | 0 | 0 |
| P | 5 | 10 | 15 | 5 | 5 | 5 | 5 | 5 | 5 | 5 | 5 | 5 | 5 | 5 | 5 | 5 | 5 | 0 | 0 | 5 | 0 | 10 |
| Y | 0 | 10 | 10 | 10 | 20 | 10 | 10 | 5 | 10 | 20 | 10 | 10 | 15 | 20 | 40 | 50 | 50 | 60 | 40 | 0 | 0 | 20 |
| W | 0 | 0 | 0 | 5 | 0 | 0 | 0 | 0 | 5 | 5 | 5 | 0 | 0 | 0 | 0 | 0 | 0 | 0 | 10 | 0 | 0 | 0 |
| S | 5 | 10 | 5 | 5 | 10 | 20 | 10 | 15 | 15 | 15 | 20 | 20 | 10 | 5 | 10 | 5 | 5 | 5 | 0 | 0 | 0 | 0 |
| T | 0 | 0 | 10 | 0 | 5 | 0 | 5 | 5 | 5 | 5 | 0 | 5 | 5 | 5 | 5 | 5 | 5 | 5 | 0 | 0 | 0 | 0 |
| G | 20 | 20 | 10 | 10 | 10 | 15 | 15 | 15 | 10 | 10 | 15 | 10 | 15 | 15 | 10 | 15 | 5 | 10 | 40 | 0 | 0 | 0 |
| A | 5 | 0 | 10 | 5 | 5 | 5 | 0 | 5 | 5 | 5 | 5 | 10 | 5 | 5 | 0 | 5 | 5 | 0 | 10 | 0 | 0 | 0 |
| M | 0 | 0 | 0 | 0 | 10 | 5 | 0 | 10 | 5 | 0 | 0 | 5 | 0 | 0 | 0 | 0 | 0 | 0 | 0 | 50 | 0 | 0 |

TABLE 8-continued

Percentage distribution of amino acid usage along each position of the designed library repertoire of antibodies with VH CDR3 loops of 22 amino acids in length

| | \multicolumn{22}{c}{Position on the VH CDR3} |
|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| C | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| F | 0 | 5 | 10 | 5 | 0 | 5 | 5 | 5 | 5 | 5 | 0 | 5 | 5 | 5 | 0 | 0 | 5 | 5 | 0 | 40 | 0 | 0 |
| L | 0 | 10 | 0 | 5 | 5 | 5 | 0 | 5 | 10 | 5 | 10 | 5 | 5 | 5 | 0 | 0 | 5 | 5 | 0 | 5 | 0 | 5 |
| V | 10 | 5 | 10 | 5 | 5 | 10 | 10 | 10 | 10 | 10 | 10 | 10 | 10 | 10 | 0 | 0 | 5 | 0 | 0 | 0 | 0 | 60 |
| I | 0 | 0 | 0 | 15 | 5 | 10 | 5 | 5 | 5 | 5 | 5 | 5 | 5 | 5 | 0 | 0 | 0 | 0 | 0 | 0 | 0 | 5 |
| n= | 100 | 100 | 100 | 100 | 100 | 100 | 100 | 100 | 100 | 100 | 100 | 100 | 100 | 100 | 100 | 100 | 100 | 100 | 100 | 100 | 100 | 100 |

TABLE 9

Percentage distribution of amino acid usage along each position of the designed library repertoire of antibodies with VH CDR3 loops of 23 amino acids in length

| | \multicolumn{23}{c}{Position on the VH CDR3} |
|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
| R | 10 | 10 | 10 | 15 | 0 | 0 | 15 | 5 | 5 | 15 | 0 | 5 | 5 | 5 | 5 | 15 | 5 | 5 | 0 | 0 | 0 | 0 | 0 |
| K | 5 | 0 | 0 | 5 | 5 | 0 | 5 | 0 | 0 | 0 | 5 | 0 | 0 | 0 | 5 | 5 | 5 | 0 | 0 | 0 | 0 | 0 | 0 |
| N | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| D | 35 | 10 | 5 | 5 | 10 | 10 | 10 | 5 | 5 | 5 | 0 | 5 | 5 | 5 | 5 | 0 | 0 | 10 | 0 | 0 | 0 | 100 | 0 |
| Q | 0 | 0 | 0 | 0 | 0 | 0 | 0 | 0 | 0 | 5 | 5 | 0 | 0 | 0 | 0 | 0 | 0 | 0 | 0 | 0 | 0 | 0 | 0 |
| E | 5 | 5 | 0 | 0 | 0 | 0 | 5 | 0 | 0 | 0 | 5 | 5 | 0 | 10 | 5 | 5 | 5 | 5 | 0 | 0 | 0 | 0 | 0 |
| H | 0 | 5 | 5 | 5 | 5 | 0 | 0 | 0 | 0 | 0 | 5 | 0 | 0 | 0 | 0 | 0 | 0 | 0 | 0 | 0 | 0 | 0 | 0 |
| P | 5 | 10 | 15 | 5 | 5 | 5 | 5 | 5 | 5 | 5 | 0 | 5 | 5 | 5 | 0 | 5 | 5 | 5 | 0 | 5 | 0 | 0 | 10 |
| Y | 0 | 10 | 10 | 10 | 20 | 10 | 10 | 10 | 20 | 15 | 20 | 10 | 10 | 15 | 20 | 40 | 50 | 50 | 60 | 40 | 0 | 0 | 20 |
| W | 0 | 0 | 0 | 5 | 0 | 0 | 0 | 5 | 5 | 10 | 5 | 5 | 0 | 0 | 0 | 0 | 0 | 0 | 10 | 0 | 0 | 0 | 0 |
| S | 5 | 10 | 5 | 5 | 10 | 20 | 10 | 15 | 15 | 15 | 20 | 20 | 20 | 10 | 5 | 10 | 5 | 5 | 5 | 0 | 0 | 0 | 0 |
| T | 0 | 0 | 10 | 0 | 5 | 0 | 5 | 5 | 5 | 5 | 10 | 5 | 0 | 5 | 5 | 5 | 5 | 5 | 5 | 0 | 0 | 0 | 0 |
| G | 20 | 20 | 10 | 10 | 10 | 15 | 15 | 10 | 10 | 10 | 10 | 15 | 10 | 15 | 15 | 10 | 15 | 5 | 10 | 40 | 0 | 0 | 0 |
| A | 5 | 0 | 10 | 5 | 5 | 5 | 0 | 5 | 5 | 10 | 5 | 5 | 10 | 5 | 5 | 0 | 5 | 5 | 0 | 10 | 0 | 0 | 0 |
| M | 0 | 0 | 0 | 0 | 10 | 5 | 0 | 5 | 0 | 0 | 0 | 0 | 5 | 0 | 0 | 0 | 0 | 0 | 0 | 50 | 0 | 0 | 0 |
| C | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| F | 0 | 5 | 10 | 5 | 0 | 5 | 5 | 5 | 5 | 0 | 5 | 0 | 5 | 5 | 5 | 0 | 0 | 5 | 5 | 0 | 40 | 0 | 0 |
| L | 0 | 10 | 0 | 5 | 5 | 5 | 0 | 10 | 5 | 0 | 5 | 10 | 5 | 5 | 5 | 0 | 0 | 5 | 5 | 0 | 5 | 0 | 5 |
| V | 10 | 5 | 10 | 5 | 5 | 10 | 10 | 10 | 10 | 0 | 0 | 10 | 10 | 10 | 10 | 0 | 0 | 5 | 0 | 0 | 0 | 0 | 60 |
| I | 0 | 0 | 0 | 15 | 5 | 10 | 5 | 5 | 5 | 0 | 5 | 5 | 5 | 5 | 5 | 0 | 0 | 0 | 0 | 0 | 0 | 0 | 5 |
| n= | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 |

TABLE 10

Percentage distribution of amino acid usage along each position of the designed library repertoire of antibodies with VH CDR3 loops of 24 amino acids in length

| | \multicolumn{24}{c}{Position on the VH CDR3} |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| R | 10 | 10 | 10 | 15 | 0 | 0 | 15 | 5 | 5 | 5 | 15 | 0 | 5 | 5 | 5 | 5 | 15 | 5 | 5 | 0 | 0 | 0 | 0 | 0 |
| K | 5 | 0 | 0 | 5 | 5 | 0 | 5 | 0 | 0 | 0 | 0 | 5 | 0 | 0 | 0 | 5 | 5 | 5 | 0 | 0 | 0 | 0 | 0 | 0 |
| N | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| D | 35 | 10 | 5 | 5 | 10 | 10 | 10 | 5 | 5 | 5 | 0 | 5 | 5 | 5 | 5 | 5 | 0 | 0 | 10 | 0 | 0 | 100 | 0 | |
| Q | 0 | 0 | 0 | 0 | 0 | 0 | 0 | 0 | 0 | 5 | 5 | 0 | 0 | 0 | 0 | 0 | 0 | 0 | 0 | 0 | 0 | 0 | 0 | |
| E | 5 | 5 | 0 | 0 | 0 | 0 | 5 | 0 | 0 | 0 | 5 | 5 | 0 | 10 | 5 | 5 | 5 | 5 | 0 | 0 | 0 | 0 | 0 | |
| H | 0 | 5 | 5 | 5 | 5 | 0 | 0 | 0 | 0 | 0 | 5 | 0 | 0 | 0 | 0 | 0 | 0 | 0 | 0 | 0 | 0 | 0 | 0 | |
| P | 5 | 10 | 15 | 5 | 5 | 5 | 5 | 5 | 5 | 5 | 0 | 5 | 5 | 5 | 0 | 5 | 5 | 5 | 0 | 5 | 0 | 0 | 10 | |
| Y | 0 | 10 | 10 | 10 | 20 | 10 | 10 | 5 | 10 | 20 | 15 | 20 | 10 | 10 | 15 | 20 | 40 | 50 | 50 | 60 | 40 | 0 | 0 | 20 |
| W | 0 | 0 | 0 | 5 | 0 | 0 | 0 | 0 | 5 | 5 | 10 | 5 | 5 | 0 | 0 | 0 | 0 | 0 | 0 | 10 | 0 | 0 | 0 | |
| S | 5 | 10 | 5 | 5 | 10 | 20 | 10 | 15 | 15 | 15 | 15 | 20 | 20 | 20 | 10 | 5 | 10 | 5 | 5 | 5 | 0 | 0 | 0 | |
| T | 0 | 0 | 10 | 0 | 5 | 0 | 5 | 5 | 5 | 5 | 10 | 0 | 5 | 0 | 5 | 5 | 5 | 5 | 5 | 5 | 0 | 0 | 0 | |
| G | 20 | 20 | 10 | 10 | 10 | 15 | 15 | 15 | 10 | 10 | 10 | 10 | 15 | 10 | 15 | 15 | 10 | 15 | 5 | 10 | 40 | 0 | 0 | |
| A | 5 | 0 | 10 | 5 | 5 | 5 | 0 | 5 | 5 | 5 | 10 | 5 | 5 | 10 | 5 | 0 | 5 | 5 | 0 | 10 | 0 | 0 | 0 | |
| M | 0 | 0 | 0 | 0 | 10 | 5 | 0 | 10 | 5 | 0 | 0 | 0 | 0 | 5 | 0 | 0 | 0 | 0 | 0 | 0 | 50 | 0 | 0 | |
| C | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | |
| F | 0 | 5 | 10 | 5 | 0 | 5 | 5 | 5 | 5 | 5 | 0 | 5 | 0 | 5 | 5 | 5 | 0 | 0 | 5 | 5 | 0 | 40 | 0 | 0 |

TABLE 10-continued

Percentage distribution of amino acid usage along each position of the designed library repertoire of antibodies with VH CDR3 loops of 24 amino acids in length Position on the VH CDR3

|   | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|----|----|----|----|----|----|----|----|----|----|----|----|----|----|----|
| L | 0 | 10 | 0 | 5 | 5 | 5 | 0 | 5 | 10 | 5 | 0 | 5 | 10 | 5 | 5 | 5 | 0 | 0 | 5 | 5 | 0 | 5 | 0 | 5 |
| V | 10 | 5 | 10 | 5 | 5 | 10 | 10 | 10 | 10 | 10 | 0 | 0 | 10 | 10 | 10 | 10 | 0 | 0 | 5 | 0 | 0 | 0 | 0 | 60 |
| I | 0 | 0 | 0 | 15 | 5 | 10 | 5 | 5 | 5 | 5 | 0 | 5 | 5 | 5 | 5 | 5 | 0 | 0 | 0 | 0 | 0 | 0 | 0 | 5 |
| n= | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 |

TABLE 11

Percentage distribution of amino acid usage along each position of the designed library repertoire of antibodies with VH CDR3 loops of 24 amino acids in length, with a fixed cysteine pair at loop positions 11 and 16

|   | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|----|----|----|----|----|----|----|----|----|----|----|----|----|----|----|
| R | 10 | 10 | 10 | 15 | 0 | 0 | 15 | 5 | 5 | 5 | 0 | 0 | 5 | 5 | 5 | 0 | 15 | 5 | 5 | 0 | 0 | 0 | 0 | 0 |
| K | 5 | 0 | 0 | 5 | 5 | 0 | 5 | 0 | 0 | 0 | 0 | 5 | 0 | 0 | 0 | 0 | 5 | 5 | 0 | 0 | 0 | 0 | 0 | 0 |
| N | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| D | 35 | 10 | 5 | 5 | 10 | 10 | 10 | 10 | 5 | 5 | 0 | 0 | 5 | 5 | 5 | 0 | 5 | 0 | 0 | 10 | 0 | 0 | 100 | 0 |
| Q | 0 | 0 | 0 | 0 | 0 | 0 | 0 | 0 | 0 | 0 | 0 | 5 | 0 | 0 | 0 | 0 | 0 | 0 | 0 | 0 | 0 | 0 | 0 | 0 |
| E | 5 | 5 | 0 | 0 | 0 | 5 | 0 | 0 | 0 | 0 | 0 | 5 | 5 | 0 | 10 | 0 | 5 | 5 | 5 | 0 | 0 | 0 | 0 | 0 |
| H | 0 | 5 | 5 | 5 | 5 | 0 | 0 | 0 | 0 | 0 | 0 | 5 | 0 | 0 | 0 | 0 | 0 | 0 | 0 | 0 | 0 | 0 | 0 | 0 |
| P | 5 | 10 | 15 | 5 | 5 | 5 | 5 | 5 | 5 | 5 | 0 | 0 | 5 | 5 | 5 | 0 | 5 | 5 | 5 | 0 | 0 | 5 | 0 | 10 |
| Y | 0 | 10 | 10 | 10 | 20 | 10 | 10 | 5 | 10 | 20 | 0 | 20 | 0 | 10 | 10 | 15 | 0 | 40 | 50 | 50 | 60 | 40 | 0 | 20 |
| W | 0 | 0 | 0 | 5 | 0 | 0 | 0 | 0 | 5 | 5 | 0 | 5 | 5 | 0 | 0 | 0 | 0 | 0 | 0 | 0 | 10 | 0 | 0 | 0 |
| S | 5 | 10 | 5 | 5 | 10 | 20 | 10 | 15 | 15 | 15 | 0 | 20 | 20 | 20 | 10 | 0 | 10 | 5 | 5 | 5 | 0 | 0 | 0 | 0 |
| T | 0 | 0 | 10 | 0 | 5 | 0 | 5 | 5 | 5 | 5 | 0 | 5 | 0 | 5 | 5 | 0 | 5 | 5 | 5 | 5 | 0 | 0 | 0 | 0 |
| G | 20 | 20 | 10 | 10 | 10 | 15 | 15 | 15 | 10 | 10 | 0 | 10 | 15 | 10 | 15 | 0 | 10 | 15 | 5 | 10 | 40 | 0 | 0 | 0 |
| A | 5 | 0 | 10 | 5 | 5 | 5 | 0 | 5 | 5 | 5 | 0 | 5 | 5 | 10 | 5 | 0 | 0 | 5 | 5 | 0 | 10 | 0 | 0 | 0 |
| M | 0 | 0 | 0 | 0 | 10 | 5 | 0 | 10 | 5 | 0 | 0 | 0 | 5 | 0 | 0 | 0 | 0 | 0 | 0 | 0 | 0 | 50 | 0 | 0 |
| C | 0 | 0 | 0 | 0 | 0 | 0 | 0 | 0 | 0 | 0 | 100 | 0 | 0 | 0 | 0 | 100 | 0 | 0 | 0 | 0 | 0 | 0 | 0 | 0 |
| F | 0 | 5 | 10 | 5 | 0 | 5 | 5 | 5 | 5 | 0 | 0 | 5 | 0 | 5 | 0 | 0 | 0 | 5 | 5 | 5 | 0 | 40 | 0 | 0 |
| L | 0 | 10 | 0 | 5 | 5 | 5 | 0 | 5 | 10 | 5 | 0 | 5 | 10 | 5 | 5 | 5 | 0 | 0 | 5 | 5 | 0 | 5 | 0 | 5 |
| V | 10 | 5 | 10 | 5 | 5 | 10 | 10 | 10 | 10 | 10 | 0 | 0 | 10 | 10 | 10 | 0 | 0 | 0 | 5 | 0 | 0 | 0 | 0 | 60 |
| I | 0 | 0 | 0 | 15 | 5 | 10 | 5 | 5 | 5 | 5 | 0 | 5 | 5 | 5 | 5 | 0 | 0 | 0 | 0 | 0 | 0 | 0 | 0 | 5 |
| n= | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 |

EXAMPLE 2

Cloning of the VH Repertoire and Preparation of the EG3 Library

In order to maximise the diversity of the final library, the 6 VH repertoires were cloned into a phagemid vector containing human antibody V lambda and V kappa genes (Lloyd C et al., 2009; Protein Eng Des Sel 22(3): 159-168). This acceptor framework library (in pCantab6 vector) was grown up overnight and DNA was extracted by Maxiprep (Qiagen, Manchester, UK). The purified DNA was sequentially digested by restriction enzymes NcoI and XhoI (NEB, Hitchin, UK) at 37 degrees C. followed by a 20 min 80 degrees C. heat inactivation step. Double-digested vector was purified by phenol:chloroform extraction with Phase Lock Gel (5Prime GmbH, Hilden, Germany) and subsequent ethanol precipitation. The DNA stuffer fragments were removed by purification of the vector DNA on Chromospin+ TE-1000 columns (Takara Clontech, Saint-Germain-en-Laye, France). The 6 VH repertoire inserts were simultaneously digested with restriction enzymes NcoI and XhoI (NEB) for 4 hrs at 37 degrees C. followed by a 20 min 80 degrees C. heat inactivation step to generate the relevant overhangs.

Trial ligations were performed using the T4 ligase kit (NEB), at varying ratios (3:1, 6:1 and 12:1 insert:vector), before being phenol:chloroform extracted and ethanol precipitated. Ligations were then electroporated into freshly-made electrocompetent TG1 cells, before being recovered at 37 degrees C. Cells were plated onto agar containing the relevant antibiotic and incubated at 30 degrees C. overnight. Colony PCR was performed on colonies to confirm correct ligation of vector and insert. Once a insert:vector ratio had been selected, large-scale ligations were performed as previously described for each of the sub-libraries. Serial dilutions were performed to provide an estimate of library size, as previously described (Marks JD, et al. (1991) J. Mol. Biol., 222:581-5971). scFv genes for 264-528 individual clones from each sub-library were sequenced to determine estimates of HCDR3 diversity and library quality. This analysis indicated that the library was highly diverse (100% diversity in HCDR3 sequence among sequenced clones) and that ~70% of the clones in each sub-library encode full-length, in-frame scFv (FIG. 3).

After successful cloning of the six individual sub-libraries, phage aliquots of the individual sub-libraries were prepared using standard techniques (Sambrook J, et al, (1987) Molecular Cloning—A Laboratory Approach. Cold Spring Harbor Laboratory Press.). These were then combined at an equivalent ratio. The final combined scFv library had a repertoire that was estimated to have a size of 7.5×10$^9$ individual recombinants and was termed the EG3 library.

DNA from the newly-constructed library was prepared and submitted for sequencing by Next Generation Sequencing (MiSeq—Illumina, Little Chesterford, UK) in order to determine VHCDR3 length distribution and VHCDR3 amino acid usage in each sub-library. An estimate of VL germline diversity was also obtained, as the VH had a fixed framework.

From 1.2-1.6 million individual reads per sub-library, the NGS (Next Generation Sequencing, i.e. as carried out using Illumina MiSeq®) indicates that 60-70% clones in each sub-library contain a VHCDR3 of the expected length (FIG. 4). This analysis also confirmed that for the vast majority of the positions in each sub-library, amino acid usage in the final library was consistent (frequency of amino acid observed/designed=0.1-2) with the library design. Where the amino acid usage did not fall in the expected range, the amino acid in each case was designed to occur <10% at that position. For example, in each library, isoleucine was slightly over-represented at Kabat position 98 (observed=0.12 vs designed 0.05) and tyrosine was somewhat over-represented at Kabat position 102 (observed=0.21 vs designed 0.1). 100000 randomly chosen individual reads per sub-library were used to generate information about VL germline diversity (FIG. 5). The three most frequently used VL germlines are IGLV1-44*01, IGV3-19*01 and IGLV1-40*01, each representing 7-10% of each sub-library. The most common kappa germline is IGKV3-20*01, representing 4-5% of each sub-library.

EXAMPLE 3

Isolation of scFv's from EG3 Library to Model Antigens SCF and Insulin

In order to test the performance of the EG3 library against a typical soluble antigen, selections were performed against two model antigens, human insulin and human stem cell factor (SCF). scFv antibodies specific for SCF or insulin were isolated from the EG3 library and compared against two previously described human scFv antibody libraries (Groves, et al., J. Immunol. Methods, 313:129-139 (2006); Lloyd et al., Protein Eng. Des. Sel. 22(3):159-68 (2009)) by soluble selection against biotinylated recombinant human SCF ECD (residues 1-214; produced in HEK293 EBNA cells) or biotinylated bovine insulin (Sigma catalog 15500, biotinylated via free amines using EZ link Sulfo-NHS-LC-Biotin (Thermo/Pierce, 21335)) essentially as described in Vaughan et al. Nat. Biotech. 14, 309-314 (1996) and Hawkins et al. (J. Mol. Biol. 226, 889-896 (1992). Briefly, 10$^9$-10$^{12}$ scFv-phage particles were blocked for 1 hr at room temperature in MPBS (PBS+3% (w/v) Marvel skimmed milk powder). 50 µl streptavidin-coated paramagnetic beads (Dynabeads®, M-280) were added to the blocked phage followed by 1 hr incubation. The streptavidin beads were captured with a magnet, and biotinylated SCF or insulin was added to a final concentration of 100 nm (round 1) or 50 nm (round 2). After 1 hr incubation at room temperature, scFv bound to antigen were then captured on streptavidin-coated paramagnetic beads. Unbound phage were removed by extensive washing of the beads with PBST (PBS+0.1% (v/v) Tween-20). The phage particles retained on the antigen were eluted by addition of 5 µg/ml trypsin followed by a 30 min incubation at 37° C. The beads were captured on a magnet, and the supernatant used to infect log-phase TG1 E. coli, followed by phage rescue for the next round of selection; two rounds of selection were performed in this way.

96 individual clones (including control clones) from the selection outputs after two rounds of selection described above were grown up in 96-well plates. Single-chain Fv fragments were displayed on phage particles and tested in a binding assay to determine specificity for the relevant selection antigen. Phage-displayed scFv supernatant samples were generated in 96-well deep well plates as follows. 5 µl of culture from each well of a 96-well master plate was transferred into a Greiner deep well culture plate containing 500 µl of 2TYAG (2TY+100 µg/ml ampicillin+2% glucose) media and incubated for 5 hours at 37° C., 280 rpm. K07 M13 helper phage (diluted to 1.5×1011 pfu/ml in 2TYAG) was then added at 100 µl/well and the plate incubated at 37 degrees C., 150 rpm to allow infection. The plate was spun down at 3200 rpm for 10 minutes and the supernatant removed. Bacterial pellets were resuspended in 500 µl/well 2TYAK (2TY+100 µg/ml ampicillin+50 µg/ml kanamycin) and the plate incubated overnight at 25 degrees C., 280 rpm. In the morning, 500 µl of 6% (w/v) skimmed milk powder in 2×PBS was added to each well and the plate incubated for 1 hour at room temperature. The plate was then centrifuged at 3200 rpm for 10 minutes and the blocked phage-displayed scFv supernatants were used directly in ELISA experiments.

Streptavidin plates (Greiner, 655990) were coated with biotinylated antigen at 2.5 µg/ml in PBS and incubated overnight at 4° C. Plates were washed 3× with PBS and blocked with 300 µl/well MPBS for 1 hour at room temperature. Plates were washed 1× with PBS and blocked phage samples added, 50 µl/well for 1 hour at room temperature. Plates were washed 3× with PBST and 50 µl/well anti-M13-HRP antibody (Amersham, 27-9421-01) at 1:5000 dilution in MPBS for detection of phage-displayed scFv was added to each well, followed by a 1 hour incubation at room temperature. Plates were washed 3× with PBST and developed with TMB, 50 µl/well (Sigma, T0440). The reaction was quenched with 50 µl/well 0.1 M H2SO4 before reading on an EnVisionTM plate reader at 450 nm. Phage-displayed scFv were considered to bind the selection antigen if the absorbance at 450 nm was >0.5, and <0.1 for the same sample on the irrelevant antigen. Sequencing of scFv genes for SCF or insulin-binding clones was carried out to assess the VHCDR3 diversity selected clones. A diverse panel of specific binders for both antigens was identified from all three phage libraries after two rounds of soluble selection.

| Phage library | Selection antigen | % specific binders | VHCDR3 diversity of specific binders |
|---|---|---|---|
| CS | Insulin | 73 | 40% |
| DP47 | Insulin | 73 | 66% |
| EG3 | Insulin | 89 | 73% |
| CS | SCF | 68 | 38% |
| DP47 | SCF | 55 | 40% |
| EG3 | SCF | 61 | 19% |

EXAMPLE 4

Identification and Characterisation of Inhibitory Antibodies Against an Ion Channel Isolated Using Phage Display Selection In order to determine whether the EG3 library might be well suited for identifying antibodies to more challenging classes of target, such as ion channels, selections were performed on the ion channel P2X4. Exemplary P2X4 inhibitory antibodies 1-4 were obtained using phage display as described herein. Naïve human single chain Fv (scFv) phage display libraries were cloned into a phagemid vector based on the filamentous phage M13 were used for selections (Lloyd (2009) Protein Eng Des Sel 22, 159-168; Vaughan et al., Nature biotechnology 14, 309-314, 1996). Anti-P2X4 specific antibodies were isolated from the EG3 library, or previously described naïve phage display libraries (collectively referred to as CAT2.0 libraries), using a series of selection cycles on recombinant human P2X4 (hu P2X4), essentially as previously described by Vaughan et al (Vaughan et al., supra). In brief, human P2X4 in PBS (Dulbecco's PBS, pH7.4) was immobilised onto wells of a MaxiSorp® microtitre plate (Nunc) overnight at 4 degrees C. Wells were washed with PBS then blocked for 1 hour with PBS-Marvel dried skimmed milk (3% w/v). Purified phage in PBS-Marvel (3% w/v), were added to the wells and allowed to bind coated antigen for 1 hour at room temperature. Unbound phage was removed by a series of wash cycles using PBS. Bound phage particles were eluted with trypsin for 30 minutes at 37 degrees C., infected into E.coli TG1 bacteria and rescued for the next round of selection.

Identification of Human P2X4 Antibodies from Phage Display Selections

ScFv antibodies identified from the phage display method described (above) were expressed in bacteria and screened as unpurified bacterial periplasmic extracts (which contain scFv), prepared in: 0.2M HEPES buffer pH7.4, 0.5 mM EDTA and 0.5 M sucrose. Alternatively, the heavy and light chain variable regions were amplified by PCR and cloned into a vector for expression as human IgG1 antibodies in HEK293F cells. For screening of bacterial scFv samples, 5 µl of bacterial extract was added to the 384 well assay plate (Corning 3655). Assay buffer was prepared as follows: 1X Hanks Balanced Salt Solution (HBSS) (Sigma H8264), 0.1% (v/v) BSA (PAA K05-013), 20 mM HEPES (Gibco 15630) and 1U/ml Apyrase (Sigma A6535) and 5 µl added to the assay plate with the bacterial scFv extract. Anti-myc detection (Serotec MCA220) and anti-mouse DyLight649 (Jackson Immuno Research Labs 115-495-071) were diluted in assay buffer to 15.6 nm and 24 nm respectively in the same solution and 5 µl added to the assay plate with the scFv sample. HEK293F cells expressing human P2X4 (huP2X4) (Q99571, ENSP00000336607) were diluted to 2.6e5cells/ml in assay buffer and 15 µl added to the assay plate. In parallel scFv samples were also tested for binding to HEK293F cells that did not express huP2X4.

For screening of the HEK293F expressed IgG samples, 2.5 µl of cell culture supernatant was added to the 384 well assay plate (Corning 3655). Assay buffer was prepared as described above and 7.5 µl was added to the assay plate with the IgG sample. Anti-human AlexaFluor 647 (Life Technologies A21445) was diluted in assay buffer to 6 nm and 10 I added to the assay plate with the IgG sample. HEK293F cells expressing huP2X4 (Q99571, ENSP00000336607) were diluted to 4e5cells/ml in assay buffer and 10 I added to the assay plate. In parallel IgG samples were also tested for binding to HEK293F cells that did not express huP2X4. Assay plates set up to screen both types of samples were sealed with a Topseal plate sealer (Perkin Elmer 6005250) and incubated at room temperature for at least 4 hours before reading on the Fluorescence Microvolume Assay Technology (FMAT), a fluorescence based platform that detects fluorescence localized to bead or cells settled at the bottom of microwell (Dietz et al., Cytometry 23:177-186 (1996), Miraglia et al., J. Biomol. Screening 4:193-204 (1999)). Data was analysed using the FMAT analysis software and events were gated based on fluorescence 0-10,000 FL1 counts, colour typically 0.15 to 0.40 and size 10-60. A minimum count of 20 events was set as a threshold before data was reported for each well. ScFv showing binding to the HEK293F huP2X4 cells, but not to the control HEK293F cells were selected for further testing if the FL1 count was above 1000 on the huP2X4 cells, IgG samples showing a specific huP2X4 binding signal of greater than 200 FL1 counts were identified as hits and characterised further.

ScFv or IgG samples which showed a specific binding signal to HEK293F huP2X4 cells as unpurified samples were subjected to DNA sequencing (Vaughan et al. supra, Nature Biotechnology 14: 309-314), (Osbourn 1996;Immunotechnology. 2, 181-196). Unique scFvs were expressed in bacteria and purified by affinity chromatography (as described by Bannister et al (2006) Biotechnology and bioengineering, 94. 931-937). Purified antibodies were tested for functional activity in the electrophysiology.

| | Total no. of scFv's screened for binding to huP2X4 HEK293 cells | No. of IgG's derived that fully inhibit P2X4 signalling in electrophysiology assay |
|---|---|---|
| CAT 2.0 phage libraries | 33000 | 1 |
| EG3 phage library | 174 | 2 |

Electrophysiological Characterisation of Monoclonal Antibodies to P2X4

HEK 293F cells stably expressing human P2X4, were harvested at 50% confluency using accutase. Cells were then resuspended in 10 ml Freestyle 293F media supplemented with HEPES (10 mM)+apyrase (1U/ml, ATPase/ADPase activity=1) at a density of 2-3e6 cells/ml. P2X4 function was assayed using the automated electrophysiology platform QPatch 16X (Sophion) in population patch configuration. Composition of QPatch extracellular buffer (QEB) was (in mM) NaCl (140), KCl (2), MgCl2 (1) CaCl2 (2), HEPES (10). Final composition of compound plate extracellular buffer (CPEB1) was NaCl (137.6), KCl (2.2), MgCl2 (0.66), CaCl2 (1.3), HEPES (6.6), KH2PO4 (0.49), NaH2PO4 (2.66). pH of extracellular buffers was adjusted to 7.4 with NaOH (1 M), osmolarity was adjusted to 300 mOsm with sucrose and the solutions were 0.2 µm filtered. Compound plate extracellular buffer was supplemented with 0.1% bovine serum albumin. The QPatch intracellular buffer contained (in mM) CsF (140), NaCl (10), EGTA (1), HEPES (10). pH of the intracellular buffer was adjusted to 7.3 with CsOH (1 M) and the solution was 0.2 µm filtered. IgGs were titrated to pH 7.4 with NaOH (1 M).

After obtaining whole cell configuration, cells were voltage clamped at −50 mV with 70% series resistance compensation employed. The ligand agonist adenosine 5'-triphosphate disodium salt (ATP, 3 µM) in CPEB1 was applied for 3 seconds every 5 minutes for 20 minutes resulting in 4 control agonist responses. Each agonist response was washed off with CPEB1+apyrase (1U/ml). 4 additional agonist responses were then measured every 5 minutes in the continued presence of the test IgG or an isotype control IgG (NIP 228).

Four IgGs were found to significantly inhibit human P2X4 currents; Antibody Nos. 1, 2, 3 and 4, of which two of the antibodies, 1 and 4, fully inhibited, with IC50's of 19.6 and 3.8 nM, respectively. Inhibition of P2X4 currents was rapid, occurring at the first time point following IgG addition, whereas the isotype control IgG NIP 228 CMC had no significant effect. By comparison, only 1 antibody that fully inhibited human P2X4 currents was isolated from the total screening of 33 000 scFv's from the CAT 2.0 libraries (Lloyd et al., 2009, Protein Engineering Design and Selection 22(3) 159-168).

Antibodies (Abs) Binding and Function: Phage Display P2X4 Binding Antibodies

| Antibody number | Human P2X4 binding | Cynomologus P2X4 binding | Rat P2X4 binding | Mouse P2X4 binding |
|---|---|---|---|---|
| 1 | + | − | − | − |
| 2 | + | − | − | − |
| 3 | + | − | − | − |
| 4 | + | − | − | − |

Potency of Antibodies from Lead Panel in an Ephys Assay

| Antibody number | Antibody code | Conc (μM) | Fraction of control at human P2X4 (Exp 1) | | | Fraction of control at human P2X4 (Exp 2) | | | IC50 (nM) |
|---|---|---|---|---|---|---|---|---|---|
| | | | Mean | SD | n | Mean | SD | n | |
| Control | NIP 228 | 7.8 | 1.40 | 0.05 | 3 | 1.36 | 0.08 | 4 | N/A |
| 1 | — | 2.3 | 0.00 | 0.01 | 3 | 0.02 | 0.01 | 4 | 19.6 |
| 2 | — | 2.8 | 0.47 | 0.11 | 4 | 0.34 | 0.04 | 4 | N/A |
| 3 | — | 2.0 | 0.19 | 0.09 | 3 | 0.41 | 0.10 | 3 | 50 |
| 4 | — | 4.9 | 0.05 | 0.07 | 3 | 0.03 | 0.03 | 3 | 3.9 |

The invention claimed is:

1. A phage library displaying human scFv, wherein at least 60% of the human scFv variable heavy chain CDR3 (CDR H3) displayed by the library is 20 amino acids in length and comprises the following amino acid sequences (SEQ ID NO: 15):

position 1: selected from the list consisting of: R, K, D, E, P, S, G, A, V position 2: selected from the list consisting of: R, D, E, H, P, Y, S, G, F, L, V position 3: selected from the list consisting of: R, D, H, P, Y, S, T, G, A, F, V position 4: selected from the list consisting of: R, K, D, H, P, Y, W, S, G, A, F, L, V, I
position 5: selected from the list consisting of: K, D, H, P, Y, S, T, G, A, M, L, V, I
position 6: selected from the list consisting of: D, P, Y, S, G, A, M, F, L, V, I
position 7: selected from the list consisting of: R, K, D, E, P, Y, S, T, G, F, V, I
position 8: selected from the list consisting of: R, D, P, Y, S, T, G, A, M, F, L, V, I
position 9: selected from the list consisting of: R, D, P, Y, W, S, T, G, A, M, F, L, V, I
position 10: selected from the list consisting of: R, D, P, Y, S, T, G, A, M, F, L, V, I
position 11: selected from the list consisting of: R, D, E, P, Y, S, T, G, A, F, L, V, I
position 12: selected from the list consisting of: R, K, D, E, P, Y, S, T, G, A, F, L, V, I
position 13: selected from the list consisting of: R, K, D, E, P, Y, S, T, G
position 14: selected from the list consisting of: R, K, E, P, Y, S, T, G, A
position 15: selected from the list consisting of: R, E, P, Y, S, T, G, A, F, L, V
position 16: selected from the list consisting of: D, Y, S, T, G, F, L
position 17: selected from the list consisting of: Y, W, G, A
position 18: selected from the list consisting of: P, M, F, L
position 19: D
position 20: selected from the list consisting of: P, Y, L, V, I.

2. A method of generating a functional human antibody, or antigen binding fragment thereof, to a target antigen, the method comprising isolating a human antibody specific for the target antigen from the library as claimed in claim 1.

3. A phage library displaying human scFv, wherein at least 60% of the human scFv variable heavy chain CDR3 (CDR H3) displayed by the library is 21 amino acids in length and comprises the following amino acid sequences (SEQ ID NO: 16):
position 1: selected from the list consisting of: R, K, D, E, P, S, G, A, V
position 2: selected from the list consisting of: R, D, E, H, P, Y, S, G, F, L, V
position 3: selected from the list consisting of: R, D, H, P, Y, S, T, G, A, F, V
position 4: selected from the list consisting of: R, K, D, H, P, Y, W, S, G, A, F, L, V, I
position 5: selected from the list consisting of: K, D, H, P, Y, S, T, G, A, M, L, V, I
position 6: selected from the list consisting of: D, P, Y, S, G, A, M, F, L, V, I
position 7: selected from the list consisting of: R, K, D, E, P, Y, S, T, G, F, V, I
position 8: selected from the list consisting of: R, D, P, Y, W, S, T, G, A, M, F, L, V, I
position 9: selected from the list consisting of: R, D, P, Y, W, S, T, G, A, F, L, V, I
position 10: selected from the list consisting of: R, D, E, P, Y, W, S, G, A, L, V, I
position 11: selected from the list consisting of: R, D, P, Y, S, T, G, A, M, F, L, V, I
position 12: selected from the list consisting of: R, D, E, P, Y, S, T, G, A, F, L, V, I
position 13: selected from the list consisting of: R, K, D, E, P, Y, S, T, G, A, F, L, V, I
position 14: selected from the list consisting of: R, K, D, E, P, Y, S, T, G
position 15: selected from the list consisting of: R, K, E, P, Y, S, T, G, A
position 16: selected from the list consisting of: R, E, P, Y, S, T, G, A, F, L, V
position 17: selected from the list consisting of: D, Y, S, T, G, F, L
position 18: selected from the list consisting of: Y, W, G, A
position 19: selected from the list consisting of: P, M, F, L
position 20: D
position 21: selected from the list consisting of: P, Y, L, V, I.

4. A phage library displaying human scFv, wherein at least 60% of the human scFv variable heavy chain CDR3 (CDR H3) displayed by the library is 22 amino acids in length and comprises the following amino acid sequences (SEQ ID NO: 17):
position 1: selected from the list consisting of: R, K, D, E, P, S, G, A, V
position 2: selected from the list consisting of: R, D, E, H, P, Y, S, G, F, L, V
position 3: selected from the list consisting of: R, D, H, P, Y, S, T, G, A, F, V
position 4: selected from the list consisting of: R, K, D, H, P, Y, W, S, G, A, F, L, V, I
position 5: selected from the list consisting of: K, D, H, P, Y, S, T, G, A, M, L, V, I
position 6: selected from the list consisting of: D, P, Y, S, G, A, M, F, L, V, I
position 7: selected from the list consisting of: R, K, D, E, P, Y, S, T, G, F, V, I
position 8: selected from the list consisting of: R, D, P, Y, S, T, G, A, M, F, L, V, I
position 9: selected from the list consisting of: R, D, P, Y, W, S, T, G, A, M, F, L, V, I
position 10: selected from the list consisting of: R, D, P, Y, W, S, T, G, A, F, L, V, I
position 11: selected from the list consisting of: R, D, E, P, Y, W, S, G, A, L, V, I
position 12: selected from the list consisting of: R, D, P, Y, S, T, G, A, M, F, L, V, I
position 13: selected from the list consisting of: R, D, E, P, Y, S, T, G, A, F, L, V, I
position 14: selected from the list consisting of: R, K, D, E, P, Y, S, T, G, A, F, L, V, I
position 15: selected from the list consisting of: R, K, D, E, P, Y, S, T, G
position 16: selected from the list consisting of: R, K, E, P, Y, S, T, G, A
position 17: selected from the list consisting of: R, E, P, Y, S, T, G, A, F, L, V
position 18: selected from the list consisting of: D, Y, S, T, G, F, L
position 19: selected from the list consisting of: Y, W, G, A
position 20: selected from the list consisting of: P, M, F, L
position 21: D
position 22: selected from the list consisting of: P, Y, L, V, I.

* * * * *